US011033512B2

(12) United States Patent
Mohr et al.

(10) Patent No.: US 11,033,512 B2
(45) Date of Patent: Jun. 15, 2021

(54) TRANSDERMAL THERAPEUTIC SYSTEM CONTAINING ASENAPINE AND SILICONE ACRYLIC HYBRID POLYMER

(71) Applicant: LTS LOHMANN Therapie-Systeme AG, Andernach (DE)

(72) Inventors: Patrick Mohr, Bad Breisig (DE); René Rietscher, Neuwied (DE); René Eifler, Koblenz (DE); Olga Bourquain, Dürrholz (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 0 days.

(21) Appl. No.: 16/623,034

(22) PCT Filed: Jun. 25, 2018

(86) PCT No.: PCT/EP2018/066950
§ 371 (c)(1),
(2) Date: Dec. 16, 2019

(87) PCT Pub. No.: WO2019/002204
PCT Pub. Date: Jan. 3, 2019

(65) Prior Publication Data
US 2020/0179298 A1 Jun. 11, 2020

(30) Foreign Application Priority Data
Jun. 26, 2017 (EP) .................................... 17177862

(51) Int. Cl.
A61K 9/70 (2006.01)
A61P 25/18 (2006.01)
A61K 31/407 (2006.01)

(52) U.S. Cl.
CPC .......... *A61K 9/7061* (2013.01); *A61K 31/407* (2013.01); *A61P 25/18* (2018.01)

(58) Field of Classification Search
CPC .. A61K 31/407; A61K 9/7069; A61K 9/7061; A61P 25/18
See application file for complete search history.

(56) References Cited

U.S. PATENT DOCUMENTS

| | | | |
|---|---|---|---|
| 4,145,434 A | 3/1979 | Van Der Burg | |
| 4,158,059 A | 6/1979 | Van Der Burg | |
| 5,112,842 A | 5/1992 | Zierenberg et al. | |
| 5,446,070 A | 8/1995 | Mantelle | |
| 5,656,286 A | 8/1997 | Miranda et al. | |
| 5,763,476 A | 6/1998 | Delbressine et al. | |
| 5,830,497 A | 11/1998 | Yamanaka et al. | |
| 6,190,690 B1 | 2/2001 | Park et al. | |
| 6,235,306 B1 | 5/2001 | Miranda et al. | |
| 6,620,429 B1 | 9/2003 | Mueller | |
| 6,638,528 B1 | 10/2003 | Kanios | |
| 6,669,953 B1 | 12/2003 | Kamiyama | |
| 6,797,280 B1 | 9/2004 | Kitazono et al. | |
| 6,964,962 B2 | 11/2005 | Wong et al. | |
| 7,641,703 B2 | 1/2010 | Guerin et al. | |
| 7,650,848 B2 | 1/2010 | Brennan et al. | |
| 7,744,918 B2 | 6/2010 | Yamaguchi et al. | |
| 7,875,729 B2 | 1/2011 | Zhu et al. | |
| 7,884,096 B2 | 2/2011 | Buntinx | |
| 7,956,202 B2 | 6/2011 | Kemperman et al. | |
| 7,964,739 B2 | 6/2011 | Kemperman | |
| 7,973,043 B2 | 7/2011 | Migaly | |
| 7,988,991 B2 | 8/2011 | Tateishi et al. | |
| 8,022,228 B2 | 9/2011 | Heeres | |
| 8,173,637 B2 | 5/2012 | Liu et al. | |
| 8,202,525 B2 | 6/2012 | Crain et al. | |
| 8,227,623 B2 | 7/2012 | Kemperman et al. | |
| 8,288,564 B2 | 10/2012 | Wang et al. | |
| 8,304,431 B2 | 11/2012 | Buntinx | |
| 8,309,120 B2 | 11/2012 | Koch et al. | |
| 8,318,813 B2 | 11/2012 | Sanfilippo | |
| 8,372,414 B2 | 2/2013 | Crain et al. | |
| 8,409,609 B2 | 4/2013 | Inosaka et al. | |
| 8,420,117 B2 | 4/2013 | Chono et al. | |
| 8,426,610 B2 | 4/2013 | Kemperman et al. | |
| 8,431,552 B2 | 4/2013 | Chen | |
| 8,512,742 B2 | 8/2013 | Amano et al. | |
| 8,580,281 B2 | 11/2013 | Morimoto et al. | |

(Continued)

FOREIGN PATENT DOCUMENTS

| | | |
|---|---|---|
| CN | 1121854 C | 9/2003 |
| CN | 102746209 A | 10/2012 |

(Continued)

OTHER PUBLICATIONS

Health Canada, "A Report on Mental Illnesses in Canada," Health Canada Editorial Board Mental Illnesses, Canada, pp. 1-91 (Oct. 2002).

Health Canada, "A Report on Mental Illnesses in Canada," Health Canada Editorial Board Mental Illnesses, Canada, pp. 92-111 (Oct. 2002).

Acosta, F.J., et al., "Medication Adherence in Schizophrenia," World Journal of Psychiatry 2(5):74-82, Baishideng Publishing Group, United States (Oct. 2012).

(Continued)

*Primary Examiner* — Blessing M Fubara

(74) *Attorney, Agent, or Firm* — Sterne, Kessler, Goldstein & Fox P.L.L.C.; Matthew S. Bodenstein

(57) ABSTRACT

The present invention relates to transdermal therapeutic systems (TTS) for the transdermal administration of asenapine comprising an asenapine-containing layer structure, said asenapine-containing layer structure comprising A) a backing layer and B) an asenapine-containing layer, wherein the transdermal therapeutic system comprises a silicone acrylic hybrid polymer.

19 Claims, 6 Drawing Sheets

(56) References Cited

U.S. PATENT DOCUMENTS

| | | |
|---|---|---|
| 8,580,972 B2 | 11/2013 | Bosch et al. |
| 8,591,941 B2 | 11/2013 | Kanios et al. |
| 8,614,274 B2 | 12/2013 | Jackson et al. |
| 8,617,577 B2 | 12/2013 | Crain et al. |
| 8,624,052 B2 | 1/2014 | Johnson et al. |
| 8,632,802 B2 | 1/2014 | Kanios |
| 8,652,776 B2 | 2/2014 | Lavedan et al. |
| 8,653,280 B2 | 2/2014 | Dalmases Barjoan et al. |
| 8,658,687 B2 | 2/2014 | Faassen et al. |
| 8,703,175 B2 | 4/2014 | Kanios et al. |
| 8,741,319 B2 | 6/2014 | Crain et al. |
| 8,779,161 B2 | 7/2014 | Katkam et al. |
| 8,846,093 B2 | 9/2014 | Govil et al. |
| 8,933,114 B2 | 1/2015 | Ventimiglia et al. |
| 8,945,063 B2 | 2/2015 | Wotton et al. |
| 8,986,677 B2 | 3/2015 | Altschul et al. |
| 9,011,910 B2 | 4/2015 | Schwarz |
| 9,017,737 B2 | 4/2015 | Kikuchi et al. |
| 9,050,348 B2 | 6/2015 | Kydonieus et al. |
| 9,073,890 B2 | 7/2015 | Suzuki et al. |
| 9,095,516 B2 | 8/2015 | Middelbeek et al. |
| 9,119,794 B2 | 9/2015 | Middelbeek et al. |
| 9,145,421 B2 | 9/2015 | Aryan et al. |
| 9,169,262 B2 | 10/2015 | Blatter et al. |
| 9,180,191 B2 | 11/2015 | Sheehan et al. |
| 9,198,877 B2 | 12/2015 | Jackson et al. |
| 9,205,060 B2 | 12/2015 | Kamakura et al. |
| 9,226,902 B2 | 1/2016 | Tang |
| 9,267,151 B2 | 2/2016 | Guerrero Martinez et al. |
| 9,295,726 B2 | 3/2016 | Kulakofsky et al. |
| 9,303,036 B2 | 4/2016 | Blatter et al. |
| 9,328,387 B2 | 5/2016 | Lavedan et al. |
| 9,370,495 B2 | 6/2016 | Toshimitsu et al. |
| 9,393,367 B2 | 7/2016 | Wotton et al. |
| 9,421,178 B2 | 8/2016 | Fogel et al. |
| 9,427,420 B2 | 8/2016 | Fogel et al. |
| 9,447,066 B2 | 9/2016 | Okumura et al. |
| 9,447,109 B2 | 9/2016 | Frigoli et al. |
| 9,457,014 B2 | 10/2016 | Lawton et al. |
| 9,457,018 B2 | 10/2016 | Scheel-Krüger et al. |
| 9,486,453 B2 | 11/2016 | Javitt |
| 9,499,816 B2 | 11/2016 | Mann |
| 9,500,642 B2 | 11/2016 | Blackman et al. |
| 9,505,771 B2 | 11/2016 | Bertran et al. |
| 9,511,051 B2 | 12/2016 | Suzuki et al. |
| 9,526,718 B2 | 12/2016 | Lee et al. |
| 9,533,994 B2 | 1/2017 | Solà Carandell et al. |
| 9,844,515 B2 | 12/2017 | Fleschhut et al. |
| 10,071,090 B2 | 9/2018 | Stinchcomb et al. |
| 2003/0109546 A1 | 6/2003 | Fenton |
| 2003/0228354 A1 | 12/2003 | Muraoka et al. |
| 2004/0033254 A1 | 2/2004 | Song et al. |
| 2004/0202704 A1 | 10/2004 | Sharma et al. |
| 2005/0004106 A1 | 1/2005 | Romano |
| 2005/0171086 A1 | 8/2005 | Brodney et al. |
| 2005/0209250 A1 | 9/2005 | Romano |
| 2005/0215571 A1 | 9/2005 | Romano |
| 2005/0245539 A1 | 11/2005 | Mendla et al. |
| 2005/0256112 A1 | 11/2005 | Brodney et al. |
| 2006/0019969 A1 | 1/2006 | Baeyens Cabrera |
| 2006/0084692 A1 | 4/2006 | Erik Wong et al. |
| 2006/0128688 A1 | 6/2006 | Tonnaer |
| 2006/0150989 A1 | 7/2006 | Migaly |
| 2006/0177493 A1 | 8/2006 | Altenschopfer et al. |
| 2006/0204486 A1 | 9/2006 | Pyke et al. |
| 2006/0229299 A1 | 10/2006 | Bruinvels |
| 2006/0286160 A1 | 12/2006 | Satoda et al. |
| 2006/0292210 A1 | 12/2006 | Inosaka et al. |
| 2007/0015763 A1 | 1/2007 | Romano |
| 2007/0148218 A1 | 6/2007 | Gordon |
| 2007/0191350 A1 | 8/2007 | Field et al. |
| 2007/0203119 A1 | 8/2007 | Danjou et al. |
| 2007/0259952 A1 | 11/2007 | Svensson |
| 2008/0020028 A1 | 1/2008 | Shevchuk et al. |
| 2008/0045512 A1 | 2/2008 | Duplantier et al. |
| 2008/0090892 A1 | 4/2008 | Casteel et al. |
| 2008/0103155 A1 | 5/2008 | Mendla et al. |
| 2008/0131490 A1 | 6/2008 | Hanatani et al. |
| 2008/0138388 A1 | 6/2008 | Aida et al. |
| 2008/0226697 A1 | 9/2008 | Yamaguchi et al. |
| 2008/0226698 A1 | 9/2008 | Tang et al. |
| 2008/0306133 A1 | 12/2008 | Van Der Sterren et al. |
| 2009/0004255 A1 | 1/2009 | Uchida et al. |
| 2009/0042950 A1 | 2/2009 | Pandya |
| 2009/0075974 A1 | 3/2009 | Yamaguchi et al. |
| 2009/0111837 A1 | 4/2009 | Cox et al. |
| 2009/0148504 A1 | 6/2009 | Kamiyama et al. |
| 2009/0169605 A1 | 7/2009 | Maeda et al. |
| 2009/0209608 A1 | 8/2009 | Czarnik |
| 2010/0004259 A1 | 1/2010 | Liu et al. |
| 2010/0178323 A1 | 7/2010 | Kydonieus et al. |
| 2010/0234288 A1 | 9/2010 | Jain et al. |
| 2010/0297181 A1 | 11/2010 | Hanada et al. |
| 2011/0105519 A1 | 5/2011 | Mendla et al. |
| 2011/0106006 A1 | 5/2011 | Martin et al. |
| 2011/0166194 A1 | 7/2011 | Blumberg et al. |
| 2011/0178068 A1 | 7/2011 | Almarsson et al. |
| 2011/0262442 A1 | 10/2011 | Hamilton et al. |
| 2011/0269777 A1 | 11/2011 | Bachurin et al. |
| 2011/0306596 A1 | 12/2011 | Rao et al. |
| 2012/0010242 A1 | 1/2012 | Buntinx |
| 2012/0122793 A1 | 5/2012 | Johnson et al. |
| 2012/0157420 A1 | 6/2012 | Schneider |
| 2012/0201804 A1 | 8/2012 | Williams et al. |
| 2012/0237561 A1 | 9/2012 | Faassen et al. |
| 2012/0315318 A1 | 12/2012 | Toshimitsu et al. |
| 2013/0053357 A1 | 2/2013 | Kuma et al. |
| 2013/0071412 A1 | 3/2013 | Leighton et al. |
| 2013/0143867 A1 | 6/2013 | Fogel et al. |
| 2013/0203766 A1 | 8/2013 | Mendla et al. |
| 2013/0217681 A1 | 8/2013 | Weizman et al. |
| 2013/0224110 A1 | 8/2013 | Bynoe |
| 2013/0245004 A1 | 9/2013 | Fogel et al. |
| 2013/0245253 A1 | 9/2013 | Marx et al. |
| 2013/0274466 A1 | 10/2013 | Gorin et al. |
| 2013/0344125 A1 | 12/2013 | Govender et al. |
| 2014/0018348 A1 | 1/2014 | Javitt |
| 2014/0037710 A1 | 2/2014 | Hashimoto et al. |
| 2014/0080911 A1 | 3/2014 | Stefanelli et al. |
| 2014/0121202 A1 | 5/2014 | Johnson et al. |
| 2014/0163083 A1 | 6/2014 | Blatter et al. |
| 2014/0206667 A1 | 7/2014 | Gallagher |
| 2014/0221742 A1 | 8/2014 | Bandy et al. |
| 2014/0221942 A1 | 8/2014 | Scasso et al. |
| 2014/0271866 A1 | 9/2014 | Ryoo |
| 2014/0271923 A1 | 9/2014 | Reid |
| 2014/0276478 A1 | 9/2014 | Liao et al. |
| 2014/0276479 A1 | 9/2014 | Nguyen et al. |
| 2014/0287529 A1 | 9/2014 | Leider |
| 2014/0315886 A1 | 10/2014 | Suzuki et al. |
| 2014/0336391 A1 | 11/2014 | Sharma et al. |
| 2014/0350064 A1 | 11/2014 | Chen |
| 2014/0350081 A1 | 11/2014 | Hill et al. |
| 2015/0037335 A1 | 2/2015 | Westbrook |
| 2015/0099015 A1 | 4/2015 | Tsai |
| 2015/0099741 A1 | 4/2015 | Li et al. |
| 2015/0111834 A1 | 4/2015 | Cheng et al. |
| 2015/0141274 A1 | 5/2015 | Friedman et al. |
| 2015/0202183 A1* | 7/2015 | Suzuki ............... A61K 9/7069 424/443 |
| 2015/0224120 A1 | 8/2015 | Clelland et al. |
| 2015/0231154 A1 | 8/2015 | Theobald et al. |
| 2015/0231250 A1 | 8/2015 | Sonobe et al. |
| 2015/0250716 A1 | 9/2015 | Watkins |
| 2015/0272946 A1 | 10/2015 | Sato et al. |
| 2015/0292014 A1 | 10/2015 | Zhu et al. |
| 2015/0320739 A1 | 11/2015 | Mendla et al. |
| 2015/0328163 A1 | 11/2015 | Gujjar et al. |
| 2015/0329497 A1 | 11/2015 | Pinkerton et al. |
| 2015/0343144 A1 | 12/2015 | Altschul et al. |
| 2015/0359566 A1 | 12/2015 | Sillender |
| 2016/0022571 A1 | 1/2016 | Schwarz et al. |
| 2016/0024011 A1 | 1/2016 | Zeidan et al. |
| 2016/0030362 A1 | 2/2016 | Liao et al. |

(56) References Cited

U.S. PATENT DOCUMENTS

| | | |
|---|---|---|
| 2016/0101075 A1 | 4/2016 | Fogel et al. |
| 2016/0199313 A1 | 7/2016 | LeDonne et al. |
| 2016/0235677 A1 | 8/2016 | Hoerr et al. |
| 2016/0303102 A1 | 10/2016 | Albayrak |
| 2016/0310502 A1 | 10/2016 | Vanover et al. |
| 2016/0317465 A1 | 11/2016 | Shinoda et al. |
| 2017/0007537 A1 | 1/2017 | Reddy et al. |
| 2017/0079932 A1 | 3/2017 | Emgenbroich et al. |
| 2017/0202830 A1 | 7/2017 | Stinchcomb et al. |
| 2018/0028461 A1 | 2/2018 | Singh et al. |
| 2018/0028464 A1 | 2/2018 | Komoda et al. |
| 2018/0193283 A1 | 7/2018 | Mohr |
| 2018/0207108 A1 | 7/2018 | Sonobe et al. |
| 2019/0336454 A1 | 11/2019 | Mohr et al. |
| 2020/0085759 A1 | 3/2020 | Mohr et al. |

FOREIGN PATENT DOCUMENTS

| | | |
|---|---|---|
| CN | 102858372 A | 1/2013 |
| CN | 102952144 A | 3/2013 |
| CN | 102976929 A | 3/2013 |
| CN | 102976998 A | 3/2013 |
| CN | 103113379 A | 5/2013 |
| CN | 103120688 A | 5/2013 |
| CN | 101851242 B | 7/2013 |
| CN | 103183680 A | 7/2013 |
| CN | 102229613 B | 8/2013 |
| CN | 102657635 B | 8/2013 |
| CN | 103254202 A | 8/2013 |
| CN | 103760258 A | 4/2014 |
| CN | 103760280 A | 4/2014 |
| CN | 103772400 A | 5/2014 |
| CN | 103772401 A | 5/2014 |
| CN | 103772402 A | 5/2014 |
| CN | 103864802 A | 6/2014 |
| CN | 103893139 A | 7/2014 |
| CN | 103083284 B | 8/2014 |
| CN | 103099799 B | 8/2014 |
| CN | 103965206 A | 8/2014 |
| CN | 104000800 A | 8/2014 |
| CN | 104098580 A | 10/2014 |
| CN | 104133010 A | 11/2014 |
| CN | 104133012 A | 11/2014 |
| CN | 104297366 A | 1/2015 |
| CN | 104447770 A | 3/2015 |
| CN | 104447771 A | 3/2015 |
| CN | 104487072 A | 4/2015 |
| CN | 104507472 A | 4/2015 |
| CN | 103342707 B | 9/2015 |
| CN | 104974167 A | 10/2015 |
| CN | 104974168 A | 10/2015 |
| CN | 103254201 B | 4/2016 |
| CN | 103351393 B | 4/2016 |
| CN | 104098580 B | 4/2016 |
| CN | 105377245 A | 5/2016 |
| CN | 105566336 A | 5/2016 |
| CN | 105693735 A | 6/2016 |
| CN | 105813636 A | 7/2016 |
| CN | 103864802 B | 8/2016 |
| EP | 0569096 A1 | 11/1993 |
| EP | 0730865 B1 | 12/2001 |
| EP | 1547650 A1 | 6/2005 |
| EP | 1181935 B1 | 9/2005 |
| EP | 1576985 A1 | 9/2005 |
| EP | 1684681 A1 | 8/2006 |
| EP | 1765310 A2 | 3/2007 |
| EP | 2236138 A1 | 10/2010 |
| EP | 2468750 A1 | 6/2012 |
| EP | 2154134 B1 | 10/2012 |
| EP | 2599847 A1 | 6/2013 |
| EP | 2878298 A1 | 6/2015 |
| EP | 3020782 A1 | 5/2016 |
| EP | 3031458 A1 | 6/2016 |
| EP | 3329914 A1 | 6/2018 |
| EP | 3329915 A1 | 6/2018 |
| EP | 3338768 A1 | 6/2018 |
| JP | 5301190 B2 | 9/2013 |
| JP | 2014214109 A | 11/2014 |
| JP | 2016056142 A | 4/2016 |
| JP | 2017178799 A | 10/2017 |
| KR | 20130120648 A | 11/2013 |
| KR | 20160107610 A | 9/2016 |
| KR | 20160108258 A | 9/2016 |
| WO | WO-8600806 A1 | 2/1986 |
| WO | WO-9518603 A1 | 7/1995 |
| WO | WO-9854186 A1 | 12/1998 |
| WO | WO-9932108 A1 | 7/1999 |
| WO | WO-0064418 A2 | 11/2000 |
| WO | WO-03013482 A1 | 2/2003 |
| WO | WO-03066039 A1 | 8/2003 |
| WO | WO-2004017941 A2 | 3/2004 |
| WO | WO-2004039322 A2 | 5/2004 |
| WO | WO-2005084654 A2 | 9/2005 |
| WO | WO-2006000222 A2 | 1/2006 |
| WO | WO-2006023497 A2 | 3/2006 |
| WO | WO-2006079547 A2 | 8/2006 |
| WO | WO 2006106135 A1 | 10/2006 |
| WO | WO-2006106136 A1 | 10/2006 |
| WO | WO-2007017750 A1 | 2/2007 |
| WO | WO-2007046554 A1 | 4/2007 |
| WO | WO-2007124757 A2 | 11/2007 |
| WO | WO-2007137224 A2 | 11/2007 |
| WO | WO-2007145996 A2 | 12/2007 |
| WO | WO-2007137224 A3 | 1/2008 |
| WO | WO-2008003460 A1 | 1/2008 |
| WO | WO-2008066180 A1 | 6/2008 |
| WO | WO-2008078482 A1 | 7/2008 |
| WO | WO-2008141438 A1 | 11/2008 |
| WO | WO-2009000890 A2 | 12/2008 |
| WO | WO-2009017453 A1 | 2/2009 |
| WO | WO-2009102962 A2 | 8/2009 |
| WO | WO-2009135091 A1 | 11/2009 |
| WO | WO-2010060742 A1 | 6/2010 |
| WO | WO-2010073326 A1 | 7/2010 |
| WO | WO-2010074182 A1 | 7/2010 |
| WO | WO-2010074183 A1 | 7/2010 |
| WO | WO-2010080757 A2 | 7/2010 |
| WO | WO-2010110914 A2 | 9/2010 |
| WO | WO-2010112530 A1 | 10/2010 |
| WO | WO-2010119455 A2 | 10/2010 |
| WO | WO-2010124187 A2 | 10/2010 |
| WO | WO-2010127674 A1 * | 11/2010 | ............... A61K 9/12 |
| WO | WO-2011012654 A1 | 2/2011 |
| WO | WO-2011047341 A2 | 4/2011 |
| WO | WO-2011085188 A1 | 7/2011 |
| WO | WO-2011087755 A2 | 7/2011 |
| WO | WO-2011101799 A1 | 8/2011 |
| WO | WO-2011107855 A2 | 9/2011 |
| WO | WO-2011143755 A2 | 11/2011 |
| WO | WO-2012038975 A2 | 3/2012 |
| WO | WO-2012065102 A2 | 5/2012 |
| WO | WO-2012066565 A2 | 5/2012 |
| WO | WO-2012114325 A1 | 8/2012 |
| WO | WO-2012123325 A1 | 9/2012 |
| WO | WO-2012163665 A1 | 12/2012 |
| WO | WO-2013024492 A2 | 2/2013 |
| WO | WO-2013027052 A1 | 2/2013 |
| WO | WO-2013035109 A1 | 3/2013 |
| WO | WO-2013041435 A1 | 3/2013 |
| WO | WO-2013041604 A1 | 3/2013 |
| WO | WO-2013061247 A1 | 5/2013 |
| WO | WO-2013114400 A2 | 8/2013 |
| WO | WO-2013150032 A1 | 10/2013 |
| WO | WO-2013190481 A1 | 12/2013 |
| WO | WO-2014064076 A1 | 5/2014 |
| WO | WO-2014076643 A1 | 5/2014 |
| WO | WO-2014078377 A1 | 5/2014 |
| WO | WO-2014080378 A1 | 5/2014 |
| WO | WO-2014084401 A1 | 6/2014 |
| WO | WO-2014127786 A1 | 8/2014 |
| WO | WO-2014152965 A2 | 9/2014 |
| WO | WO-2014160026 A2 | 10/2014 |
| WO | WO-2014160155 A2 | 10/2014 |
| WO | WO-2014160167 A1 | 10/2014 |

(56) References Cited

FOREIGN PATENT DOCUMENTS

| WO | WO-2014207664 A2 | 12/2014 |
|----|------------------|---------|
| WO | WO-2015027342 A1 | 3/2015  |
| WO | WO-2014207664 A3 | 4/2015  |
| WO | WO-2015071831 A1 | 5/2015  |
| WO | WO-2015120317 A1 | 8/2015  |
| WO | WO-2015127416 A1 | 8/2015  |
| WO | WO-2015127556 A1 | 9/2015  |
| WO | WO-2015127557 A1 | 9/2015  |
| WO | WO-2015127558 A1 | 9/2015  |
| WO | WO-2015154025 A1 | 10/2015 |
| WO | WO-2015154030 A1 | 10/2015 |
| WO | WO-2015177212 A1 | 11/2015 |
| WO | WO-2015191554 A1 | 12/2015 |
| WO | WO-2016009063 A1 | 1/2016  |
| WO | WO-2016020573 A1 | 2/2016  |
| WO | WO-2016023658 A1 | 2/2016  |
| WO | WO-2016060564 A1 | 4/2016  |
| WO | WO-2016062285 A1 | 4/2016  |
| WO | WO-2016089737 A1 | 6/2016  |
| WO | WO-2016090228 A1 | 6/2016  |
| WO | WO-2016114655 A1 | 7/2016  |
| WO | WO-2016130408 A1 | 8/2016  |
| WO | WO-2016138138 A1 | 9/2016  |
| WO | WO-2016140087 A1 | 9/2016  |
| WO | WO-2016166679 A1 | 10/2016 |
| WO | WO-2016170102 A1 | 10/2016 |
| WO | WO 2016176519 A1 | 11/2016 |
| WO | WO-2016207466 A1 | 12/2016 |
| WO | WO-2017018321 A1 | 2/2017  |
| WO | WO-2017018322 A1 | 2/2017  |
| WO | WO-2017131034 A1 | 8/2017  |

OTHER PUBLICATIONS

Amato, D., et al., "Neuroadaptations to Antipsychotic Drugs: Insights From Pre-clinical and Human Post-mortem Studies," Neuroscience and Biobehavioral Reviews 76 (Pt B):317-335, Pergamon Press, United States (May 2017).

Andree, B., et al., "Central 5-HT2A and D2 Dopamine Receptor Occupancy After Sublingual Administration of ORG 5222 in Healthy Men," Psychopharmacology 131:339-345, Springer-Verlag, Germany (1997).

"Saphris®/Sycrest® (aseriapine) Bipolar 1 disorder, MSD," Monograph, 2011, 58 Pages.

"Asenapine maleate," Sicherheitsdatenblatt, Sigma-Aldrich, 2014, 7 Pages.

"Australian Public Assessment Report for Asenapine," Australian Government, Department of Health and Aging, Apr. 2011, 154 pages.

Balaraman, R., and Gandhi, H., "Asenapine, a New Sublingual Atypical Antipsychotic," Journal of Pharmacology & Pharmacotherapeutics 1(1):60-61, Medknow Publications and Media, India (Jan. 2010).

Bartlett, J.A., and Maarschalk, K., "Understanding the Oral Mucosal Absorption and Resulting Clinical Pharmacokinetics of Asenapine," AAPS PharmSciTech 13(4):1110-1115, Springer, United States (Dec. 2012).

Benson, H.A.E., and Watkinson, A.C., eds., "Transdermal and Topical Drug Delivery: Principles and Practice," 448 pages, John Wiley & Sons, Inc., United States (2012).

National Institute for Health and Care Excellence, "Bipolar disorder: assessment and management—clinical guideline," Published: Sep. 24, 2014, 46 Pages.

Bishara D and Taylor D., "Asenapine Monotherapy in the Acute Treatment of Both Schizophrenia and Bipolar I Disorder," Neuropsychiatric Disease and Treatment, 5:483-490, Dove Medical Press, New Zealand (2009).

Brisch R., et al., "The Role of Dopamine in Schizophrenia From a Neurobiological and Evolutionary Perspective: Old Fashioned, but Still in Vogue," Frontiers in Psychiatry, 5:47, Frontiers Research Foundation, Switzerland (May 2014).

Broekkamp, C.L., et al., "Behavioural Pharmacology of Trans-5-chloro-2-methyl-2,3,3a,12b-tetrahydro-1h-dibenz[2,3:6,7]oxepino-[4,5-c]pyrrolidine Maleate, a Compound Interacting With Dopaminergic and Serotonergic Receptors," Drug Discovery, 40 (5):544-549, Editio Cantor, Germany (May 1990).

Buchanan R.W., et al., "Asenapine Versus Olanzapine in People With Persistent Negative Symptoms of Schizophrenia," Journal of Clinical Psychopharmacology, 32(1):36-45, Williams and Wilkins, United States (Feb. 2012).

Byers A., et al., "Asenapine Versus Placebo for Schizophrenia," The Cochrane Database of Systematic Reviews, 2015 (11):CD011458, Wiley, United Kingdom (Nov. 2015).

Caresano C., et al., "Cost-effectiveness of Asenapine in the Treatment of Patients With Bipolar I Disorder With Mixed Episodes in an Italian Context," Advances in Therapy, 31 (8):873-890, Springer Healthcare Communications, United States (Aug. 2014).

Cazorla P., et al., "Safety and Tolerability of Switching to Asenapine From Other Antipsychotic Agents: Pooled Results From Two Randomized Multicenter Trials in Stable Patients With Persistent Negative Symptoms in Schizophrenia," Neuropsychiatric Disease and Treatment, 8:247-257, Dove Medical Press, New Zealand (2012).

Chapel S., et al., "Exposure-response Analysis in Patients With Schizophrenia to Assess the Effect of Asenapine on QTc Prolongation," Journal of Clinical Pharmacology, 49(11):1297-1308, Wiley, United Kingdom (Nov. 2009).

Cipriani, A., et al., "Comparative Efficacy and Acceptability of Antimanic Drugs in Acute Mania: a Multiple-treatments Meta-analysis," Lancet, 378(9799):1306-1315, Elsevier, United Kingdom (Oct. 2011).

Citrome L., "Asenapine for Schizophrenia and Bipolar Disorder: a Review of the Efficacy and Safety Profile for This Newly Approved Sublingually Absorbed Second-generation Antipsychotic," International Journal of Clinical Practice, 63 (12):1762-1784, Wiley, United Kingdom (Dec. 2009).

Citrome L., "Asenapine Review, Part I: Chemistry, Receptor Affinity Profile, Pharmacokinetics and Metabolism," Expert Opinion on Drug Metabolism & Toxicology, 10 (6):893-903, Inform Healthcare, United Kingdom (Jun. 2014).

Citrome L., "Asenapine Review, Part II: Clinical Efficacy, Safety and Tolerability," Expert Opinion on Drug Safety, 13 (6):803-830, Taylor & Francis, United Kingdom (Jun. 2014).

Citrome L., "Role of Sublingual Asenapine in Treatment of Schizophrenia," Neuropsychiatric Disease and Treatment, 7:325-339, Dove Medical Press, New Zealand (2011).

NCT01549041, "Once-Daily Asenapine for Schizophrenia," ClinicalTrials.gov, first received: Oct. 14, 2011, 3 pages.

Correll C.U., et al., "Cardiometabolic Risk of Second-generation Antipsychotic Medications During First-time Use in Children and Adolescents," JAMA, 302 (16):1765-1773, American Medical Association, United States (Oct. 2009).

Correll C.U., et al., "Lower Risk for Tardive Dyskinesia Associated With Second-generation Antipsychotics: a Systematic Review of 1-year Studies," The American Journal of Psychiatry, 161 (3):414-425, American Psychiatric Association, United States (Mar. 2004).

Correll C.U., et al., "What Are We Looking for in New Antipsychotics?," The Journal of Clinical Psychiatry, 72( Suppl 1):9-13, Physicians Postgraduate Press, United States (2011).

Costall, B., et al., "Actions of Org 5222 as a Novel Psychotropic Agent," Pharmacology Biochemistry and Behavior, 35(3):607-615, Elsevier, United States (Mar. 1990).

Cramer J.A and Rosenheck R., "Compliance With Medication Regimens for Mental and Physical Disorders," Psychiatric Services 49 (2):196-201, American Psychiatric Association, United States (Feb. 1998).

Davidson M., et al., "Cognitive Effects of Antipsychotic Drugs in First-episode Schizophrenia and Schizophreniform Disorder: a Randomized, Open-label Clinical Trial (EUFEST)," The American Journal of Psychiatry, 166 (6):675-682, American Psychiatric Association, United States (Jun. 2009).

De Hert M., et al., "Metabolic and Cardiovascular Adverse Effects Associated With Antipsychotic Drugs," Nature Reviews Endocrinology, 8(2):114-126, Nature Publishing Group, United Kingdom (Oct. 2011).

(56) References Cited

OTHER PUBLICATIONS

"Die Behandlung Der Bipilaren Erkrankung," Thinking ahead in CNS, AstraZeneca, 20 pages (2003).

Dogterom, P., et al., "Asenapine Safety, Tolerability, and Pharmacokinetics After Single and Multiple Doses in Healthy Volunteers," Clinical Pharmacology in Drug Development, 1(4):131-143, Wiley, United States (Oct. 2012).

Dogterom, P., et al., "The Effect of Food on the High Clearance Drug Asenapine After Sublingual Administration to Healthy Male Volunteers," European Journal of Clinical Pharmacology, 71(1):65-74, Springer, Germany (Jan. 2015).

"Draft Guidance on Asenapine Maleate—Contains Nonbinding Recommendations," 4 pages (2013).

Dubovsky S.L., et al., "Short-term Safety and Pharmacokinetic Profile of Asenapine in Older Patients With Psychosis," International Journal of Geriatric Psychiatry, 27(5):472-482, John Wiley, United Kingdom (May 2012).

"Evaluation of Medicines for Human Use," European Medicine Agency, An agency of the European Union, 2010, 88 pages.

Fagiolini, A., et al., "Asenapine for the Treatment of Manic and Mixed Episodes Associated With Bipolar I Disorder: From Clinical Research to Clinical Practice," Expert Opinion on Pharmacotherapy, 14(4):489-504, Informa Healthcare, United Kingdom (Mar. 2013).

Findling R.L., et al., "Long-term Safety of Asenapine in Pediatric Patients Diagnosed With Bipolar I Disorder: a 50-week Open-label, Flexible-dose Trial," Paediatric Drugs, 18 (5):367-378, Springer International, Switzerland (Oct. 2016).

Fleischhacker W.W., et al., "Schizophrenia—time to Commit to Policy Change," Schizophrenia Bulletin, 40 (Suppl 3):S165-S194, Oxford University Press, United Kingdom (Apr. 2014).

Fleming, K., et al., "P.3.c.073 Effects of Asenapine on Cognitive Function in Acute Schizophrenia: a Placebo- and Risperidone-controlled Trial," European Neuropsychopharmacology, 17(4):S466-S467, Elsevier, Netherlands (Oct. 2007).

Fountoulakis K.N., et al., "The International College of Neuropsychopharmacology (CINP) Treatment Guidelines for Bipolar Disorder in Adults (CINP-BD-2017), Part 1: Background and Methods of the Development of Guidelines," International Journal of Neuropsychopharmacology, 20(2):98-120, Oxford University Press, United Kingdom (2017).

Fountoulakis K.N., et al., "The International College of Neuro-Psychopharmacology (CINP) Treatment Guidelines for Bipolar Disorder in Adults (CINP-BD-2017), Part 3: The Clinical Guidelines," The International Journal of Neuropsychopharmacology, 20(2):180-195, Oxford University Press, United Kingdom (Feb. 2017).

Franberg, O., et al., "Asenapine, a Novel Psychopharmacologic Agent Preclinical Evidence for Clinical Effects in Schizophrenia," Psychopharmacology, 196(3):417-429, Springer-Verlag, Germany (Feb. 2008).

Friberg, L.E., et al., "Modeling and Simulation of the Time Course of Asenapine Exposure Response and Dropout Patterns in Acute Schizophrenia," Clinical Pharmacology & Therapeutics, 86(1):84-91, Wiley, United States (Jul. 2009).

Geddes J., et al., "Atypical Antipsychotics in the Treatment of Schizophrenia: Systematic Overview and Meta-regression Analysis," BMJ (Clinical research ed.), 321 (7273):1371-1376, British Medical Association, United Kingdom (Dec. 2000).

Gerrits, M., et al., "Effect of Absorption Site on the Pharmacokinetics of Sublingual Asenapine in Healthy Male Subjects," Biopharmaceutics & Drug Disposition, 31(5-6):351-357, Wiley, United Kingdom (Jul. 2010).

Gerrits, M.G., et al., "Valproate Reduces the Glucuronidation of Asenapine Without Affecting Asenapine Plasma Concentrations," The Journal of Clinical Pharmacology, 52(5):757-765, Wiley, United Kingdom (May 2012).

Goodwin G.M., et al., "Evidence-based Guidelines for Treating Bipolar Disorder: Revised Second Edition—recommendations From the British Association for Psychopharmacology," Journal of Psychopharmacology ,23(4):346-388, Sage Publications, United States (Jun. 2009).

Grunder, G., et al., "Therapeutic Plasma Concentrations of Antidepressants and Antipsychotics: Lessons Front PET Imaging," Pharmacopsychiatry, 44(6):236-248, Georg Thieme Verlag, Germany (Sep. 2011).

Grunze H., et al., "The World Federation of Societies of Biological Psychiatry (Wfsbp) Guidelines for the Biological Treatment of Bipolar Disorders: Update 2012 on the Long-term Treatment of Bipolar Disorder," The World Journal of Biological Psychiatry, 14 (3):154-219, Informa Healthcare, United Kingdom (Apr. 2013).

Hagg S., et al., "Associations Between Venous Thromboembolism and Antipsychotics. A Study of the Who Database of Adverse Drug Reactions," Drug Safety, 31 (8):685-694, Springer International, New Zealand (2008).

Hiemke C., et al., "AGNP Consensus Guidelines for Therapeutic Drug Monitoring in Psychiatry: Update 2011.," Pharmacopsychiatry, 44 (6):195-235, Georg Thieme Verlag, Germany (Sep. 2011).

Hirschfeld, R.M, "Differential Diagnosis of Bipolar Disorder and Major Depressive Disorder," Journal of Affective Disorders, 169 Suppl 1:S12-S16, Elsevier/North-Holland Biomedical Press, Netherlands (Dec. 2014).

International Search Report and Written Opinion for International Application No. PCT/EP2018/066950, European Patent Office, Netherlands, dated Aug. 27, 2018, 9 pages.

Jones P.B., et al., "Randomized Controlled Trial of the Effect on Quality of Life of Second- Vs First-generation Antipsychotic Drugs in Schizophrenia: Cost Utility of the Latest Antipsychotic Drugs in Schizophrenia Study (Cutlass 1)," Archives of General Psychiatry, 63 (10):1079-1087, American Medical Association, United States (Oct. 2006).

Judd L.L and Aktskal H.S., "The Prevalence and Disability of Bipolar Spectrum Disorders in the Us Population: Re-analysis of the ECA Database Taking Into Account Subthreshold Cases," Journal of Affective Disorders, 73 (1-2):123-131, Elsevier/North-Holland Biomedical Press, Netherlands (Jan. 2003).

Kahn, R.S., et al., "Schizophrenia," Nature Reviews Disease Primers, 1:1-23, Nature Publishing Group, United Kingdom (Nov. 2015).

Kaminsky, B.M., et al., "Alternate Routes of Administration of Antidepressant and Antipsychotic Medications," Annals of Pharmacotherapy, 49(7):2 pages, Sage, United States (Jul. 2015).

Kane J.M., et al., "Efficacy and Safety of Asenapine in a Placebo- and Haloperidol-controlled Trial in Patients With Acute Exacerbation of Schizophrenia," Journal of Clinical Psychopharmacology, 30 (2):106-115, Williams and Wilkins, United States (Apr. 2010).

Kane, J.M., et al., "Non-adherence to Medication in Patients with Psychotic Disorders: Epidemiology, Contributing Factors and Management Strategies," World Psychiatry, 12(3):216-226, Masson Italy, Italy (Oct. 2013).

Kapil R.P., et al., "Once-weekly Transdermal Buprenorphine Application Results in Sustained and Consistent Steady-state Plasma Levels," Journal of Pain and Symptom Management, 46(1):65-75, Elsevier, United States (Jul. 2013).

"Asenapin," KBV, Wirkstoff AKTUELL, 4 pages (2013).

Kemp, D.E., et al., "Weight Change and Metabolic Effects of Asenapine in Patients With Schizophrenia and Bipolar Disorder," The Journal of Clinical Psychiatry, 75(3):238-245, Physicians Postgraduate Press, United States (Mar. 2014).

Kessler R.C., et al., "Prevalence, Severity, and Comorbidity of 12-month Dsm-iv Disorders in the National Comorbidity Survey Replication," Archives of General Psychiatry, 62 (6):617-627, American Medical Association, United States (Jun. 2005).

Ketter T.A., et al., "Long-term Safety and Tolerability of Asenapine: a Doable-blind, Uncontrolled, Long-term Extension Trial in Adults With an Acute Manic or Mixed Episode Associated With Bipolar I Disorder," Journal of Affective Disorders, 207:384-392, Elsevier/North-Holland Biomedical Press, Netherlands (Jan. 2017).

Kikkert, M.J., et al., "Medication Adherence in Schizophrenia: Exploring Patients', Carers' and Professionals' Views," Schizophrenia Bulletin, 32(4):786-794, Oxford University Press, United States (Oct. 2006).

(56) References Cited

OTHER PUBLICATIONS

Kinoshita, T., et al., "Efficacy and Safety of Asenapine in Asian Patients With an Acute Exacerbation of Schizophrenia: a Multicentre, Randomized, Double-blind, 6-week, Placebo-controlled Study." Psychopharmacology, 233(14):2663-2674, Springer-Verlag, Germany (Jul. 2016).

Lachaine J., et al., "Cost-effectiveness of asenapine in the treatment of bipolar disorder in Canada," BMC Psychiatry, 14:16, (2014).

Lachaine J., et al., "Cost-effectiveness of asenapine in the treatment of schizophrenia in Canada," Journal of Medical Economics, 17 (4):296-304, Taylor & Francis, United Kingdom (2014).

Landbloom R., et al., "Asenapine for the Treatment of Adults With an Acute Exacerbation of Schizophrenia: Results From a Randomized, Double-blind, Fixed-dose, Placebo-controlled Trial With Olanzapine as an Active Control," CNS Spectrums, 22 (4):333-341, Cambridge University Press, United Kingdom (Aug. 2017).

Landbloom, R.L., et al., "Asenapine: Efficacy and Safety of 5 and 10mg Bid in a 3-week, Randomized, Double-blind, Placebo-controlled Trial in Adults With a Manic or Mixed Episode Associated With Bipolar I Disorder," Journal of Affective Disorders, 190:103-110, Elsevier/North-Holland Biomedical Press, Netherlands (Jan. 2016).

Lehman A.F., et al., "Practice Guideline for the Treatment of Patients With Schizophrenia," Second Edition, Work Group on Schizophrenia, APA Practice Guidelines, 2010, 184 pages.

Leucht S., et al., "Comparative Efficacy and Tolerability of 15 Antipsychotic Drugs in Schizophrenia: a Multiple-treatments Meta-analysis," Lancet 382 (9896):951-962, Elsevier, United Kingdom (Sep. 2013).

Leucht S., et al., "New Generation Antipsychotics Versus Low-potency Conventional Antipsychotics: a Systematic Review and Meta-analysis," Lancet 361 (9369):1581-1589, Elsevier, United Kingdom (May 2003).

Lieberman J.A., et al., "Effectiveness of Antipsychotic Drugs in Patients With Chronic Schizophrenia," The New United Kingdom Journal of Medicine, 353 (12):1209-1223, Massachusetts Medical Society, United States (Sep. 2005).

Lincoln, M.J., "Asenepine for schizophrenia and bipolar 1 disorder," Bipolar Disorders 8(12):1-6, Dec. 2009.

Makdist J., et al., "Pityriasis Rosea-like Drug Reaction to Asenapine," Journal of Drugs in Dermatology: JDD, 12 (9):1050-1051, Physicians Continuing Education Corporation, United States (Sep. 2013).

Maletic, V., et al., "Integrated Neurobiology of Bipolar Disorder," Frontiers in Psychiatry, 5:98, Frontiers Research Foundation, Switzerland (2014).

Mutalik, S., "Nano-Carrier Based Transdermal Formulation of an Antipsychotic Drug: Development and In Vitro and In Vivo Evaluations," Conference: AAPS Annual Meeting and Exposition, Oct. 2015, 1 page.

Martin-Blanco, A., et al., "Asenapine in the Treatment of Borderline Personality Disorder: an Atypical Antipsychotic Alternative," International Clinical Psychopharmacology, 29(2):120-123, Lippincott Williams and Wilkins, United Kingdom (Mar. 2014).

Mauri M.C., et al., "Clinical Pharmacology of Atypical Antipsychotics: an Update," EXCLI Journal, 13:1163-1191, University of Mainz, Germany (Oct. 2014).

McCormick, U., et al., "Diagnosis and Treatment of Patients With Bipolar Disorder: a Review for Advanced Practice Nurses," Journal of the American Association of Nurse Practitioners, 27(9):530-542, Wolters Kluwer, United States (Sep. 2015).

McGrath J., et al., "Schizophrenia: a Concise Overview of Incidence, Prevalence, and Mortality," Epidemiologic Reviews, 30:67-76, Oxford University Press on Behalf of Johns Hopkins Bloomberg School of Public Health, United States (2008).

McIntyre R.S and Wong R., "Asenapine: a Synthesis of Efficacy Data in Bipolar Mania and Schizophrenia," Clinical Schizophrenia & Related Psychoses, 5 (4):217-220, Walsh Medical Media, United States (Jan. 2012).

McIntyre, R.S., et al., "A 3-week, Randomized, Placebo-controlled Trial of Asenapine in the Treatment of Acute Mania in Bipolar Mania and Mixed States," Bipolar Disorder, 11(7):1-15, Wiley-Blackwell Munksgaard, Denmark, (Nov. 2009).

McIntyre, R.S., et al., "Asenapine in the Treatment of Acute Mania in Bipolar I Disorder: a Randomized, Double-blind, Placebo-controlled Trial," Journal of Affective Disorders, 122(1-2):27-38, Elsevier/North-Holland Biomedical Press, Netherlands (Apr. 2010).

Meltzer, H.Y., "Chapter 58: Mechanism of Action of Atypical Antipsychotic Drugs," 2002, 14 pages.

Merikangas K.R., et al., "Lifetime and 12-month Prevalence of Bipolar Spectrum Disorder in the National Comorbidity Survey Replication," Archives of General Psychiatry, 64 (5):543-552, American Medical Association, United States (May 2007).

Merikangas K.R., et al., "Prevalence and Correlates of Bipolar Spectrum Disorder in the World Mental Health Survey Initiative," Archives of General Psychiatry, 68 (3):241-251, American Medical Association, United States (Mar. 2011).

Meyer J.M., "Understanding Depot Antipsychotics: an Illustrated Guide to Kinetics," CNS Spectrums, 18 (Suppl 1):58-67, Cambridge University Press, United Kingdom (Dec. 2013).

Minassian A and Young J.W., "Evaluation of the Clinical Efficacy of Asenapine in Schizophrenia," Expert Opinion on Pharmacotherapy, 11 (12):2107-2115, Informa Healthcare, United Kingdom (Aug. 2010).

Miyake, N., et al., "New Serotonin/Dopamine Antagonists for the Treatment of Schizophrenia," Clinical Schizophrenia & Related Psychoses, 6(3):122-133, (Oct. 2012).

Mura G., et al., "Schizophrenia: from Epidemiology to Rehabilitation," Clinical Practice and Epidemiology in Mental Health: CP & EMH, 8:52-66, Bentham Open, United Arab Emirates, (2012).

"Sycrest® (Asenapin)," Neue Arzneimittel, 2011, 2 pages.

Nivoli A.M., et al., "New Treatment Guidelines for Acute Bipolar Mania: a Critical Review," Journal of Affective Disorders, 140 (2):125-141, Elsevier/North-Holland Biomedical Press, Netherlands (Oct. 2012).

Office Action dated Aug. 15, 2019, in U.S. Appl. No. 15/847,360, inventor Mohr, Patrick et al., filed Dec. 19, 2017, 20 pages.

Peeters, P., et al., "Asenapine Pharmacokinetics in Hepatic and Renal Impairment," Clinical Pharmacokinetics, 50(7):471-481, Adis, part of Springer Science+Business Media, Switzerland (Jul. 2011).

"5.5 Pharmacokinetics—Sublingual: 5.5.1 Single Dose Pharmacokinetics," 2008, 279 pages.

Piccitioni, M.M., "Schizophrenia," The BMJ 335:91-95, Clinical Review (Jul. 2007).

Pompili M., et al., "The Role of Asenapine in the Treatment of Manic or Mixed States Associated With Bipolar I Disorder," Neuropsychiatric Disease and Treatment, 7:259-265, Dove Medical Press, New Zealand (2011).

Potkin, S., et al., "Asenapine in Schizophrenia: an Overview of Clinical Trials in the Olympia Program," Schizophrenia Research, 102(1):258-258, Elsevier B.V., Netherlands (Jun. 2008).

Potkin S.G., et al., "Efficacy and Tolerability of Asenapine in Acute Schizophrenia: a Placebo- and Risperidone-controlled Trial," The Journal of Clinical Psychiatry, 68(10):1492-1500, Physicians Postgraduate Press, United States (Oct. 2007).

Potkin, S.G., et al., "Long-term Effects of Asenapine or Olanzapine in Patients With Persistent Negative Symptoms of Schizophrenia: a Pooled Analysis," Schizophrenia Research, 150(2-3):442-449, Elsevier Science Publisher B.V., Netherlands (Nov. 2013).

Rado, J and Janicak, P.G, "Pharmacological and Clinical Profile of Recently Approved Second-generation Antipsychotics: Implications for Treatment of Schizophrenia in Older Patients," Drugs Aging, 29(10):783-791, Springer International, New Zealand (Oct. 2012).

"Receptor Binding Profiles of Atypical Antipsychotics: Mechanisms of Therapeutic Actions and Adverse Side Effects," Presented at the 2012 NEI Global Psychopharmacology Congress, 1 page.

Regier D.A., et al., "The De Facto Us Mental and Addictive Disorders Service System. Epidemiologic Catchment Area Prospective 1-year Prevalence Rates of Disorders and Services," Archives of General Psychiatry, 50 (2):85-94, American Medical Association, United States (Feb. 1993).

(56) References Cited

OTHER PUBLICATIONS

Reynolds G.P., "Receptor Mechanisms of Antipsychotic Drug Action in Bipolar Disorder—Focus on Asenapine," Therapeutic Advances in Psychopharmacology, 1 (6):197-204, Sage, United Kingdom (Dec. 2011).
Ross, C.A., et al., "Neurobiology of Schizophrenia," Neuron, 52(1):139-153, Cell Press, United States (Oct. 2006).
"Product Information SAPHRIS® (asenapine maleate)," 25 pages.
"SAPHRIS® (asenapine) 2.5 mg Sublingual Tablets for the Acute Treatment of Manic or Mixed Episodes of Bipolar I Disorder in Pediatric Patients (ages 10-17) Now Available in Pharmacies throughout the U.S," accessed from PRNewswire, 2015, 8 pages.
Saphris (asenapine) Sublingual Tablets, Jul. 30, 2009 PDAC, Briefing Book, vol. 1, U.S. Food and Drug Administration, 1068 Pages.
"Product Monograph SAPHRIS® (asenapine sublingual tablets)—Antypsychotic," 2016, 49 Pages.
Sawyer, L., et al., "Cost-effectiveness of Asenapine in the Treatment of Bipolar I Disorder Patients With Mixed Episodes," Journal of Medical Economics, 17(7):508-519, Taylor & Francis, United Kingdom (Jul. 2014).
Scheidemantel, T., et al., "Asenapine for Bipolar Disorder," Neuropsychiatric Disease and Treatment, 11:3007-3017, Dove Medical Press, New Zealand (2015).
"Schizophrenia: Core Interventions in the Treatment and Management of Schizophrenia in Adults in Primary and Secondary Care (update)," NICE guideline, Draft for consultation, Sep. 2008, 39 Pages.
Schoemaker, J., et al., "Long-Term Assessment of Asenapine vs. Olanzapine in Patients with Schizoaffective Disorder," Pharmacopsychiatry, 43(4):e1-e10, Georg Thieme Verlag KG, Germany (2010).
Shahid, M., et al., "Asenapine: a Novel Psychopharmacologic Agent With a Unique Human Receptor Signature," Journal of Psychopharmacology, 23(1):2 pages, Sage Publications, United States (Feb. 2008).
Shreya, A.B., et al., "Nano-transfersomal Formulations for Transdermal Delivery of Asenapine Maleate: in Vitro and in Vivo Performance Evaluations," Journal of Liposome Research, 26(3):221-232, Informa Healthcare, United Kingdom (Sep. 2016).
Simeone J.C., et al., "An Evaluation of Variation in Published Estimates of Schizophrenia Prevalence From 1990-2013: A Systematic Literature Review," BMC Psychiatry, 15:193, BioMed Central, United Kingdom (Aug. 2015).
Smith E.N., et al., "Asenapine Augmentation and Treatment-resistant Schizophrenia in the High-secure Hospital Setting," Therapeutic Advances in Psychopharmacology, 4 (5):193-197, Sage, United Kingdom (Oct. 2014).
Smyth A.M., et al., "The Neuroimmunology of Schizophrenia," Clinical Psychopharmacology and Neuroscience, 11(3):107-117, Korean College of Neuropsychopharmacology, Korea, (Dec. 2013).
"Steltenwert Von Asenapin (Sycrest®) in Der Behandlung Von Bipolaren Storungen—Clinical Experience Program (CEP): Erste Praktische Erfahrungen in Der Schweiz," Aug. 2013, 12 pages.
"Sycrest® 10 mg Sublingualtabletten," Fachinformation (zusammenfassung der merkmale des arzneimittels, 2012, 6 pages.
Szegedi A., et al., "Effects of Asenapine on Depressive Symptoms in Patients With Bipolar I Disorder Experiencing Acute Manic or Mixed Episodes: a Post Hoc Analysis of Two 3-week Clinical Trials," BMC Psychiatry, 11:101, BioMed Central, United Kingdom (Jun. 2011).
Tarazi, F.I and Stahl, S.M, "Iloperidone, Asenapine and Lurasidone: a Primer on Their Current Status," Expert Opinion on Pharmacotherapy, 13(13):1911-1922, Informa Healthcare, United Kingdom (Sep. 2012).
Tiihonen J., et al., "11-year Follow-up of Mortality in Patients With Schizophrenia: a Population-based Cohort Study (Fin11 Study)," Lancet (London, United Kingdom), 374 (9690):620-627, Elsevier, United Kingdom (Aug. 2009).
Van De Wetering-Krebbers S.F., et al., "Metabolism and Excretion of Asenapine in Healthy Male Subjects," Drug Metabolism and Disposition: the Biological Fate of Chemicals, 39 (4):580-590, American Society for Pharmacology and Experimental Therapeutics, United States (Apr. 2011).
Weber, J and Mccormack, P.L, "Asenapine," CNS Drugs, 23(9):781-792, Springer, Germany (Sep. 2009).
"Zusammenfassung Der Merkmale Des Arzneimittels," 1 Anhang I, 2010, 44 pages.
Office Action dated Jan. 31, 2020, in U.S. Appl. No. 15/847,360, inventor Mohr, Patrick et al., filed Dec. 19, 2017, 22 pages.
Office Action dated Sep. 20, 2019, in U.S. Appl. No. 16/445,582, inventor Mohr, Patrick et al., filed Jun. 19, 2019, 15 pages.
Office Action dated Feb. 20, 2020, in U.S. Appl. No. 16/445,582, inventor Mohr, Patrick et al., filed Jun. 19, 2019, 25 pages.
Office Action dated Jul. 8, 2020, in U.S. Appl. No. 16/445,582, inventor Mohr, Patrick et al., filed Jun. 19, 2019, 25 pages.
Office Action dated Sep. 2, 2020, in U.S. Appl. No. 16/445,582, inventor Mohr, Patrick et al., filed Jun. 19, 2019, 34 pages.
Office Action dated Jun. 9, 2020, in U.S. Appl. No. 16/788,128, inventor Mohr, Patrick et al., filed Feb. 11, 2020, 18 pages.
Office Action dated Aug. 19, 2020, in U.S. Appl. No. 16/788,128, inventor Mohr, Patrick et al., filed Feb. 11, 2020, 26 pages.
Co-pending U.S. Appl. No. 17/250,162, inventors Mohr, P., et al., International filing date: Jun. 19, 2019 (Not Published).
Co-pending U.S. Appl. No. 17/250,163, inventors Mohr, P., et al., International filing date: Jun. 19, 2019 (Not Published).

* cited by examiner

TRANSDERMAL THERAPEUTIC SYSTEM CONTAINING ASENAPINE AND SILICONE ACRYLIC HYBRID POLYMER

TECHNICAL FIELD OF THE INVENTION

The present invention relates to a transdermal therapeutic system (TTS) for the transdermal administration of asenapine to the systemic circulation, and processes of manufacture, method of treatments and uses thereof.

BACKGROUND OF THE INVENTION

The active agent asenapine (3aRS,12bRS)-rel-5-chloro-2,3,3a,12b-tetrahydro-2-methyl-1H-dibenz[2,3:6,7]oxepino[4,5-c]pyrrole) is an atypical antipsychotic belonging to the dibenzo-oxepino pyrrole family, the tetracyclic structure of which is unrelated to those of other antipsychotics such as Olanzapine, Quetiapine or Clozapine (tricyclic structure), Risperidone, Ziprasidone or Aripiprazole (bicyclic structure). Asenapine is an antagonist at the dopamine D2 and serotonin 5-HT2A receptors with high affinity to the latter and has been developed by Schering-Plough/Organon for the treatment of schizophrenia and acute mania associated with bipolar disorder.

Currently, asenapine is commercially available in the form of sublingual tablets, which is administered in dosage strengths of 5 mg or 10 mg twice daily (BID) under the brand names Sycrest (Swissmedic) and Saphris (Schering-Plough).

The sublingual administration route avoids the first-pass metabolism of an oral administration in order to increase bioavailability, which is at 35% when taken sublingually and <2% if ingested. However, sublingual administration is associated with bitter or unpleasant taste as well as tongue/oral mucosal numbness induced by a local anesthetic effect, nausea and headaches. Further, eating, drinking and smoking are not allowed immediately after sublingual dosing. These inconveniences may lead to reduced patient compliance and improper administration such as dose reduction, dose skipping, irregular drug intake or a complete abstinence from the intended asenapine intake. Sublingual administration is also difficult to monitor in institutionalized psychiatric patients and may not be suitable for children, elderly and other patients with difficulty in swallowing, or for those not capable of taking medication on their own.

Following sublingual administration, asenapine is rapidly absorbed with peak blood plasma concentrations occurring within 0.5 to 1.5 hours and (in therapeutic doses) exhibits 2-compartment pharmacokinetics with a rapid initial distribution phase with a half-life of several hours, followed by a longer terminal disposition half-life of around 1 day or longer. The blood plasma concentration thus exhibits a certain degree of fluctuation with peaks about 1 hour post-dose, followed by a concentration decrease resulting in a low point just before the next dose, even in steady state. The relatively rapid concentration decrease also inevitably leads to multiple daily doses (currently twice daily), which are associated with poor patient compliance, in particular in chronic conditions.

Such fluctuation could be avoided, or at least reduced by transdermal administration of asenapine, which prevents plasma concentration decrease between two doses to some extent by providing an extended release of the active. Transdermal delivery of asenapine has been investigated, but it appears that passive transdermal delivery of asenapine, and in particular a constant release over an extended period of time, is challenging. Passive transport of active agents from a transdermal therapeutic system (TTS) through the skin makes use of the driving force based on the concentration gradient between the concentration of active agent in the transdermal system and on the outer surface of the skin and the concentration in the blood stream. Such passive transport is advantageous in view of complexity of the TTS and the convenience of administration compared to TTS making use of active transportation such as iontophoresis or microporation. Up to date, no commercial asenapine TTS is available.

There is thus a need in the art for a transdermal therapeutic system for the transdermal administration of asenapine.

OBJECTS AND SUMMARY OF THE INVENTION

It is an object of the present invention to provide a TTS overcoming the above-mentioned disadvantages of current asenapine administration.

Thus, it is an object of the present invention to provide a TTS for the transdermal administration of asenapine providing a permeation rate which is sufficient for achieving a therapeutically effective dose. In particular, it is an object of the present invention to provide a matrix-type TTS for the transdermal administration of asenapine providing a permeation rate which is sufficient for achieving a therapeutically effective dose.

It is a further object of the present invention to provide a TTS for the transdermal administration of asenapine, having an asenapine-containing layer structure of low complexity, which is consequently advantageous in terms of the costs for the manufacture.

It is a further object of the present invention to provide a TTS for the transdermal administration of asenapine, wherein a constant release over an extended period of time is provided.

It is a further object of the present invention to provide a TTS for the transdermal administration of asenapine in a continuous administration, providing therapeutically effective amounts of asenapine for up to 7 days, during an administration period to the skin of the patient of up to 7 days (e.g. 3.5 days).

It is also an object of the present invention to provide a TTS for the transdermal administration of asenapine, wherein the fluctuation in asenapine blood plasma concentration is reduced when compared to sublingual administration, in particular in steady state.

It is another object of the present invention to provide a TTS for the transdermal administration of asenapine which complies with the needs of a convenient application in view of size and thickness and/or which is easy and cost-efficient to manufacture.

It is an object of certain embodiments of the present invention to provide a TTS for the transdermal administration of asenapine with an improved bioavailability of asenapine.

It is an object of certain embodiments of the present invention to provide a TTS for the transdermal administration of asenapine, wherein therapeutically effective amounts of asenapine are provided for 1 day by said transdermal therapeutic system during an administration period to the skin of the patient of 1 day, allowing a once a day exchange of the TTS in an around the clock treatment.

It is an object of certain embodiments of the present invention to provide a TTS for the transdermal administration of asenapine, wherein therapeutically effective amounts of asenapine are provided for 3.5 days by said transdermal therapeutic system during an administration period to the skin of the patient of 3.5 days, allowing a twice a week exchange of the TTS in an around the clock treatment.

It is an object of certain embodiments of the present invention to provide a TTS for the transdermal administration of asenapine, wherein therapeutically effective amounts of asenapine are provided for 7 days by said transdermal therapeutic system during an administration period to the skin of the patient of 7 days, allowing a once a week exchange of the TTS in an around the clock treatment.

These objects and others are accomplished by the present invention, which according to one first aspect relates to a transdermal therapeutic system for the transdermal administration of asenapine comprising an asenapine-containing layer structure, said asenapine-containing layer structure comprising:
A) a backing layer; and
B) an asenapine-containing layer;
wherein the transdermal therapeutically system comprises a silicone acrylic hybrid polymer.

According to a second aspect, the present invention relates to a transdermal therapeutic system for the transdermal administration of asenapine comprising an asenapine-containing layer, said asenapine-containing layer structure comprising:
A) a backing layer; and
B) an asenapine-containing layer comprising
1. asenapine; and
2. a silicone acrylic hybrid polymer.

According to a third aspect, the present invention relates to a transdermal therapeutic system for the transdermal administration of asenapine comprising an asenapine-containing self-adhesive layer structure comprising:
A) a backing layer; and
B) an asenapine-containing pressure-sensitive adhesive layer comprising:
1. asenapine included in the form of the free base in an amount of from 4% to 10% of the asenapine-containing pressure-sensitive adhesive layer; and
2. a silicone acrylic hybrid pressure-sensitive adhesive in an amount of from 90 to 96% of the asenapine-containing pressure-sensitive adhesive layer;
wherein the area weight of the asenapine-containing pressure-sensitive adhesive layer ranges from 90 to 160 g/m².

According to a fourth aspect, the present invention relates to a transdermal therapeutic system for the transdermal administration of asenapine comprising an asenapine-containing self-adhesive layer structure comprising:
A) a backing layer;
B) an asenapine-containing pressure-sensitive adhesive layer comprising:
1. asenapine included in the form of the free base in an amount of from 10% to 17% of the asenapine-containing pressure-sensitive adhesive layer; and
2. a silicone acrylic hybrid pressure-sensitive adhesive in an amount of from 83 to 90% of the asenapine-containing pressure-sensitive adhesive layer;
wherein the area weight of the asenapine-containing pressure-sensitive adhesive layer ranges from 90 to 160 g/m².

According to yet another aspect, the invention relates to a process for manufacturing an asenapine-containing layer for use in a transdermal therapeutic system according to the present invention comprising the steps of:
1) combining at least the components asenapine and a silicone acrylic hybrid polymer in a solvent to obtain a coating composition;
2) coating the coating composition onto the backing layer or release liner; and
3) drying the coated coating composition to form the asenapine-containing layer.

Definitions

Within the meaning of this invention, the term "transdermal therapeutic system" (TTS) refers to a system by which the active agent (e.g. asenapine) is administered to the systemic circulation via transdermal delivery and refers to the entire individual dosing unit that is applied, after removing an optionally present release liner, to the skin of a patient, and which comprises a therapeutically effective amount of active agent in an active agent-containing layer structure and optionally an additional adhesive overlay on top of the active agent-containing layer structure. The active agent-containing layer structure may be located on a release liner (a detachable protective layer), thus, the TTS may further comprise a release liner. Within the meaning of this invention, the term "TTS" in particular refers to systems providing transdermal delivery, excluding active delivery for example via iontophoresis or microporation. Transdermal therapeutic systems may also be referred to as transdermal drug delivery systems (TDDS) or transdermal delivery systems (TDS).

Within the meaning of this invention, the term "asenapine-containing layer structure" refers to the layer structure containing a therapeutically effective amount of asenapine and comprises a backing layer and at least one active agent-containing layer. Preferably, the asenapine-containing layer structure is an asenapine-containing self-adhesive layer structure.

Within the meaning of this invention, the term "therapeutically effective amount" refers to a quantity of asenapine in the TTS sufficient to provide, if administered by the TTS to a patient, asenapine blood levels of a similar range (e.g. of about 10% to about 1000% as measured as an AUC) when compared to blood levels obtained in steady state administration of twice daily 5 mg sublingual asenapine over a predefined extended period of time (e.g. 1, 3.5 and 7 days). A TTS usually contains more active in the system than is in fact provided to the skin and the systemic circulation. This excess amount of active agent is usually necessary to provide enough driving force for the delivery from the TTS to the systemic circulation.

Within the meaning of this invention, the terms "active", "active agent", and the like, as well as the term "asenapine" refer to asenapine in any pharmaceutically acceptable chemical and morphological form and physical state. These forms include without limitation asenapine in its free base form, protonated or partially protonated asenapine, asenapine salts, cocrystals and in particular acid addition salts formed by addition of an inorganic or organic acid such as asenapine hydrochloride or asenapine maleate, solvates, hydrates, clathrates, complexes and so on, as well as asenapine in the form of particles which may be micronized, crystalline and/or amorphous, and any mixtures of the aforementioned forms. The asenapine, where contained in a medium such as a solvent, may be dissolved or dispersed or in part dissolved and in part dispersed.

When asenapine is mentioned to be used in a particular form in the manufacture of the TTS, this does not exclude interactions between this form of asenapine and other ingredients of the asenapine-containing layer structure, e.g. salt formation or complexation, in the final TTS. This means that, even if asenapine is included in its free base form, it may be present in the final TTS in protonated or partially protonated form or in the form of an acid addition salt, or, if it is included in the form of a salt, parts of it may be present as free base in the final TTS. Unless otherwise indicated, in particular the amount of asenapine in the layer structure relates to the amount of asenapine included in the TTS during manufacture of the TTS and is calculated based on asenapine in the form of the free base. E.g., when a) 0.1 mmol (equal to 28.6 mg) asenapine base or b) 0.1 mmol (equal to 40.2 mg) asenapine maleate is included in the TTS during manufacture, the amount of asenapine in the layer structure is, within the meaning of the invention, in both cases 0.1 mmol or 28.6 mg.

The asenapine starting material included in the TTS during manufacture of the TTS may be in the form of particles. Asenapine may e.g. be present in the active agent-containing layer structure in the form of particles and/or dissolved.

Within the meaning of this invention, the term "particles" refers to a solid, particulate material comprising individual particles, the dimensions of which are negligible compared to the material. In particular, the particles are solid, including plastic/deformable solids, including amorphous and crystalline materials.

Within the meaning of this invention, the term "dispersing" refers to a step or a combination of steps wherein a starting material (e.g. asenapine) is not totally dissolved. Dispersing in the sense of the invention comprises the dissolution of a part of the starting material (e.g. asenapine particles), depending on the solubility of the starting material (e.g. the solubility of asenapine in the coating composition).

There are two main types of TTS for active agent delivery, i.e. matrix-type TTS and reservoir-type TTS. The release of the active agent in a matrix-type TTS is mainly controlled by the matrix including the active agent itself. In contrast thereto, a reservoir-type TTS typically needs a rate-controlling membrane controlling the release of the active agent. In principle, also a matrix-type TTS may contain a rate-controlling membrane. However, matrix-type TTS are advantageous in that, compared to reservoir-type TTS, usually no rate determining membranes are necessary and no dose dumping can occur due to membrane rupture. In summary, matrix-type transdermal therapeutic systems (TTS) are less complex in manufacture and easy and convenient to use by patients.

Within the meaning of this invention, "matrix-type TTS" refers to a system or structure wherein the active is homogeneously dissolved and/or dispersed within a polymeric carrier, i.e. the matrix, which forms with the active agent and optionally remaining ingredients a matrix layer. In such a system, the matrix layer controls the release of the active agent from the TTS. Preferably, the matrix layer has sufficient cohesion to be self-supporting so that no sealing between other layers is required. Accordingly, the active agent-containing layer may in one embodiment of the invention be an active agent-containing matrix layer, wherein the active agent is homogeneously distributed within a polymer matrix. In certain embodiments, the active agent-containing matrix layer may comprise two active agent-containing matrix layers, which may be laminated together. Matrix-type TTS may in particular be in the form of a "drug-in-adhesive"-type TTS referring to a system wherein the active is homogeneously dissolved and/or dispersed within a pressure-sensitive adhesive matrix. In this connection, the active agent-containing matrix layer may also be referred to as active agent-containing pressure sensitive adhesive layer or active agent-containing pressure sensitive adhesive matrix layer. A TTS comprising the active agent dissolved and/or dispersed within a polymeric gel, e.g. a hydrogel, is also considered to be of matrix-type in accordance with present invention.

TTS with a liquid active agent-containing reservoir are referred to by the term "reservoir-type TTS". In such a system, the release of the active agent is preferably controlled by a rate-controlling membrane. In particular, the reservoir is sealed between the backing layer and the rate-controlling membrane. Accordingly, the active agent-containing layer may in one embodiment be an active agent-containing reservoir layer, which preferably comprises a liquid reservoir comprising the active agent. Furthermore, the reservoir-type TTS typically additionally comprises a skin contact layer, wherein the reservoir layer and the skin contact layer may be separated by the rate-controlling membrane. In the reservoir layer, the active agent is preferably dissolved in a solvent such as ethanol or water or in silicone oil. The skin contact layer typically has adhesive properties.

Reservoir-type TTS are not to be understood as being of matrix-type within the meaning of the invention. However, microreservoir TTS (biphasic systems having deposits (e.g. spheres, droplets) of an inner active-containing phase dispersed in an outer polymer phase), considered in the art to be a mixed from of a matrix-type TTS and a reservoir-type TTS that differ from a homogeneous single phase matrix-type TTS and a reservoir-type TTS in the concept of drug transport and drug delivery, are considered to be of matrix-type within the meaning of the invention. The sizes of microreservoir droplets can be determined by an optical microscopic measurement (for example by Leica MZ16 including a camera, for example Leica DSC320) by taking pictures of the microreservoirs at different positions at an enhancement factor between 10 and 400 times, depending on the required limit of detection. By using imaging analysis software, the sizes of the microreservoirs can be determined.

Within the meaning of this invention, the term "asenapine-containing layer" refers to a layer containing the active agent and providing the area of release. The term covers asenapine-containing matrix layers and asenapine-containing reservoir layers. If the asenapine-containing layer is an asenapine-containing matrix layer, said layer is present in a matrix-type TTS. If the polymer is a pressure-sensitive adhesive, the matrix layer may also represent the adhesive layer of the TTS, so that no additional skin contact layer is present. Alternatively, an additional skin contact layer may be present as adhesive layer, and/or an adhesive overlay is provided. The additional skin contact layer is typically manufactured such that it is active agent-free. However, due to the concentration gradient, the active agent will migrate from the matrix layer to the additional skin contact layer over time, until equilibrium is reached. The additional skin contact layer may be present on the asenapine-containing matrix layer or separated from the asenapine-containing matrix layer by a membrane, preferably a rate controlling membrane. Preferably, the asenapine-containing matrix layer has sufficient adhesive properties, so that no additional skin contact layer is present. If the asenapine-containing layer is an asenapine-containing reservoir layer, said layer is present in a reservoir-type TTS, and the layer comprises the asenapine in a liquid reservoir. In addition, an additional skin contact layer is preferably present, in order to provide adhesive properties. Preferably, a rate-controlling membrane separates the reservoir layer from the additional skin contact layer. The additional skin contact layer can be manufactured such that it is active agent-free or active agent-containing. If the additional skin contact layer is free of active agent the active agent will migrate, due to the concentration gradient, from the reservoir layer to the skin contact layer over time, until equilibrium is reached. Additionally an adhesive overlay may be provided.

As used herein, the asenapine-containing layer is preferably an asenapine-containing matrix layer, and it is referred to the final solidified layer. Preferably, an asenapine-containing matrix layer is obtained after coating and drying the solvent-containing coating composition as described herein. Alternatively an asenapine-containing matrix layer is obtained after melt-coating and cooling. The asenapine-containing matrix layer may also be manufactured by laminating two or more such solidified layers (e.g. dried or cooled layers) of the same composition to provide the desired area weight. The matrix layer may be self-adhesive (in the form of a pressure sensitive adhesive matrix layer), or the TTS may comprise an additional skin contact layer of a pressure sensitive adhesive for providing sufficient tack. Preferably, the matrix layer is a pressure sensitive adhesive matrix layer. Optionally, an adhesive overlay may be present.

Within the meaning of this invention, the term "pressure-sensitive adhesive" (also abbreviated as "PSA") refers to a material that in particular adheres with finger pressure, is permanently tacky, exerts a strong holding force and should be removable from smooth surfaces without leaving a residue. A pressure sensitive adhesive layer, when in contact with the skin, is "self-adhesive", i.e. provides adhesion to the skin so that typically no further aid for fixation on the skin is needed. A "self-adhesive" layer structure includes a pressure sensitive adhesive layer for skin contact which may be provided in the form of a pressure sensitive adhesive matrix layer or in the form of an additional layer, i.e. a pressure sensitive adhesive skin contact layer. An adhesive overlay may still be employed to advance adhesion. The pressure-sensitive adhesive properties of a pressure-sensitive adhesive depend on the polymer or polymer composition used.

Within the meaning of this invention, the term "silicone acrylic hybrid polymer" refers to a polymerization product including repeating units of a silicone sub-species and an acrylate-sub species. The silicone acrylic hybrid polymer thus comprises a silicone phase and an acrylic phase. The term "silicone acrylic hybrid" is intended to denote more than a simple blend of a silicone-based sub-species and an acrylate-based sub-species. Instead, the term denotes a polymerized hybrid species that includes silicone-based sub-species and acrylate-based sub-species that have been polymerized together. The silicone acrylic hybrid polymer may also be referred to as a "silicone acrylate hybrid polymer" as the terms acrylate and acrylic are generally used interchangeably in the context of the hybrid polymers used in the present invention.

Within the meaning of this invention, the term "silicone acrylic hybrid pressure-sensitive adhesive" refers to a silicone acrylic hybrid polymer in the form of a pressure-sensitive adhesive. Silicone acrylic hybrid pressure-sensitive adhesives are described, for example, in EP 2 599 847 and WO 2016/130408. Examples of silicone acrylic hybrid pressure-sensitive adhesives include the PSA series 7-6100 and 7-6300 manufactured and supplied in n-heptane or ethyl acetate by Dow Corning (7-610X and 7-630X; X=1 n-heptane-based/X=2 ethyl acetate-based). It was found that, depending on the solvent in which the silicone acrylic hybrid PSA is supplied, the arrangement of the silicone phase and the acrylic phase providing a silicone or acrylic continuous external phase and a corresponding discontinuous internal phase is different. If the silicone acrylic hybrid PSA is supplied in n-heptane, the composition contains a continuous, silicone external phase and a discontinuous, acrylic internal phase. If the silicone acrylic hybrid PSA composition is supplied in ethyl acetate, the composition contains a continuous, acrylic external phase and a discontinuous, silicone internal phase.

Within the meaning of this invention, the term "non-hybrid polymer" is used synonymously for a polymer which does not include a hybrid species. Preferably, the non-hybrid polymer is a pressure-sensitive adhesive (e.g. a silicone- or acrylate-based pressure-sensitive adhesive).

Within the meaning of this invention, the term "silicon-containing pressure-sensitive adhesive composition comprising acrylate or methacrylate functionality" comprises the condensation reaction product of a silicone resin, a silicone polymer, and a silicon-containing capping agent which provides said acrylate or methacrylate functionality. It is to be understood that the silicon-containing pressure-sensitive adhesive composition comprising acrylate or methacrylate functionality can include only acrylate functionality, only methacrylate functionality, or both acrylate functionality and methacrylate functionality.

As used herein, an active agent-containing matrix layer is a layer containing the active agent dissolved or dispersed in at least one polymer, or containing the active agent dissolved in a solvent to form an active agent-solvent mixture that is dispersed in the form of deposits (in particular droplets) in at least one polymer. Preferably, the at least one polymer is a polymer-based pressure-sensitive adhesive (e.g. a silicone acrylic hybrid pressure-sensitive adhesive). Within the meaning of this invention, the term "pressure-sensitive adhesive layer" refers to a pressure-sensitive adhesive layer obtained from a solvent-containing adhesive coating composition after coating on a film and evaporating the solvents.

Within the meaning of this invention, the term "skin contact layer" refers to the layer included in the active agent-containing layer structure to be in direct contact with the skin of the patient during administration. This may be the active agent-containing layer. When the TTS comprises an additional skin contact layer, the other layers of the active agent-containing layer structure do not contact the skin and do not necessarily have self-adhesive properties. As outlined above, an additional skin contact layer attached to the active agent-containing layer may over time absorb parts of the active agent. An additional skin contact layer may be used to enhance adherence. The sizes of an additional skin contact layer and the active agent-containing layer are usually coextensive and correspond to the area of release. However, the area of the additional skin contact layer may also be greater than the area of the active agent-containing layer. In such a case, the area of release still refers to the area of the active agent-containing layer.

Within the meaning of this invention, the term "area weight" refers to the dry weight of a specific layer, e.g. of the asenapine-containing layer, provided in $g/m^2$. The area weight values are subject to a tolerance off 10%, preferably ±7.5%, due to manufacturing variability.

If not indicated otherwise "%" refers to % by weight.

Within the meaning of this invention, the term "polymer" refers to any substance consisting of so-called repeating units obtained by polymerizing one or more monomers, and includes homopolymers which consist of one type of monomer and copolymers which consist of two or more types of monomers. Polymers may be of any architecture such as linear polymers, star polymer, comb polymers, brush polymers, of any monomer arrangements in case of copolymers, e.g. alternating, statistical, block copolymers, or graft polymers. The minimum molecular weight varies depending on the polymer type and is known to the skilled person. Polymers may e.g. have a molecular weight above 2000, preferably above 5000 and more preferably above 10,000 Dalton. Correspondingly, compounds with a molecular weight below 2000, preferably below 5000 or more preferably below 10,000 Dalton are usually referred to as oligomers.

Within the meaning of this invention, the term "cross-linking agent" refers to a substance which is able to cross-link functional groups contained within the polymer.

Within the meaning of this invention, the term "adhesive overlay" refers to a self-adhesive layer structure that is free of active agent and larger in area than the active agent-containing structure and provides additional area adhering to the skin, but no area of release of the active agent. It enhances thereby the overall adhesive properties of the TTS. The adhesive overlay comprises a backing layer that may provide occlusive or non-occlusive properties and an adhesive layer. Preferably, the backing layer of the adhesive overlay provides non-occlusive properties.

Within the meaning of this invention, the term "backing layer" refers to a layer, which supports the active agent-containing layer or forms the backing of the adhesive overlay. At least one backing layer in the TTS and usually the backing layer of the active agent-containing layer is substantially impermeable to the active agent contained in the layer during the period of storage and administration and thus prevents active loss or cross-contamination in accordance with regulatory requirements. Preferably, the backing layer is also occlusive, meaning substantially impermeable to water and water-vapor. Suitable materials for a backing layer include polyethylene terephthalate (PET), polyethylene (PE), ethylene vinyl acetate-copolymer (EVA), polyurethanes, and mixtures thereof. Suitable backing layers are thus for example PET laminates, EVA-PET laminates and PE-PET laminates. Also suitable are woven or non-woven backing materials.

The TTS according to the present invention can be characterized by certain parameters as measured in an in vitro skin permeation test.

The in vitro permeation test is performed in a Franz diffusion cell, with human or animal skin and preferably with dermatomed split-thickness human skin with a thickness of 800 μm and an intact epidermis, and with phosphate buffer pH 5.5 or 7.4 as receptor medium (32° C. with 0.1% saline azide) with or without addition of a maximum of 40 vol-% organic solvent e.g. ethanol, acetonitrile, isopropanol, dipropylenglycol, PEG 400 so that a receptor medium may e.g. contain 60 vol-% phosphate buffer pH 5.5, 30 vol-% dipropylenglycol and 10 vol-% acetonitrile.

Where not otherwise indicated, the in vitro permeation test is performed with dermatomed split-thickness human skin with a thickness of 800 μm and an intact epidermis, and with phosphate buffer pH 5.5 as receptor medium (32° C. with 0.1% saline azide). The amount of active permeated into the receptor medium is determined in regular intervals using a validated HPLC method with a UV photometric detector by taking a sample volume. The receptor medium is completely or in part replaced by fresh medium when taking the sample volume, and the measured amount of active permeated relates to the amount permeated between the two last sampling points and not the total amount permeated so far.

Thus, within the meaning of this invention, the parameter "permeated amount" is provided in $\mu g/cm^2$ and relates to the amount of active permeated in a sample interval at certain elapsed time. E.g., in an in vitro permeation test as described above, wherein the amount of active permeated into the receptor medium has been e.g. measured at hours 0, 2, 4, 8, 12 and 24, the "permeated amount" of active can be given e.g. for the sample interval from hour 8 to hour 12 and corresponds to the measurement at hour 12, wherein the receptor medium has been exchanged completely at hour 8.

The permeated amount can also be given as a "cumulative permeated amount", corresponding to the cumulated amount of active permeated at a certain point in time. E.g., in an in vitro permeation test as described above, wherein the amount of active permeated into the receptor medium has been e.g. measured at hours 0, 2, 4, 8, 12 and 24, the "cumulative permeated amount" of active at hour 12 corresponds to the sum of the permeated amounts from hour 0 to hour 2, hour 2 to hour 4, hour 4 to hour 8 and hour 8 to hour 12.

Within the meaning of this invention, the parameter "skin permeation rate" for a certain sample interval at certain elapsed time is provided in $\mu g/cm^2$-hr and is calculated from the permeated amount in said sample interval as measured by in vitro permeation test as described above in $\mu g/cm^2$, divided by the hours of said sample interval. E.g. the skin permeation rate in an in vitro permeation test as described above, wherein the amount of active permeated into the receptor medium has been e.g. measured at hours 0, 2, 4, 8, 12 and 24, the "skin permeation rate" at hour 12 is calculated as the permeated amount in the sample interval from hour 8 to hour 12 divided by 4 hours.

A "cumulative skin permeation rate" can be calculated from the respective cumulative permeated amount by dividing the cumulative permeated amount by the elapsed time. E.g. in an in vitro permeation test as described above, wherein the amount of active permeated into the receptor medium has been e.g. measured at hours 0, 2, 4, 8, 12 and 24, the "cumulative skin permeation rate" at hour 12 is calculated as the cumulative permeated amount for hour 12 (see above) divided by 12 hours.

Within the meaning of this invention, the above parameters "permeated amount" and "skin permeation rate" (as well as "cumulative permeated amount" and "cumulative skin permeation rate") refer to mean values calculated from at least 2, preferably at least 3 in vitro permeation test experiments. Where not otherwise indicated, the standard deviation (SD) of these mean values refer to a corrected sample standard deviation, calculated using the formula:

$$SD = \sqrt{\frac{1}{n-1}\sum_{i=1}^{n}(x_i - \bar{x})^2}$$

wherein n is the sample size, $\{x_1, x_2, \ldots x_n\}$ are the observed values and $\bar{x}$ is the mean value of the observed values.

The TTS according to the present invention can also be characterized by certain parameters as measured in an in vivo clinical study.

Within the meaning of this invention, the parameter "mean release rate" refers to the mean release rate in μg/hr or in mg/day over the period of administration (e.g., 1 to 7 days) by which the active agent is released through the human skin into the systemic circulation and is based on the AUC obtained over said period of administration in a clinical study.

Within the meaning of this invention, the term "extended period of time" relates to a period of at least or about 24 hours, at least or about 48 hours, at least or about 84 hours, at least or about 168 hours, at least or about 1 day, at least or about 3.5 days, or at least or about 7 days, or to a period of about 24 hours to about 168 hours or 1 to 7 day(s), or about 24 hours to about 84 hours or 1 to 3.5 day(s).

For a continuous drug treatment, the frequency of drug administration is preferably kept sufficiently high so as to maintain therapeutically effective blood plasma concentration. In other words, the interval between two dosage form administrations, also called dosing interval, needs to be adapted accordingly. Within the meaning of the present invention, the term "dosing interval" refers to the period of time between two consecutive TTS administrations, i.e. the interval between two consecutive points in time a TTS is applied to the skin of the patient. Once applied, the TTS is usually maintained on the skin of the patient for the entire dosing interval and only removed at the end of the dosing interval, at which time a new TTS is applied to the skin. E.g., if the dosing interval is 168 hours or 7 days, the TTS is applied to and maintained on the skin of the patient for 168 hours or 7 days. After 168 hours or 7 days, the TTS is removed from the skin and a new TTS is applied. Thus, a dosing interval of 168 hours or 7 days allows a once-a-week TTS exchange mode in an around-the-clock treatment.

Within the meaning of this invention, the term "room temperature" refers to the unmodified temperature found indoors in the laboratory where the experiments are conducted and usually lies within 15 to 35° C., preferably about 18 to 25° C.

Within the meaning of this invention, the term "patient" refers to a subject who has presented a clinical manifestation of a particular symptom or symptoms suggesting the need for treatment, who is treated preventatively or prophylactically for a condition, or who has been diagnosed with a condition to be treated.

Within the meaning of this invention the term "pharmacokinetic parameters" refers to parameters describing the blood plasma curve, e.g. $C_{max}$, $C_t$ and $AUC_{t1-t2}$ obtained in a clinical study, e.g. by single-dose, multi-dose or steady state administration of the active agent-containing TTS, e.g. the asenapine TTS to healthy human subjects. The pharmacokinetic parameters of the individual subjects are summarized using arithmetic and geometric means, e.g. a mean $C_{max}$, a mean AUCt and a mean AUCINF, and additional statistics such as the respective standard deviations and standard errors, the minimum value, the maximum value, and the middle value when the list of values is ranked (Median). In the context of the present invention, pharmacokinetic parameters, e.g. the $C_{max}$, $C_t$ and $AUC_{t1-t2}$ refer to geometric mean values if not indicated otherwise. It cannot be precluded that the absolute mean values obtained for a certain TTS in a clinical study vary to a certain extent from study to study. To allow a comparison of absolute mean values between studies, a reference formulation, e.g. in the future any product based on the invention, may be used as internal standard. A comparison of the AUC per area of release of the respective reference product in the earlier and later study can be used to obtain a correction factor to take into account differences from study to study.

Clinical studies according to the present invention refer to studies performed in full compliance with the International Conference for Harmonization of Clinical Trials (ICH) and all applicable local Good Clinical Practices (GCP) and regulations.

Within the meaning of this invention, the term "healthy human subject" refers to a male or female subject with a body weight ranging from 55 kg to 100 kg and a body mass index (BMI) ranging from 18 to 29.4 and normal physiological parameters, such as blood pressure, etc. Healthy human subjects for the purposes of the present invention are selected according to inclusion and exclusion criteria which are based on and in accordance with recommendations of the ICH.

Within the meaning of this invention, the term "subject population" refers to at least five, preferably at least ten individual healthy human subjects.

Within the meaning of this invention, the term "geometric mean" refers to the mean of the log transformed data back-transformed to the original scale.

Within the meaning of this invention, the term "arithmetic mean" refers to the sum of all values of observation divided by the total number of observations.

Within the meaning of this invention, the parameter "AUC" corresponds to the area under the plasma concentration-time curve. The AUC value is proportional to the amount of active agent absorbed into the blood circulation in total and is hence a measure for the bioavailability.

Within the meaning of this invention, the parameter "$AUC_{t1-t2}$" is provided in (ng/ml) hr and relates to the area under the plasma concentration-time curve from hour t1 to t2 and is calculated by the linear trapezoidal method, unless otherwise indicated. Other calculation methods are e.g. the logarithmic and linear log trapezoidal method.

Within the meaning of this invention, the parameter "$C_{max}$" is provided in (ng/ml) and relates to the maximum observed blood plasma concentration of the active agent.

Within the meaning of this invention, the parameter "$C_t$" is provided in (ng/ml) and relates to the blood plasma concentration of the active agent observed at hour t.

Within the meaning of this invention, the parameter "$t_{max}$" is provided in hr and relates to the time point at which the $C_{max}$ value is reached. In other words, $t_{max}$ is the time point of the maximum observed plasma concentration.

Within the meaning of this invention, the term "mean plasma concentration" is provided in (ng/ml) and is a mean of the individual plasma concentrations of active agent, e.g. asenapine, at each point in time.

Within the meaning of this invention, the term "coating composition" refers to a composition comprising all components of the matrix layer in a solvent, which may be coated onto the backing layer or release liner to form the matrix layer upon drying.

Within the meaning of this invention, the term "pressure sensitive adhesive composition" refers to a pressure sensitive adhesive at least in mixture with a solvent (e.g. n-heptane or ethyl acetate).

Within the meaning of this invention, the term "dissolve" refers to the process of obtaining a solution, which is clear and does not contain any particles, as visible to the naked eye.

Within the meaning of this invention, the term "solvent" refers to any liquid substance, which preferably is a volatile organic liquid such as methanol, ethanol, isopropanol, acetone, ethyl acetate, methylene chloride, hexane, n-heptane, toluene and mixtures thereof.

BRIEF DESCRIPTION OF THE D WINGS

Figure 2A:
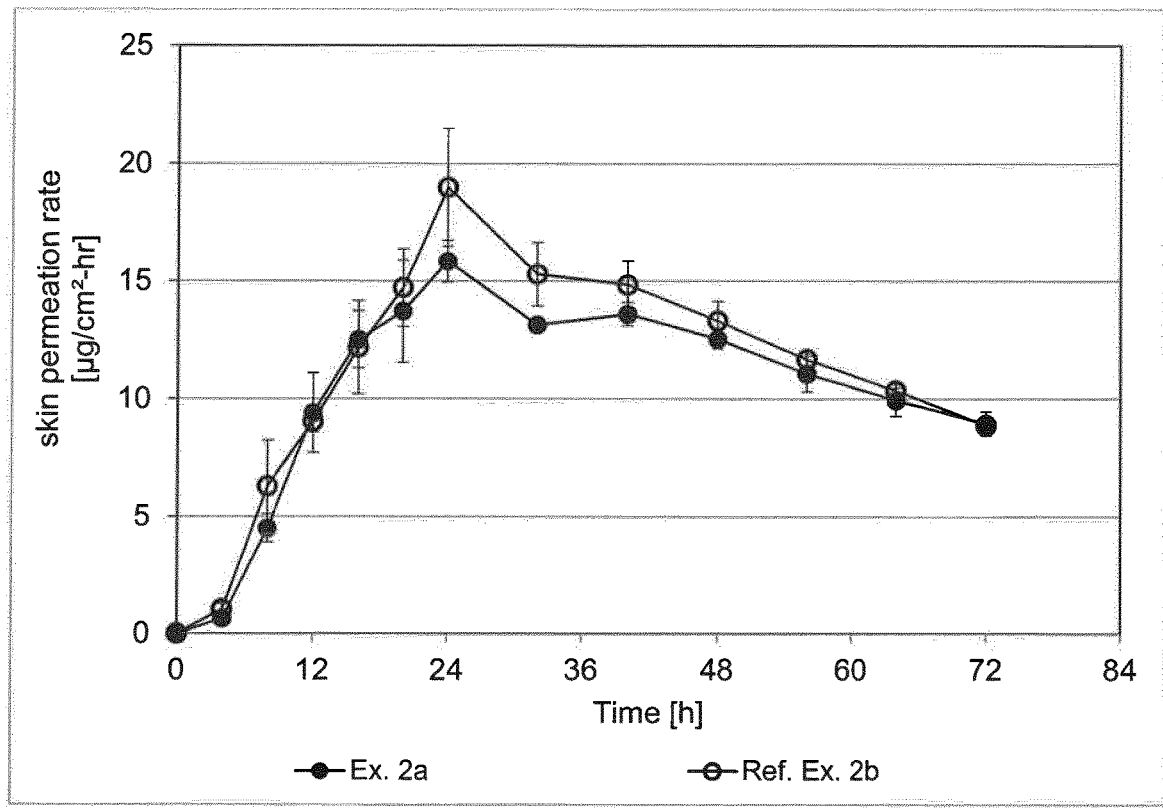
FIG. 2a depicts the asenapine skin permeation rate of TTS prepared according to Ex. 2a and Ref. Ex. 2b for hours 0 to 72.
Figure 2B:
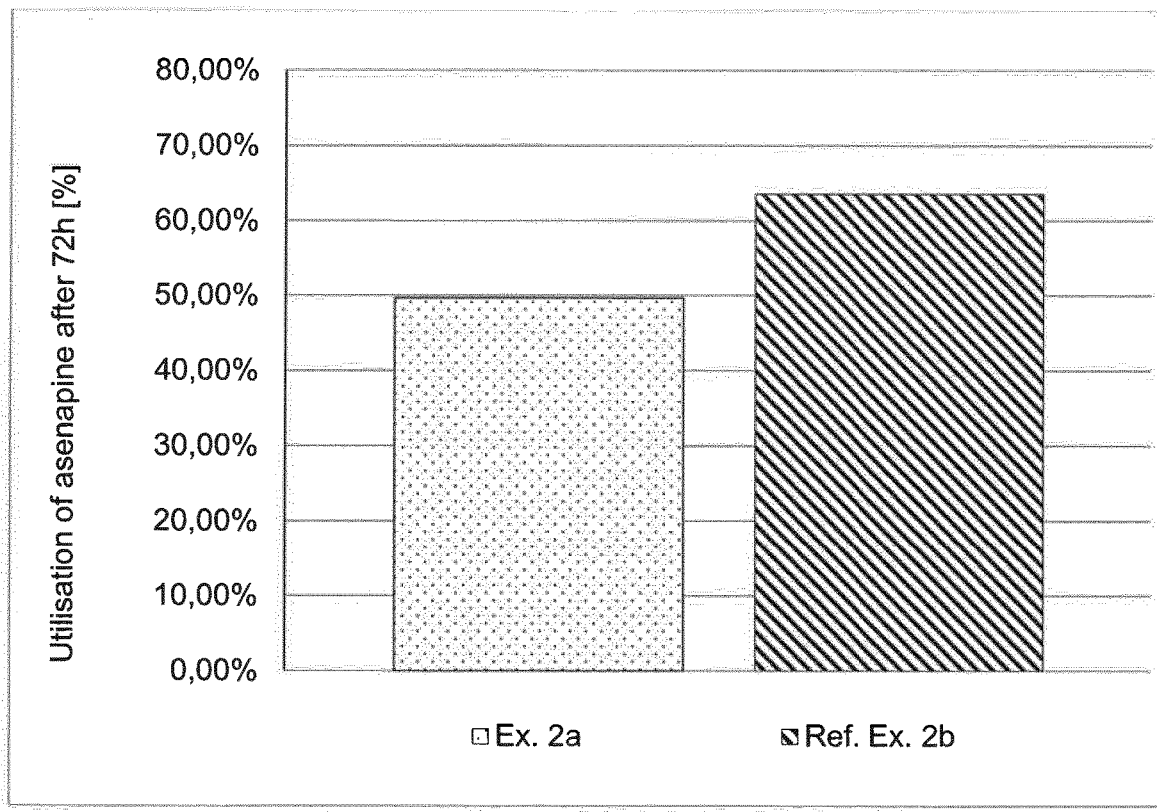

FIG. 2b the utilisation of asenapine of TTS prepared according to Ex. 2a and Ref Ex. 2b after 72 h.

Figure 3A:
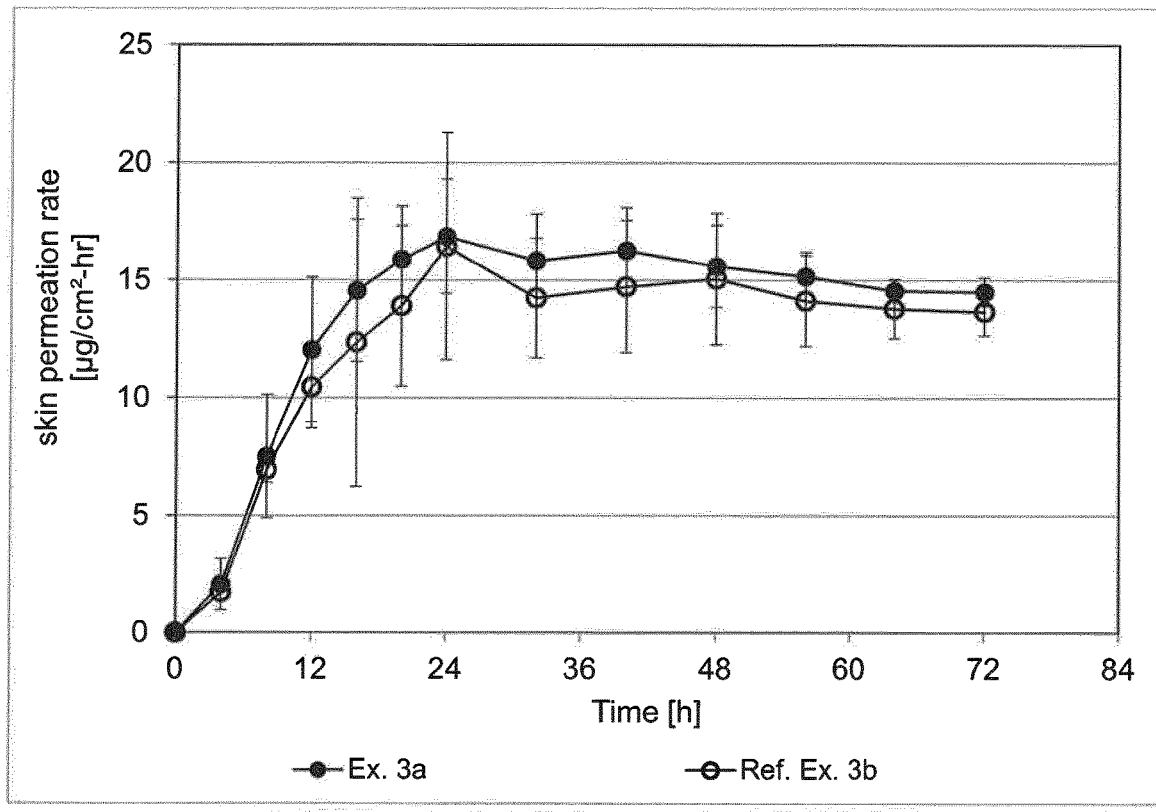

FIG. 3a depicts the asenapine skin permeation rate of TTS prepared according to Ex. 3a and Ref Ex. 3b for hours 0 to 72.

Figure 3B:
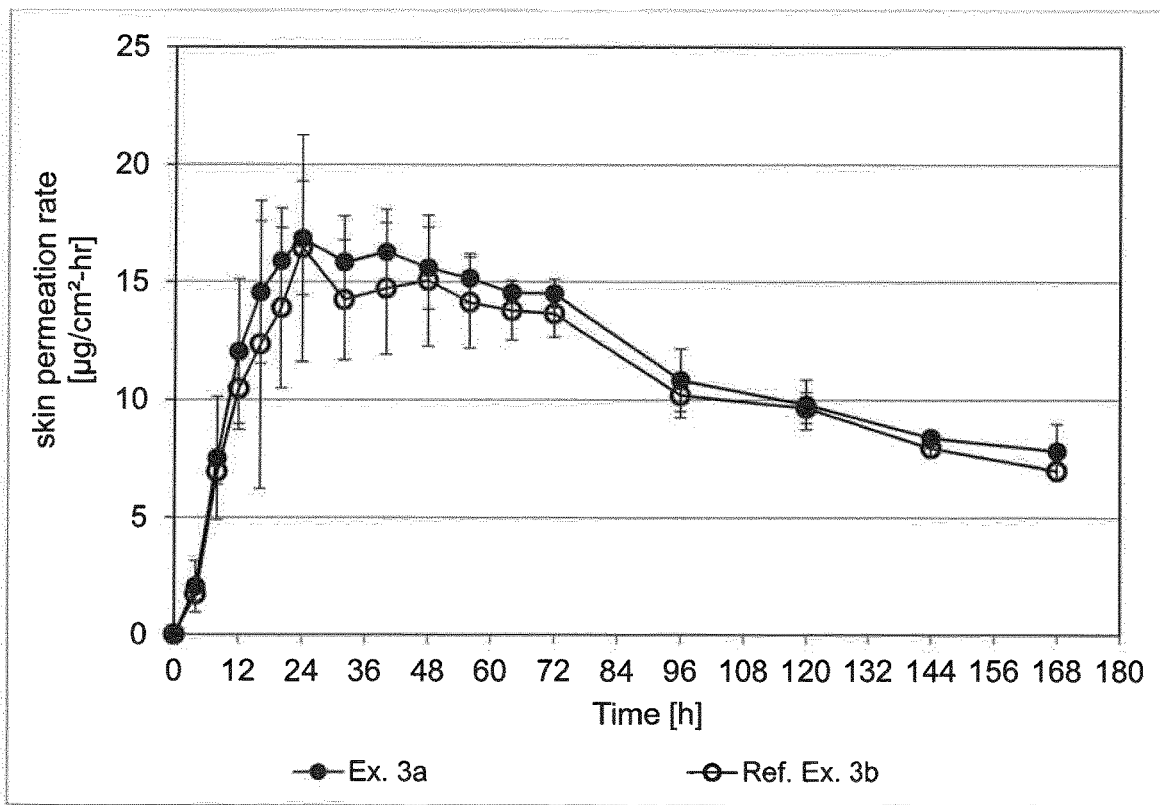

FIG. 3b depicts the asenapine skin permeation rate of TTS prepared according to Ex. 3a and Ref Ex. 3b for hours 0 to 168.

Figure 3C:
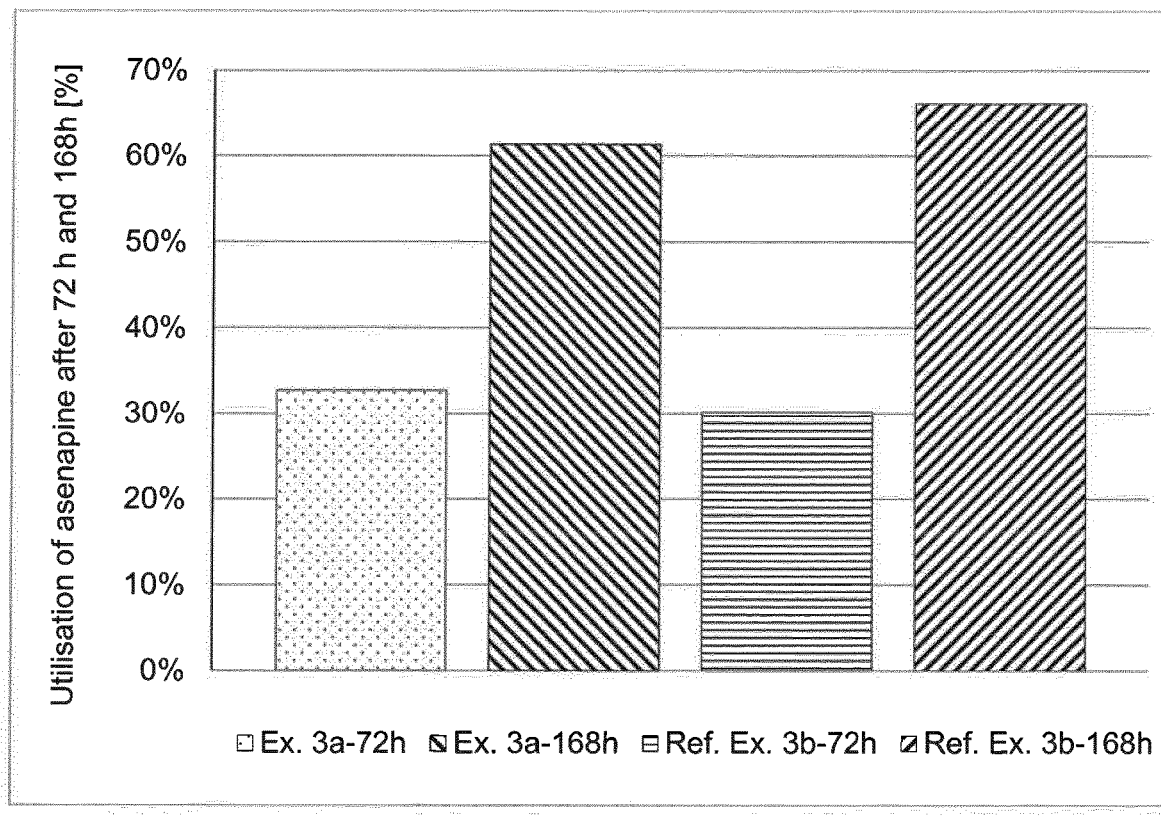

FIG. 3c depicts the utilisation of asenapine of TTS prepared according to Ex. 3a and Ref Ex. 3b after 72 h and after 168 h.

Figure 4A:
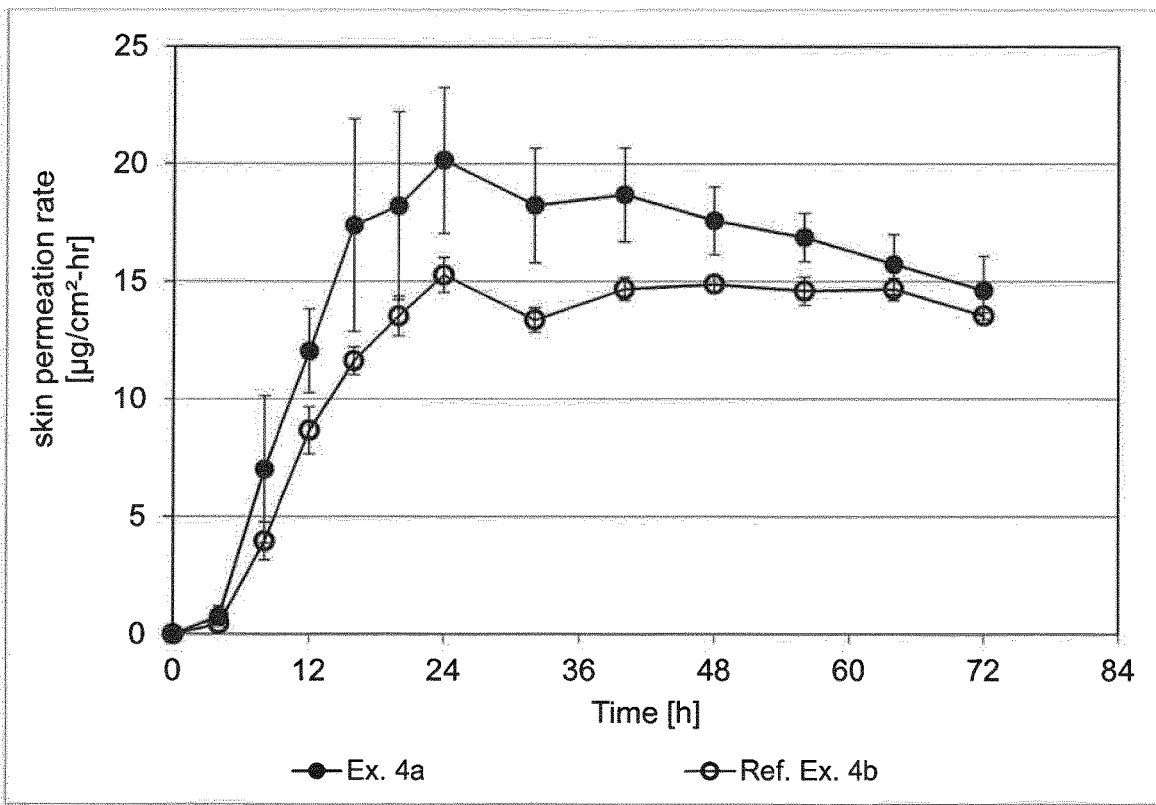

FIG. 4a depicts the asenapine skin permeation rate of TTS prepared according to Ex. 4a and Ref Ex. 4b for hours 0 to 72.

Figure 4B:
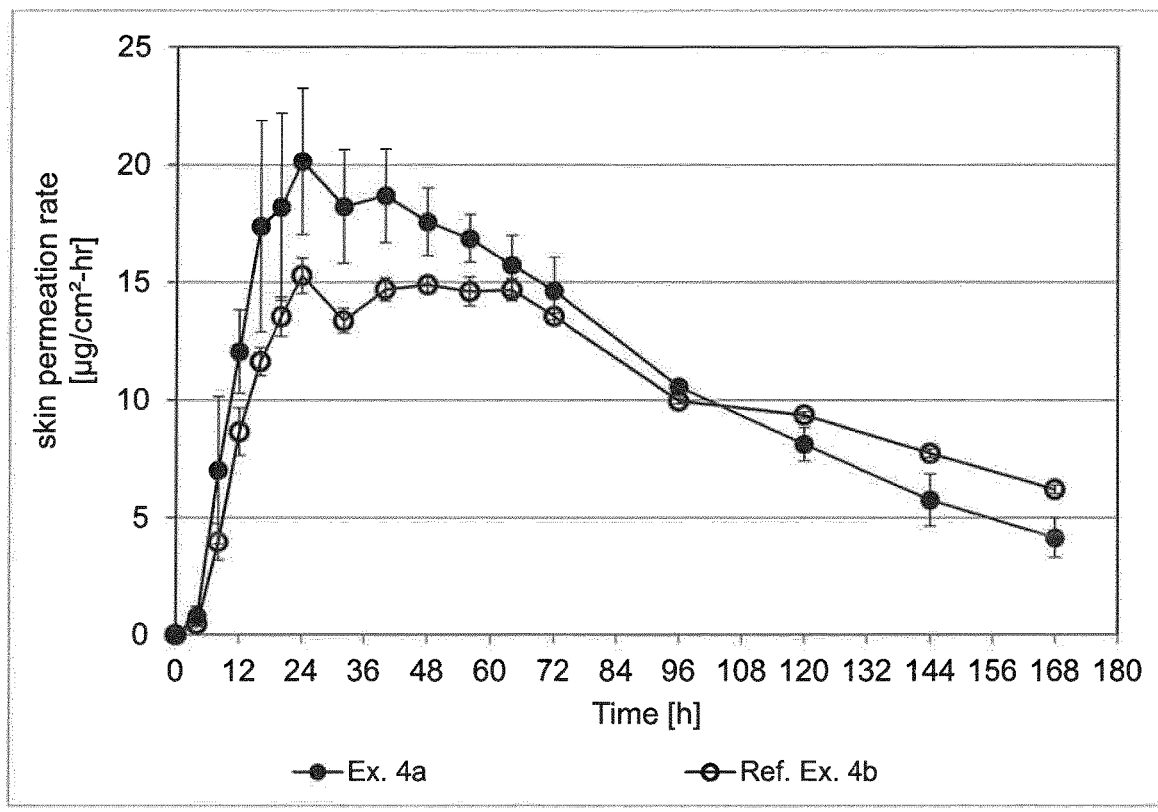

FIG. 4b depicts the asenapine skin permeation rate of TTS prepared according to Ex. 4a and Ref. Ex. 4b for hours 0 to 168.

Figure 4C:
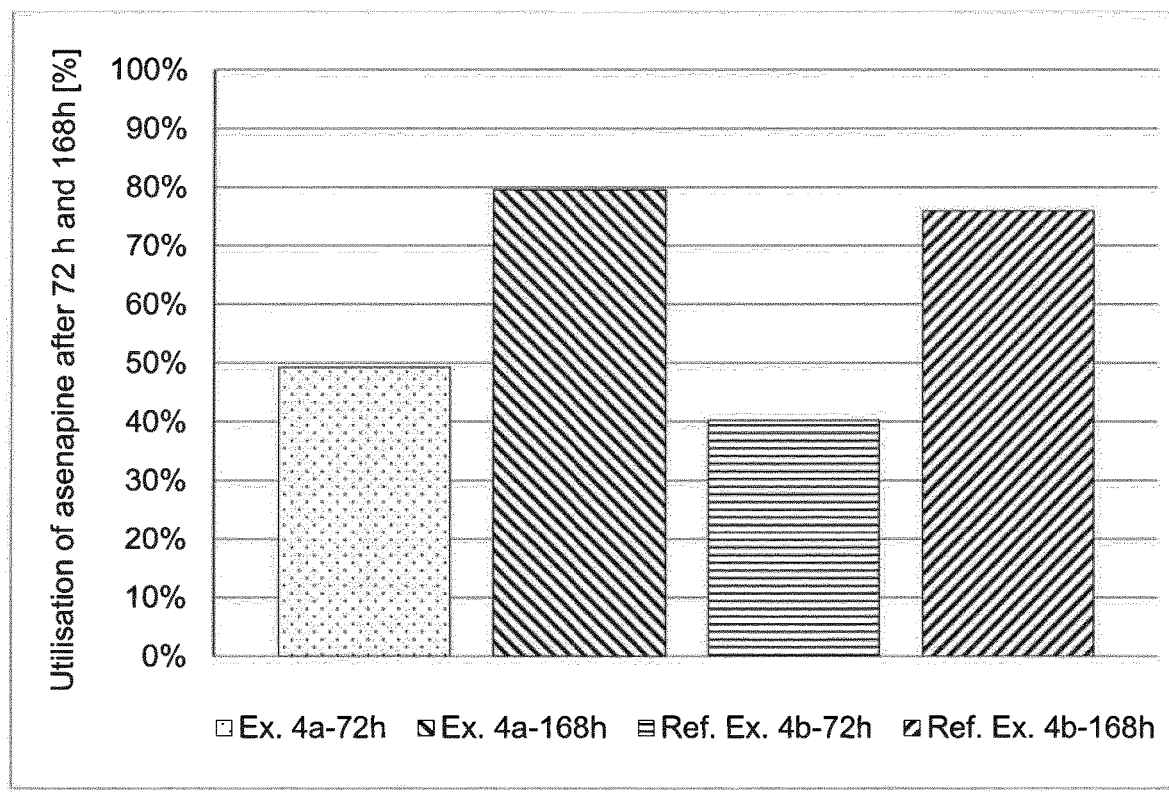

FIG. 4c depicts the utilisation of asenapine of TTS prepared according to Ex. 4a and Ref Ex. 4b after 72 h and 168 h.

Figure 4D:
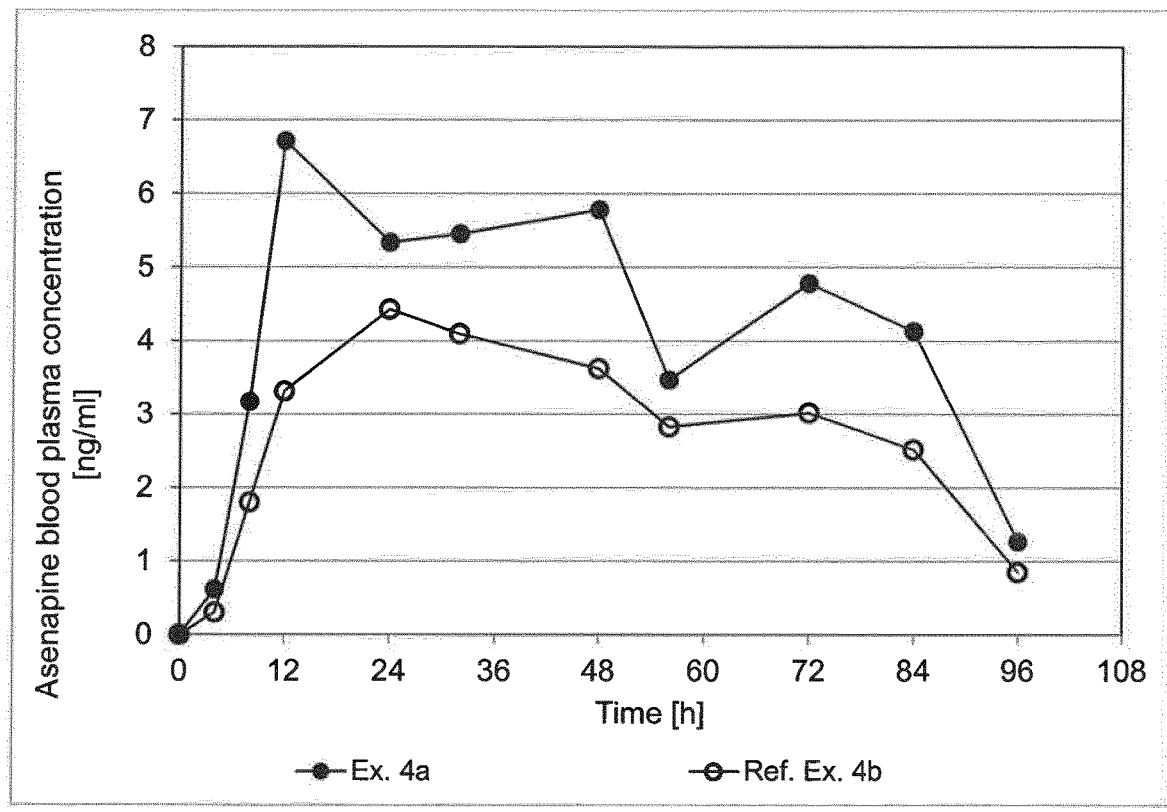

FIG. 4d depicts the asenapine blood plasma concentration of TTS prepared according to Ex. 4a and Ref Ex. 4b for hours 0 to 96.

DETAILED DESCRIPTION

TTS Structure

The present invention is related to a transdermal therapeutic system for the transdermal administration of asenapine comprising an asenapine-containing layer structure.

The asenapine-containing layer structure in particular may contain a therapeutically effective amount of asenapine.

According to the present invention, the transdermal therapeutic system also comprises a silicone acrylic hybrid polymer, and the asenapine-containing layer structure comprises A) a backing layer and B) an asenapine-containing layer.

Thus, in a first aspect, the present invention relates to a transdermal therapeutic system for the transdermal administration of asenapine comprising an asenapine-containing layer structure, said asenapine-containing layer structure comprising:
  A) a backing layer; and
  B) an asenapine-containing layer;
wherein the transdermal therapeutically system comprises a silicone acrylic hybrid polymer.

The backing layer is in particular substantially asenapine-impermeable.

Preferably, the asenapine-containing layer structure is an asenapine-containing self-adhesive layer structure. Thus, the transdermal therapeutic system for the transdermal administration of asenapine according to the present invention preferably comprises an asenapine-containing self-adhesive layer structure, and while such an asenapine-containing self-adhesive layer structure may or may not comprise an additional skin contact layer, preferably the asenapine-containing layer itself is self-adhesive so that an additional skin contact layer is not required and preferably is not present. Particularly preferably, the silicone acrylic hybrid polymer, which is present in the transdermal therapeutic system, is present in the asenapine-containing self-adhesive layer structure and even more preferably in the asenapine-containing layer, and provides the self-adhesive properties.

The TTS according to the present invention may be a matrix-type TTS or a reservoir-type TTS. Preferably, the TTS according to the present invention is a matrix-type TTS.

In such a matrix-type TTS according to the invention, the asenapine is homogeneously dissolved and/or dispersed within a polymeric carrier, i.e. the matrix, which forms with the asenapine and optionally remaining ingredients a matrix layer. Thus, in such an embodiment, the asenapine-containing layer is an asenapine-containing matrix layer. While the asenapine-containing layer structure may or may not comprise an additional skin contact layer, it is preferred that the asenapine-containing matrix layer is self-adhesive, so that an additional skin contact layer is not required and preferably is not present. If an asenapine-containing matrix layer is prepared by laminating together two asenapine-containing matrix layers, which are of substantially the same composition, the resulting double layer is to be regarded as one asenapine-containing matrix layer.

In a reservoir-type TTS according to the present invention, an asenapine-containing reservoir is sealed between the backing layer and a rate-controlling membrane. Thus, the asenapine-containing layer is an asenapine-containing reservoir layer, which preferably comprises a liquid reservoir comprising the asenapine. The reservoir-type TTS typically additionally comprises a skin contact layer, wherein the reservoir layer and the skin contact layer are preferably separated by the rate-controlling membrane.

In specific embodiments, e.g. as outlined above, the asenapine-containing layer structure according to the present invention comprises or does not comprise an additional skin contact layer. The additional skin contact layer is preferably self-adhesive and provides for adhesion between the asenapine-containing layer structure and the skin of the patient during administration.

In such embodiments, the asenapine-containing layer structure may or may not comprise a membrane which is located between the asenapine-containing layer and the additional skin contact layer, wherein the membrane is preferably a rate controlling membrane.

It is furthermore preferred that the asenapine-containing layer is directly attached to the backing layer, so that there is no additional layer between the backing layer and the asenapine-containing layer. Consequently, a layer structure of low complexity is obtained, which is advantageous, e.g., in terms of the costs for the manufacture.

In particular, it is preferred that the asenapine-containing layer structure comprises not more than 3 and preferably comprises 2 layers, i.e. only the backing layer and the asenapine-containing layer. Sufficient adhesion between the asenapine-containing layer structure and the skin of the patient during administration is then provided by the asenapine-containing layer, which is preferably an asenapine-containing pressure-sensitive adhesive layer.

The self-adhesive properties of the TTS are preferably provided by the silicone acrylic hybrid polymer, which is present in the TTS, preferably in the asenapine-containing layer structure, and more preferably in the asenapine-containing layer, which most preferable is an asenapine-containing matrix layer. Thus, in a preferred embodiment of the invention, the silicone acrylic hybrid polymer is a silicone acrylic hybrid pressure-sensitive adhesive. Further details regarding the silicone acrylic hybrid polymer according to the invention are provided further below.

According to certain embodiments of the invention, the TTS may further comprise an adhesive overlay. This adhesive overlay is in particular larger than the asenapine-containing layer structure and is attached thereto for enhancing the adhesive properties of the overall transdermal therapeutic system. Said adhesive overlay comprises also a backing layer and an adhesive layer. The area of said adhesive overlay adds to the overall size of the TTS but does not add to the area of release. The adhesive overlay comprises a self-adhesive polymer or a self-adhesive polymer mixture selected from the group of silicone acrylic hybrid polymers, acrylic polymers, polysiloxanes, polyisobutylenes, styrene-isoprene-styrene copolymers, and mixtures thereof, which may be identical to or different from any polymer or polymer mixture included in the asenapine-containing self-adhesive layer structure.

The asenapine-containing layer structure according to the invention, such as an asenapine-containing self-adhesive layer structure, is normally located on a detachable protective layer (release liner) from which it is removed immediately before application to the surface of the patient's skin. Thus, the TTS may further comprise a release liner. A TTS protected this way is usually stored in a blister pack or a seam-sealed pouch. The packaging may be child resistant and/or senior friendly.

Asenapine-Containing Layer

As outlined in more detail above, the TTS according to a first aspect of the present invention comprises an asenapine-containing layer structure comprising a backing layer and an asenapine-containing layer, wherein the TTS comprises a silicone acrylic hybrid polymer.

In a preferred embodiment, the asenapine-containing layer comprises:
 1. asenapine; and
 2. a silicone acrylic hybrid polymer.

As outlined above, in one preferred embodiment of the invention, the asenapine-containing layer is an asenapine-containing matrix layer, and preferably is a pressure-sensitive adhesive layer. In such an asenapine-containing matrix layer, the asenapine is homogeneously distributed within a polymer matrix. The polymer matrix preferably comprises the silicone acrylic hybrid polymer. Thus it is preferred according to the present invention that the asenapine-containing matrix layer comprises asenapine and the silicone acrylic hybrid polymer.

As outlined above, the asenapine-containing layer structure is preferably an asenapine-containing self-adhesive layer structure. Accordingly, it is preferred that the asenapine-containing layer is an asenapine-containing pressure-sensitive adhesive layer, and more preferably an asenapine-containing pressure-sensitive adhesive matrix layer.

In order to maintain a certain driving force and thus to achieve sufficient skin permeation, the asenapine amount and concentration in the asenapine-containing layer is preferably kept at a certain level. Thus, in preferred embodiments of the invention, the asenapine-containing layer contains at least 0.10 mg/cm$^2$, preferably at least 0.30 mg/cm$^2$, more preferably at least 0.50 mg/cm$^2$ and most preferably at least 0.60 mg/cm$^2$ asenapine. On the other hand, the asenapine-containing layer may in particular contain less than 4.0 mg/cm$^2$, less than 3.2 mg/cm$^2$, less than 2.4 mg/cm$^2$ or less than 1.7 mg/cm$^2$ asenapine. In other preferred embodiments of the invention, the amount of asenapine in the asenapine-containing layer ranges from 2 to 25%, preferably from 3 to 20% and more preferably from 4 to 15% of the asenapine-containing layer.

In certain embodiments of the invention, the area weight of the asenapine-containing layer ranges from 50 to 230 g/m$^2$, preferably from 70 to 190 g/m$^2$, and most preferably from 90 to 150 g/m$^2$.

Without wishing to be bound by theory, it is believed that the advantageous features of the TTS according to the present invention, such as good in vitro skin permeation are inter alia achieved by the amount of asenapine contained in the TTS, which can be controlled two-way by adjusting concentration and/or the area weight of the asenapine-containing layers such as an asenapine-containing matrix layer.

As outlined above, the asenapine-containing layer preferably comprises 1. asenapine and 2. the silicone acrylic hybrid polymer. In such embodiments, the amount of silicone acrylic hybrid polymer may in particular range from 55 to 98%, preferably from 70 to 98%, and more preferably from 80 to 98% by weight based on the total weight of the asenapine-containing layer.

The asenapine-containing layer may also comprise a non-hybrid polymer, wherein the non-hybrid polymer preferably is a non-hybrid pressure-sensitive adhesive and wherein the non-hybrid polymer is preferably selected from polysiloxanes, polyisobutylenes, styrene-isoprene-styrene block copolymers and acrylic polymers. More details concerning the optional non-hybrid polymers are provided further below.

The asenapine-containing layer thus may comprise the silicone acrylic hybrid polymer and/or a non-hybrid polymer, and the total polymer content, referring to the total amount of both silicone acrylic hybrid polymer and non-hybrid polymer, in particular may range from 70 to 98%, preferably from 80 to 98%, and more preferably from 85 to 98% of the asenapine-containing layer.

The asenapine-containing layer may also comprise further excipients or additives selected from the group consisting of crystallization inhibitors, cross-linking agents, solubilizers, fillers, tackifiers, film-forming agents, plasticizers, stabilizers, softeners, substances for skincare, permeation enhancers, pH regulators, and preservatives. Details on such excipients and additives are provided further below.

As previously mentioned, the asenapine-containing layer provides the area of release. In preferred embodiments of the invention, the area of release ranges from 5 to 100 cm$^2$, preferably from 10 to 80 cm$^2$, and more preferably from 10 to 60 cm$^2$.

Asenapine

The transdermal therapeutic system of the present invention comprises asenapine, and in particular therapeutically effective amounts of asenapine, in an asenapine-containing layer structure, i.e. in an asenapine-containing layer.

While the active agent may, in accordance with the present invention, be present in the TTS in protonated or in free base form, the free base form is preferred.

Thus, in certain embodiments, the asenapine in the asenapine-containing layer is included in the form of the free base.

In certain embodiments, the asenapine-containing layer is obtainable by incorporating the asenapine in the form of the free base. In a further embodiment, the asenapine-containing matrix layer is obtainable by incorporating the asenapine in the form of the free base.

In particular, at least 90 mol %, preferably at least 95 mol %, more preferably at least 98 mol % and most preferably at least 99 mol % of the asenapine in the asenapine-containing layer is present in the form of the free base.

The asenapine in the asenapine-containing layer may be completely dissolved, or the asenapine-containing layer may contain asenapine particles, preferably constituted of asenapine free base.

The total amount of asenapine in the TTS is important for the amount of active released and also for the release rate. Thus, in certain preferred embodiments, the amount of asenapine contained in the TTS ranges from 3 to 100 mg, preferably from 3 to 21 mg or from 10 to 80 mg, and most preferably from 3.5 to 14 mg or from 15 to 60 mg.

In certain embodiments, the asenapine has a purity of at least 95%, preferably of at least 98% and more preferably of at least 99% as determined by quantitative HPLC. Quantitative HPLC may be performed with Reversed-Phase-HPLC with UV detection. In particular, the following conditions can be used if HPLC is performed isocratically:

Column: Octadecyl phase acc. Ph. Eur. 2.2.29 (USP phase L1)
Kromasil C18 125 mm×4.0 mm; 5 μm or equivalent
Mobile phase: $KH_2PO_4$/Methanol/TEA (45:55:0.1; v:v:v); pH 2.5±0.05
(TEA=triethylamine)
Gradient: isocratic
Flux: 1.0 mL
Injection volume: 30 μL
Column temperature: 40° C.
Wavelength: 225 nm, 270 nm and 3-D-field; Evaluation is performed at 270 nm
Run time: 10 min Furthermore, the following conditions can be used if HPLC is performed with a gradient:

Column: Octadecyl phase acc. Ph. Eur. 2.2.29 (USP phase L1)
Kinetex C18 EVO 100 mm×4.6 mm; 2.1 μm or equivalent
Mobile phase: A: 0.02 mol $KH_2PO_4$ Buffer/Methanol/TEA (70:30:0.1; v:v:v) adj. to
pH 2.5
B: 0.02 mol $KH_2PO_4$ Buffer/Methanol/TEA (30:70:0.1; v:v:v); adj. to
pH 2.5 (TEA=triethylamine)
Flux: 1.0 mL
Injection volume: 30 μL
Column temperature: 40° C.
Wavelength: 225 nm, 270 nm and 3-D-field; Evaluation is performed at 225 nm
Run time: 32 min

| Gradient profile: | 0.00 min: | A: 100% | B: 0% |
|---|---|---|---|
| | 12.00 min: | A: 40% | B: 60% |
| | 18.00 min: | A: 0% | B: 100% |
| | 27.00 min: | A: 0% | B: 100% |
| | 27.01 min: | A: 100% | B: 0% |
| | 32.00 min: | A: 100% | B: 0% |

Silicone Acrylic Hybrid Polymer

The TTS according to the present invention comprises a silicone acrylic hybrid polymer. The silicone acrylic hybrid polymer comprises a polymerized hybrid species that includes silicone-based sub-species and acrylate-based sub-species that have been polymerized together. The silicone acrylic hybrid polymer thus comprises a silicone phase and an acrylic phase. Preferably, the silicone acrylic hybrid polymer is a silicone acrylic hybrid pressure-sensitive adhesive.

The silicone acrylic hybrid pressure-sensitive adhesives are usually supplied and used in solvents like n-heptane and ethyl acetate. The solids content of the pressure-sensitive adhesives is usually between 30% and 80%. The skilled person is aware that the solids content may be modified by adding a suitable amount of solvent.

Preferably, the weight ratio of silicone to acrylate in the silicone acrylic hybrid pressure-sensitive adhesive is from 5:95 to 95:5, or from 20:80 to 80:20, more preferably from 40:60 to 60:40, and most preferably the ratio of silicone to acrylate is about 50:50. Suitable silicone acrylic hybrid pressure-sensitive adhesives having a weight ratio of silicone to acrylate of 50:50 are, for example, the commercially available silicone acrylic hybrid pressure-sensitive adhesives 7-6102, Silicone/Acrylate Ratio 50/50, and 7-6302, Silicone/Acrylate Ratio 50/50, supplied in ethyl acetate by Dow Corning.

The preferred silicone acrylic hybrid pressure-sensitive adhesives in accordance with the invention are characterized by a solution viscosity at 25° C. and about 50% solids content in ethyl acetate of more than about 400 cP, or from about 500 cP to about 3,500 cP, in particular from about 1,000 cP to about 3,000 cP, more preferred from about 1,200 cP to about 1,800, or most preferred of about 1,500 cP or alternatively more preferred from about 2,200 cP to about 2,800 cP, or most preferred of about 2,500 cP, preferably as measured using a Brookfield RVT viscometer equipped with a spindle number 5 at 50 RPM.

These silicone acrylic hybrid pressure-sensitive adhesives may also be characterized by a complex viscosity at 0.1 rad/s at 30° C. of less than about 1.0e9 Poise, or from about 1.0e5 Poise to about 9.0e8 Poise, or more preferred from about 9.0e5 Poise to about 1.0e7 Poise, or most preferred about 4.0e6 Poise, or alternatively more preferred from about 2.0e6 Poise to about 9.0e7 Poise, or most preferred about 1.0e7 Poise, preferably as measured using a Rheometrics ARES rheometer, wherein the rheometer is equipped with 8 mm plates and the gap zeroed.

To prepare samples for measuring the rheological behavior using a Rheometrics ARES rheometer, between 2 and 3 grams of adhesive solution can be poured onto a SCOTCH-PAK 1022 fluoropolymer release liner and allow to sit for 60 minutes under ambient conditions. To achieve essentially solvent-free films of the adhesive, they can be placed in an oven at 110° C.+/−10° C. for 60 minutes. After removing from the oven and letting equilibrate to room temperature. The films can be removed from the release liner and folded over to form a square. To eliminate air bubbles the films can be compressed using a Carver press. The samples can then be loaded between the plates and are compressed to 1.5+/−0.1 mm at 30° C. The excess adhesive is trimmed and the final gap recorded. A frequency sweep between 0.01 to 100 rad/s can be performed with the following settings: Temperature=30° C.; strain=0.5-1% and data collected at 3 points/decade.

Suitable silicone acrylic hybrid pressure-sensitive adhesives which are commercially available include the PSA series 7-6100 and 7-6300 manufactured and supplied in n-heptane or ethyl acetate by Dow Corning (7-610X and 7-630X; X=1 n-heptane-based/X=2 ethyl acetate-based).

For example, the 7-6102 silicone acrylic hybrid PSA having a silicone/acrylate ratio of 50/50 is characterized by a solution viscosity at 25° C. and about 50% solids content in ethyl acetate of 2,500 cP and a complex viscosity at 0.1 rad/s at 30° C. of 1.0e7 Poise. The 7-6302 silicone acrylic hybrid PSA having a silicone/acrylate ratio of 50/50 has a solution viscosity at 25° C. and about 50% solids content in ethyl acetate of 1,500 cP and a complex viscosity at 0.1 rad/s at 30° C. of 4.0e6 Poise.

Depending on the solvent in which the silicone acrylic hybrid pressure-sensitive adhesive is supplied, the arrangement of the silicone phase and the acrylic phase providing a silicone or acrylic continuous external phase and a corresponding discontinuous internal phase is different. If the silicone acrylic hybrid pressure-sensitive adhesive is provided in n-heptane, the composition contains a continuous, silicone external phase and a discontinuous, acrylic internal phase. If the silicone acrylic hybrid pressure-sensitive adhesive is provided in ethyl acetate, the composition contains a continuous, acrylic external phase and a discontinuous, silicone internal phase. After evaporating the solvent in which the silicone acrylic hybrid pressure-sensitive adhesive is provided, the phase arrangement of the resulting pressure-sensitive adhesive film or layer corresponds to the phase arrangement of the solvent-containing adhesive coating composition. For example, in the absence of any substance that may induce an inversion of the phase arrangement in a silicone acrylic hybrid pressure sensitive adhesive composition, a pressure-sensitive adhesive layer prepared from a silicone acrylic hybrid pressure-sensitive adhesive in n-heptane provides a continuous, silicone external phase and a discontinuous, acrylic internal phase, a pressure-sensitive adhesive layer prepared from a silicone acrylic hybrid pressure-sensitive adhesive in ethyl acetate provides a continuous, acrylic external phase and a discontinuous, silicone internal phase. The phase arrangement of the compositions can, for example, be determined in peel force tests with pressure-sensitive adhesive films or layers prepared from the silicone acrylic hybrid PSA compositions which are attached to a siliconized release liner. The pressure-sensitive adhesive film contains a continuous, silicone external phase if the siliconized release liner cannot or can only hardly be removed from the pressure-sensitive adhesive film (laminated to a backing film) due to the blocking of the two silicone surfaces. Blocking results from the adherence of two silicone layers which comprise a similar surface energy. The silicone adhesive shows a good spreading on the siliconized liner and therefore can create a good adhesion to the liner. If the siliconized release liner can easily be removed the pressure-sensitive adhesive film contains a continuous, acrylic external phase. The acrylic adhesive has no good spreading due to the different surface energies and thus has a low or almost no adhesion to the siliconized liner.

According to a preferred embodiment of the invention the silicone acrylic hybrid polymer is a silicone acrylic hybrid pressure-sensitive adhesive obtainable from a silicon-containing pressure-sensitive adhesive composition comprising acrylate or methacrylate functionality. It is to be understood that the silicon-containing pressure-sensitive adhesive composition comprising acrylate or methacrylate functionality can include only acrylate functionality, only methacrylate functionality, or both acrylate functionality and methacrylate functionality.

According to certain embodiments of the invention the silicone acrylic hybrid pressure-sensitive adhesive comprises the reaction product of (a) a silicon-containing pressure-sensitive adhesive composition comprising acrylate or methacrylate functionality, (b) an ethylenically unsaturated monomer, and (c) an initiator. That is, the silicone acrylic hybrid pressure-sensitive adhesive is the product of the chemical reaction between these reactants ((a), (b), and (c)). In particular, the silicone acrylic hybrid pressure-sensitive adhesive includes the reaction product of (a) a silicon-containing pressure-sensitive adhesive composition comprising acrylate or methacrylate functionality, (b) a (meth)acrylate monomer, and (c) an initiator (i.e., in the presence of the initiator). That is, the silicone acrylic hybrid pressure-sensitive adhesive includes the product of the chemical reaction between these reactants ((a), (b), and (c)).

The reaction product of (a) a silicon-containing pressure-sensitive adhesive composition comprising acrylate or methacrylate functionality, (b) an ethylenically unsaturated monomer, and (c) an initiator may contain a continuous, silicone external phase and a discontinuous, acrylic internal phase or the reaction product of (a), (b), and (c) may contain a continuous, acrylic external phase and a discontinuous, silicone internal phase.

The silicon-containing pressure-sensitive adhesive composition comprising acrylate or methacrylate functionality (a) is typically present in the silicone acrylic hybrid pressure-sensitive adhesive in an amount of from 5 to 95, more typically 25 to 75, parts by weight based on 100 parts by weight of the hybrid pressure-sensitive adhesive.

The ethylenically unsaturated monomer (b) is typically present in the silicone acrylic hybrid pressure-sensitive adhesive in an amount of from 5 to 95, more typically 25 to 75, parts by weight based on 100 parts by weight of the hybrid pressure-sensitive adhesive.

The initiator (c) is typically present in the silicone acrylic hybrid pressure-sensitive adhesive in an amount of from 0.005 to 3, more typically from 0.01 to 2, parts by weight based on 100 parts by weight of the hybrid pressure-sensitive adhesive.

According to certain embodiments of the invention the silicon-containing pressure-sensitive adhesive composition comprising acrylate or methacrylate functionality (a) comprises the condensation reaction product of (a1) a silicone resin, (a2) a silicone polymer, and (a3) a silicon-containing capping agent which provides said acrylate or methacrylate functionality. The silicone resin (a1) may also be referred to as silicate resin or silica resin. Preferably, the silicone polymer (a2) is a polysiloxane, preferably polydimethylsiloxane. It is to be understood that (a1) and (a2) form a silicone-based pressure sensitive adhesive by polycondensation, and that the acrylate or methacrylate functionality is introduced by reaction with (a3).

According to certain embodiments of the invention the silicon-containing pressure-sensitive adhesive composition comprising acrylate or methacrylate functionality (a) comprises the condensation reaction product of:

(a1) a silicone resin, (a2) a silicone polymer, and (a3) a silicon-containing capping agent which provides said acrylate or methacrylate functionality, wherein said silicon-containing capping agent is of the general formula $XYR'_bSiZ_{3-b}$, wherein X is a monovalent radical of the general formula AE- where E is —O— or —NH— and A is an acryl group or a methacryl group, Y is a divalent alkylene radical having from 1 to 6 carbon atoms, R' is a methyl or a phenyl radical, Z is a monovalent hydrolyzable organic radical or a halogen, and b is 0 or 1;

wherein the silicone resin and silicone polymer are reacted to form a pressure-sensitive adhesive, wherein the silicon-containing capping agent is introduced prior to, during, or after the silicone resin and silicone polymer are reacted, and wherein:

the silicon-containing capping agent reacts with the pressure-sensitive adhesive after the silicone resin and silicone polymer have been condensation reacted to form the pressure-sensitive adhesive; or the silicon-containing capping agent reacts in-situ with the silicone resin and silicone polymer.

According to certain embodiments of the invention the silicon-containing pressure-sensitive adhesive composition comprising acrylate or methacrylate functionality comprises the condensation reaction product of a pressure sensitive adhesive and a silicon-containing capping agent which provides said acrylate or methacrylate functionality. That is, the silicon-containing pressure sensitive adhesive composition comprising acrylate or methacrylate functionality is essentially a pressure sensitive adhesive that has been capped or end blocked with the silicon-containing capping agent which provides said acrylate or methacrylate functionality, wherein the pressure sensitive adhesive comprises the condensation reaction product of the silicone resin and the silicone polymer. Preferably, the silicone resin reacts in an amount of from 30 to 80 parts by weight to form the pressure sensitive adhesive, and the silicone polymer reacts in an amount of from 20 to 70 parts by weight to form the pressure sensitive adhesive. Both of these parts by weight are based on 100 parts by weight of the pressure sensitive adhesive. Although not required, the pressure sensitive adhesive may comprise a catalytic amount of a condensation catalyst. A wide array of silicone resins and silicone polymers are suitable to make up the pressure sensitive adhesive.

According to certain embodiments of the invention the silicone acrylic hybrid pressure-sensitive adhesive is the reaction product of:

(a) a silicon-containing pressure-sensitive adhesive composition comprising acrylate or methacrylate functionality that comprises the condensation reaction product of:

(a1) a silicone resin, (a2) a silicone polymer, and (a3) a silicon-containing capping agent which provides said acrylate or methacrylate functionality, wherein said silicon-containing capping agent is of the general formula $XYR'_bSiZ_{3-b}$, wherein X is a monovalent radical of the general formula AE— where E is —O— or —NH— and A is an acryl group or a methacryl group, Y is a divalent alkylene radical having from 1 to 6 carbon atoms, R' is a methyl or a phenyl radical, Z is a monovalent hydrolyzable organic radical or a halogen, and b is 0 or 1;

wherein the silicone resin and silicone polymer are reacted to form a pressure-sensitive adhesive, wherein the silicon-containing capping agent is introduced prior to, during, or after the silicone resin and silicone polymer are reacted, and wherein:

the silicon-containing capping agent reacts with the pressure-sensitive adhesive after the silicone resin and silicone polymer have been condensation reacted to form the pressure-sensitive adhesive; or the silicon-containing capping agent reacts in-situ with the silicone resin and silicone polymer;

(b) an ethylenically unsaturated monomer; and (c) an initiator.

The silicone acrylic hybrid composition used in the present invention may be described by being prepared by a method comprising the steps of:

(i) providing a silicon-containing pressure-sensitive adhesive composition comprising acrylate or methacrylate functionality that comprises the condensation reaction product of:

a silicone resin, a silicone polymer, and a silicon-containing capping agent which provides said acrylate or methacrylate functionality, wherein said silicon-containing capping agent is of the general formula $XYR'_bSiZ_{3-b}$, wherein X is a monovalent radical of the general formula AE— where E is —O— or —NH— and A is an acryl group or a methacryl group, Y is a divalent alkylene radical having from 1 to 6 carbon atoms, R' is a methyl or a phenyl radical, Z is a monovalent hydrolyzable organic radical or a halogen, and b is 0 or 1;

wherein the silicone resin and silicone polymer are reacted to form a pressure-sensitive adhesive, wherein the silicon-containing capping agent is introduced prior to, during, or after the silicone resin and silicone polymer are reacted, and wherein:

the silicon-containing capping agent reacts with the pressure-sensitive adhesive after the silicone resin and silicone polymer have been condensation reacted to form the pressure-sensitive adhesive; or the silicon-containing capping agent reacts in-situ with the silicone resin and silicone polymer;

(ii) polymerizing an ethylenically unsaturated monomer and the silicon-containing pressure-sensitive adhesive composition comprising acrylate or methacrylate functionality of step (i) in the presence of an initiator to form a silicone acrylic hybrid composition, optionally at a temperature of from 50° C. to 100° C., or from 65° C. to 90° C.

During the polymerization of the ethylenically unsaturated monomer and the silicon-containing pressure-sensitive adhesive composition comprising acrylate or methacrylate functionality, the silicone to acrylic ratio can be controlled and optimized as desired. The silicone to acrylic ratio can be controlled by a wide variety of mechanisms in and during the method. An illustrative example of one such mechanism is the rate controlled addition of the ethylenically unsaturated monomer or monomers to the silicon-containing pressure-sensitive adhesive composition comprising acrylate or methacrylate functionality. In certain applications, it may be desirable to have the silicone-based sub-species, or the overall silicone content, to exceed the acrylate-based sub-species, or the overall acrylic content. In other applications, it may be desirable for the opposite to be true. Independent of the end application, it is generally preferred, as already described above, that the silicon-containing pressure-sensitive adhesive composition comprising acrylate or methacrylate functionality is preferably present in the silicone acrylic hybrid composition in an amount of from about 5 to about 95 parts by weight, more preferably from about 25 to about 75 parts by weight, and still more preferably from about 40 to about 60 parts by weight based on 100 parts by weight of the silicone acrylic hybrid composition.

According to a certain embodiment of the invention, the silicone acrylic hybrid composition used in the present invention may be described by being prepared by a method comprising the steps of:
(i) providing a silicon-containing pressure-sensitive adhesive composition comprising acrylate or methacrylate functionality that comprises the condensation reaction product of:
  a silicone resin,
  a silicone polymer, and
  a silicon-containing capping agent which provides said acrylate or methacrylate functionality, wherein said silicon-containing capping agent is of the general formula $XYR'_bSiZ_{3-b}$, wherein
    X is a monovalent radical of the general formula AE— where E is —O— or —NH— and A is an acryl group or a methacryl group,
    Y is a divalent alkylene radical having from 1 to 6 carbon atoms,
    R' is a methyl or a phenyl radical,
    Z is a monovalent hydrolyzable organic radical or a halogen, and
    b is 0 or 1;
  wherein the silicone resin and silicone polymer are reacted to form a pressure-sensitive adhesive, wherein the silicon-containing capping agent is introduced prior to, during, or after the silicone resin and silicone polymer are reacted, and wherein:
    the silicon-containing capping agent reacts with the pressure-sensitive adhesive after the silicone resin and silicone polymer have been condensation reacted to form the pressure-sensitive adhesive; or
    the silicon-containing capping agent reacts in-situ with the silicone resin and silicone polymer;
(ii) polymerizing an ethylenically unsaturated monomer and the silicon-containing pressure-sensitive adhesive composition comprising acrylate or methacrylate functionality of step (i) in a first solvent in the presence of an initiator at a temperature of from 50° C. to 100° C. to form a silicone acrylic hybrid composition;
(iii) removing the first solvent; and
(iv) adding a second solvent to form the silicone acrylic hybrid composition, wherein the phase arrangement of the silicone acrylic hybrid composition is selectively controlled by selection of the second solvent.

The silicone acrylic hybrid PSA composition used in the present invention may also be described by being prepared by a method comprising the steps of:
(i) providing a silicon-containing pressure-sensitive adhesive composition comprising acrylate or methacrylate functionality that comprises the condensation reaction product of:
  a silicone resin,
  a silicone polymer, and
  a silicon-containing capping agent which provides said acrylate or methacrylate functionality, wherein said silicon-containing capping agent is of the general formula $XYR'_bSiZ_{3-b}$, wherein
    X is a monovalent radical of the general formula AE— where E is —O— or —NH— and A is an acryl group or a methacryl group,
    Y is a divalent alkylene radical having from 1 to 6 carbon atoms,
    R' is a methyl or a phenyl radical,
    Z is a monovalent hydrolyzable organic radical or a halogen, and
    b is 0 or 1;
  wherein the silicone resin and silicone polymer are reacted to form a pressure-sensitive adhesive, wherein the silicon-containing capping agent is introduced prior to, during, or after the silicone resin and silicone polymer are reacted, and wherein:
    the silicon-containing capping agent reacts with the pressure-sensitive adhesive after the silicone resin and silicone polymer have been condensation reacted to form the pressure-sensitive adhesive; or
    the silicon-containing capping agent reacts in-situ with the silicone resin and silicone polymer;
(ii) polymerizing an ethylenically unsaturated monomer and the silicon-containing pressure-sensitive adhesive composition comprising acrylate or methacrylate functionality of step (i) in a first solvent in the presence of an initiator at a temperature of from 50° C. to 100° C. to form a silicone acrylic hybrid composition;
(iii) adding a processing solvent, wherein the processing solvent has a higher boiling point than the first solvent, and
(iv) applying heat at a temperature of from 70° C. to 150° C. such that a majority of the first solvent is selectively removed;
(v) removing the processing solvent; and.
(vi) adding a second solvent to form the silicone acrylic hybrid composition, wherein the phase arrangement of the silicone acrylic hybrid composition is selectively controlled by selection of the second solvent.

The silicone resin according to the previous paragraphs may contain a copolymer comprising triorganosiloxy units of the formula $R^X_3SiO_{1/2}$ and tetrafunctional siloxy units of the formula $SiO_{4/2}$ in a ratio of from 0.1 to 0.9, preferably of about 0.6 to 0.9, triorganosiloxy units for each tetrafunctional siloxy unit. Preferably, each $R^X$ independently denotes a monovalent hydrocarbon radical having from 1 to 6 carbon atoms, vinyl, hydroxyl or phenyl groups.

The silicone polymer according to the previous paragraphs may comprise at least one polydiorganosiloxane and is preferably end-capped (end-blocked) with a functional group selected from the group consisting of hydroxyl groups, alkoxy groups, hydride groups, vinyl groups, or mixtures thereof. The diorganosubstituent may be selected from the group consisting of dimethyl, methylvinyl, methylphenyl, diphenyl, methylethyl, (3,3,3-trifluoropropyl) methyl and mixtures thereof. Preferably, the diorganosubstituents contain only methyl groups. The molecular weight of polydiorganosiloxane will typically range from about 50,000 to about 1,000,000, preferably, from about 80,000 to about 300,000. Preferably, the polydiorganosiloxane comprises $AR^XSiO$ units terminated with endblocking $TR^XA$-$SiO_{1/2}$ units, wherein the poly-diorganosiloxane has a viscosity of from about 100 centipoise to about 30,000,000 centipoise at 25° C., each A radical is independently selected from $R^X$ or halohydrocarbon radicals having from 1 to 6 carbon atoms, each T radical is independently selected from the group consisting of $R^X$, OH, H or $OR^Y$, and each $R^Y$ is independently an alkyl radical having from 1 to 4 carbon atoms.

As an example using forms of the preferred silicone resin and the preferred silicone polymer, one type of pressure sensitive adhesive is made by:

mixing (i) from 30 to 80 inclusive parts by weight of at least one resin copolymer containing silicon-bonded hydroxyl radicals and consisting essentially of $R^X_3SiO_{1/2}$ units and $SiO_{4/2}$ units in a mole ratio of 0.6 to 0.9 $R^X_3SiO_{1/2}$ units for each $SiO_{4/2}$ unit present, (ii) between about 20 and about 70 parts by weight of at least one polydiorganosiloxane comprising $AR^XSiO$ units terminated with endblocking $TR^XA$-$SiO_{1/2}$ units, wherein the polydiorganosiloxane has a viscosity of from about 100 centipoise to about 30,000,000 centipoise at 25° C. and each $R^X$ is a monovalent organic radical selected from the group consisting of hydrocarbon radicals of from 1 to 6 inclusive carbon atoms, each A radical is independently selected from $R^X$ or halohydrocarbon radicals having from 1 to 6 inclusive carbon atoms, each T radical is independently selected from the group consisting of $R^X$, OH, H or $OR^Y$, and each $R^Y$ is independently an alkyl radical of from 1 to 4 inclusive carbon atoms; a sufficient amount of (iii) at least one of the silicon-containing capping agents, also referred to throughout as endblocking agents, described below and capable of providing a silanol content, or concentration, in the range of 5,000 to 15,000, more typically 8,000 to 13,000, ppm, when desirable an additional catalytic amount of (iv) a mild silanol condensation catalyst in the event that none is provided by (ii), and when necessary, an effective amount of (v) an organic solvent which is inert with respect to (i), (ii), (iii) and (iv) to reduce the viscosity of a mixture of (i), (ii), (iii), and (iv), and condensing the mixture of (i), (ii), (iii) and (iv) at least until a substantial amount of the silicon-containing capping agent or agents have reacted with the silicon-bonded hydroxyl radicals and T radicals of (i) and (ii). Additional organosilicon endblocking agents can be used in conjunction with the silicon-containing capping agent or agents (iii) of the present invention.

The silicon-containing capping agent according to the previous paragraphs may be selected from the group of acrylate functional silanes, acrylate functional silazanes, acrylate functional disilazanes, acrylate functional disiloxanes, methacrylate functional silanes, methacrylate functional silazanes, methacrylate functional disilazanes, methacrylate functional disiloxanes, and combinations thereof and may be described as to be of the general formula $XYR'_bSiZ_{3-b}$, wherein X is a monovalent radical of the general formula AE- where E is —O— or —NH— and A is an acryl group or a methacryl group, Y is a divalent alkylene radical having from 1 to 6 carbon atoms, R' is a methyl or a phenyl radical, Z is a monovalent hydrolyzable organic radical or a halogen, and b is 0, 1 or 2. Preferably, the monovalent hydrolyzable organic radical is of the general formula R"O- where R" is an alkylene radical. Most preferably, this particular endblocking agent is selected from the group of 3-methacryloxypropyldimethylchlorosilane, 3-methacryloxypropyldichlorosilane, 3-methacryloxypropyltrichlorosilane, 3-methacryloxypropyldimethylmethoxysilane, 3-methacryloxypropylmethyldimethoxysilane, 3-methacryloxypropyltrimethoxysilane, 3-methacryloxypropyldimethylethoxysilane, 3-methacryloxypropylmethyldiethoxysilane, 3-methacryloxypropyltriethoxysilane, (methacryloxymethyl)dimethylmethoxysilane, (methacryloxymethyl)methyldimethoxysilane, (methacryloxymethyl)trimethoxysilane, (methacryloxymethyl)dimethylethoxysilane, (methacryloxymethyl)methyldiethoxysilane, methacryloxymethyltriethoxysilane, methacryloxy-propyl-triisopropoxysilane, 3-methacryloxypropyldimethylsilazane, 3-acryloxy-propyldimethylchlorosilane, 3-acryloxypropyldichlorosilane, 3-acryloxypropyl-trichlorosilane, 3-acryloxypropyldimethylmethoxysilane, 3-acryloxy-propylmethyldimethoxysilane, 3-acryloxypropyltrimethoxysilane, 3-acryloxypropyl-dimethylsilazane, and combinations thereof.

The ethylenically unsaturated monomer according to the previous paragraphs can be any monomer having at least one carbon-carbon double bond. Preferably, the ethylenically unsaturated monomer according to the previous paragraphs may be a compound selected from the group consisting of aliphatic acrylates, aliphatic methacrylates, cycloaliphatic acrylates, cycloaliphatic methacrylates, and combinations thereof. It is to be understood that each of the compounds, the aliphatic acrylates, the aliphatic methacrylates, the cycloaliphatic acrylates, and the cycloaliphatic methacrylates, include an alkyl radical. The alkyl radicals of these compounds can include up to 20 carbon atoms. The aliphatic acrylates that may be selected as one of the ethylenically unsaturated monomers are selected from the group consisting of methyl acrylate, ethyl acrylate, propyl acrylate, n-butyl acrylate, iso-butyl acrylate, tert-butyl acrylate, hexyl acrylate, 2-ethylhexyl acrylate, iso-octyl acrylate, iso-nonyl acrylate, iso-pentyl acrylate, tridecyl acrylate, stearyl acrylate, lauryl acrylate, and mixtures thereof. The aliphatic methacrylates that may be selected as one of the ethylenically unsaturated monomers are selected from the group consisting of methyl methacrylate, ethyl methacrylate, propyl methacrylate, n-butyl methacrylate, iso-butyl meth-acrylate, tert-butyl methacrylate, hexyl methacrylate, 2-ethylhexyl methacrylate, iso-octyl methacrylate, iso-nonyl methacrylate, iso-pentyl methacrylate, tridecyl methacrylate, stearyl methacrylate, lauryl methacrylate, and mixtures thereof. The cycloaliphatic acrylate that may be selected as one of the ethylenically unsaturated monomers is cyclohexyl acrylate, and the cycloaliphatic methacrylate that may be selected as one of the ethylenically unsaturated monomers is cyclohexyl methacrylate.

It is to be understood that the ethylenically unsaturated monomer used for preparing the silicone acrylic hybrid pressure sensitive adhesive may be more than one ethylenically unsaturated monomer. That is, a combination of ethylenically unsaturated monomers may be polymerized, more specifically co-polymerized, along with the silicon-containing pressure sensitive adhesive composition comprising acrylate or methacrylate functionality and the initiator. According to a certain embodiment of the invention, the silicone acrylic hybrid pressure-sensitive adhesive is prepared by using at least two different ethylenically unsaturated monomers, preferably selected from the group of 2-ethylhexyl acrylate and methyl acrylate, more preferably in a ratio of 50% 2-ethylhexyl acrylate and 50% methyl acrylate, or in a ratio of 60% 2-ethylhexyl acrylate and 40% methyl acrylate as the acrylic monomer.

The initiator according to the previous paragraphs may be any substance that is suitable to initiate the polymerization of the silicon-containing pressure sensitive adhesive composition comprising acrylate or methacrylate functionality and the ethylenically unsaturated monomer to form the silicone acrylic hybrid. For example, free radical initiators selected from the group of peroxides, azo compounds, redox initiators, and photo-initiators may be used.

Further suitable silicone resins, silicone polymers, silicon-containing capping agents, ethylenically unsaturated monomers, and initiators that can be used in accordance with the previous paragraphs are detailed in WO 2007/145996, EP 2 599 847 A1, and WO 2016/130408.

According to a certain embodiment of the invention, the silicone acrylic hybrid polymer comprises a reaction product of a silicone polymer, a silicone resin and an acrylic polymer, wherein the acrylic polymer is covalently self-cross-linked and covalently bound to the silicone polymer and/or the silicone resin.

According to a certain other embodiment of the invention, the silicone acrylic hybrid polymer comprises a reaction product of a silicone polymer, a silicone resin and an acrylic polymer, wherein the silicone resin contains triorganosiloxy units $R_3SiO_{1/2}$ where R is an organic group, and tetrafunctional siloxy units $SiO_{4/2}$ in a mole ratio of from 0.1 to 0.9 $R_3SiO_{1/2}$ units for each $SiO_{4/2}$.

The acrylic polymer may comprise at least an alkoxysilyl functional monomer, polysiloxane-containing monomer, halosilyl functional monomer or alkoxy halosilyl functional monomer. Preferably, the acrylic polymer is prepared from alkoxysilyl functional monomers selected from the group consisting of trialkoxylsilyl (meth)acrylates, dialkoxyalkyl-silyl (meth)acrylates, and mixtures thereof, or comprises end-capped alkoxysilyl functional groups. The alkoxysilyl functional groups may preferably be selected from the group consisting of trimethoxylsilyl groups, dimethoxymethylsilyl groups, triethoxylsilyl, diethoxymethylsilyl groups and mixtures thereof.

The acrylic polymer may also be prepared from a mixture comprising polysiloxane-containing monomers, preferably from a mixture comprising polydimethylsiloxane mono (meth)acrylate.

The silyl functional monomers will typically be used in amounts of from 0.2 to 20% by weight of the acrylic polymer, more preferably the amount of silyl functional monomers will range from about 1.5 to about 5% by weight of the acrylic polymer.

The amount of polysiloxane-containing monomer will typically be used in amounts of from 1.5 to 50% by weight of the acrylic polymer, more preferably the amount of polysiloxane-containing monomers will range from 5 to 15% by weight of the acrylic polymer.

Alternatively, the acrylic polymer comprises a block or grafted copolymer of acrylic and polysiloxane. An example of a polysiloxane block copolymer is polydimethylsiloxane-acrylic block copolymer. The preferred amount of siloxane block is 10 to 50% by weight of the whole block polymer.

The acrylic polymer comprises alkyl (meth)acrylate monomers. Preferred alkyl (meth)acrylates which may be used have up to about 18 carbon atoms in the alkyl group, preferably from 1 to about 12 carbon atoms in the alkyl group. Preferred low glass transition temperature (Tg) alkyl acrylate with a homopolymer Tg of less than about 0° C. have from about 4 to about 10 carbon atoms in the alkyl group and include butyl acrylate, amyl acrylate, hexyl acrylate, 2-ethylhexyl acrylate, octyl acrylate, isooctyl acrylate, decyl acrylate, isomers thereof, and combinations thereof. Particularly preferred are butyl acrylate, 2-ethylhexyl acrylate and isooctyl acrylate. The acrylic polymer components may further comprise (meth)acrylate monomers having a high Tg such as methyl acrylate, ethyl acrylate, methyl methacrylate and isobutyl methacrylate.

The acrylic polymer component may further comprise a polyisobutylene group to improve cold flow properties of the resultant adhesive.

The acrylic polymer components may comprise nitrogen-containing polar monomers. Examples include N-vinyl pyrrolidone, N-vinyl caprolactam, N-tertiary octyl acrylamide, dimethyl acrylamide, diacetone acrylamide, N-tertiary butyl acrylamide, N-isopropyl acrylamide, cyanoethylacrylate, N-vinyl acetamide and N-vinyl formamide.

The acrylic polymer component may comprise one or more hydroxyl containing monomers such as 2-hydroxyethyl acrylate, 2-hydroxyethyl methacrylate, hydroxypropyl acrylate and/or hydroxypropyl methacrylate.

The acrylic polymer components may, if desired, comprise carboxylic acid containing monomers. Useful carboxylic acids preferably contain from about 3 to about 6 carbon atoms and include, among others, acrylic acid, methacrylic acid, itaconic acid, β-carboxyethyl acrylate and the like. Acrylic acid is particularly preferred.

Other useful, well known co-monomers include vinyl acetate, styrene, cyclohexyl acrylate, alkyl di(meth)acrylates, glycidyl methacrylate and allyl glycidyl ether, as well as macromers such as, for example, poly(styryl)methacrylate.

One acrylic polymer component that can be used in the practice of the invention is an acrylic polymer that comprises from about 90 to about 99.5% by weight of butyl acrylate and from about 0.5 to about 10% by weight dimethoxymethylsilyl methacrylate.

According to a certain embodiment of the invention the silicone acrylic hybrid polymer may be prepared by a) reacting silicone polymer with silicone resin to form a resultant product, b) reacting the resultant product of a) with an acrylic polymer containing reactive functionality, wherein the components are reacted in an organic solvent.

According to a certain embodiment of the invention the silicone acrylic hybrid polymer may be prepared by a) reacting a silicone resin with an acrylic polymer containing reactive functionality to form a resultant product, b) reacting the resultant product of a) with silicone polymer, wherein the components are reacted in an organic solvent.

According to a certain embodiment of the invention the silicone acrylic hybrid polymer may be prepared by a) reacting a silicone polymer with an acrylic polymer containing reactive functionality to form a resultant product, b) reacting the resultant product of a) with silicone resin, wherein the components are reacted in an organic solvent.

Further suitable acrylic polymers, silicone resins, and silicone polymers that can be used for chemically reacting together a silicone polymer, a silicone resin and an acrylic polymer to provide a silicone acrylic hybrid polymer in accordance with the previous paragraphs are detailed in WO 2010/124187.

According to certain embodiments of the invention, the silicone acrylic hybrid polymer used in the TTS is blended with one or more non-hybrid polymers, preferably the silicone acrylic hybrid polymer is blended with one or more non-hybrid pressure sensitive adhesives (e.g. pressure-sensitive adhesives based on polysiloxane or acrylates).

Non-Hybrid Polymers

According to a certain embodiment of the invention, the TTS comprises one or more non-hybrid polymers (e.g. non-hybrid pressure-sensitive adhesives) in addition to the silicone acrylic hybrid polymer. Non-hybrid polymers (e.g. non-hybrid pressure-sensitive adhesives) are polymers (e.g. polymer-based pressure-sensitive adhesives) which do not include a hybrid species. Preferred are non-hybrid polymers (e.g. non-hybrid pressure-sensitive adhesives) based on polysiloxanes, acrylates, polyisobutylenes, or styrene-isoprene-styrene block copolymers.

The non-hybrid polymers (e.g. the non-hybrid pressure-sensitive adhesives) may be contained in the asenapine-containing layer structure and/or in the adhesive overlay, and in particular may be comprised in the asenapine-containing layer.

Non-hybrid pressure-sensitive adhesives are usually supplied and used in solvents like n-heptane and ethyl acetate. The solids content of the pressure-sensitive adhesives is usually between 30% and 80%.

Suitable non-hybrid polymers according to the invention are commercially available e.g. under the brand names BIO-PSAs (pressure sensitive adhesives based on polysiloxanes), Oppanol™ (polyisobutylenes), JSR-SIS (a styrene-isoprene-styrene copolymer) or Duro-Tak™ (acrylic polymers).

Polymers based on polysiloxanes may also be referred to as silicone-based polymers. These polymers based on polysiloxanes are preferably pressure sensitive adhesives based on polysiloxanes. Pressure-sensitive adhesives based on polysiloxanes may also be referred to as silicone-based pressure-sensitive adhesives, or silicone pressure sensitive adhesives.

These pressure-sensitive adhesives based on polysiloxanes provide for suitable tack and for quick bonding to various skin types, including wet skin, suitable adhesive and cohesive qualities, long lasting adhesion to the skin, a high degree of flexibility, a permeability to moisture, and compatibility to many actives and film-substrates. It is possible to provide them with sufficient amine resistance and therefore enhanced stability in the presence of amines. Such pressure-sensitive adhesives are based on a resin-in-polymer concept wherein, by condensation reaction of silanol end blocked polydimethylsiloxane with a silica resin (also referred to as silicate resin), a pressure-sensitive adhesive based on polysiloxane is prepared wherein for amine stability the residual silanol functionality is additionally capped with trimethylsiloxy groups. The silanol end blocked polydimethylsiloxane content contributes to the viscous component of the visco-elastic behavior, and impacts the wetting and the spreadability properties of the adhesive. The resin acts as a tackifying and reinforcing agent, and participates in the elastic component. The correct balance between silanol end blocked polydimethylsiloxane and resin provides for the correct adhesive properties.

In view of the above, silicone-based polymers, and in particular silicone-based pressure sensitive adhesives, are generally obtainable by polycondensation of silanol endblocked polydimethylsiloxane with a silicate resin. Amine-compatible silicone-based polymers, and in particular amine-compatible silicone-based pressure sensitive adhesives, can be obtained by reacting the silicone-based polymer, in particular the silicone-based pressure sensitive adhesive, with trimethylsilyl (e.g. hexamethyldisilazane) in order to reduce the silanol content of the polymer. As a result, the residual silanol functionality is at least partly, preferably mostly or fully capped with trimethylsiloxy groups.

As indicated above, the tackiness of the silicone-based polymer may be modified by the resin-to-polymer ratio, i.e. the ratio of the silanol endblocked polydimethylsiloxane to the silicate resin, which is preferably in the range of from 70:30 to 50:50, preferably from 65:35 to 55:45. The tackiness will be increased with increasing amounts of the polydimethylsiloxane relative to the resin. High tack silicone-based polymers preferably have a resin-to-polymer ratio of 55:45, medium tack silicone-based polymers preferably have a resin-to-polymer ratio of 60:40, and low tack silicone-based polymers preferably have a resin-to-polymer ratio of 65:35. High tack silicone-based polymers preferably have a complex viscosity at 0.01 rad/s and 30° C. of about $5 \times 10^6$ Poise, medium tack silicone-based polymers preferably have a complex viscosity at 0.01 rad/s and 30° C. of about $5 \times 10^7$ Poise, and low tack silicone-based polymers preferably have a complex viscosity at 0.01 rad/s and 30° C. of about $5 \times 10^8$ Poise. High tack amine-compatible silicone-based polymers preferably have a complex viscosity at 0.01 rad/s and 30° C. of about $5 \times 10^6$ Poise, medium tack amine-compatible silicone-based polymers preferably have a complex viscosity at 0.01 rad/s and 30° C. of about $5 \times 10^8$ Poise, and low tack amine-compatible silicone-based polymers preferably have a complex viscosity at 0.01 rad/s and 30° C. of about $5 \times 10^9$ Poise.

Examples of silicone-based PSA compositions which are commercially available include the standard BIO-PSA series (7-4400, 7-4500 and 7-4600 series), the amine compatible (endcapped) BIO-PSA series (7-4100, 7-4200 and 7-4300 series) and the Soft Skin Adhesives series (7-9800) manufactured and typically supplied in n-heptane or ethyl acetate by Dow Corning. For example, BIO-PSA 7-4201 is characterized by a solution viscosity at 25° C. and about 60% solids content in heptane of 450 mPa s and a complex viscosity at 0.01 rad/s at 30° C. of $1 \times 10^8$ Poise. BIO-PSA 7-4301 has a solution viscosity at 25° C. and about 60% solids content in heptane of 500 mPa s and a complex viscosity at 0.01 rad/s at 30° C. of $5 \times 10^6$ Poise.

The pressure-sensitive adhesives based on polysiloxanes are supplied and used in solvents like n-heptane, ethyl acetate or other volatile silicone fluids. The solids content of pressure-sensitive adhesives based on polysiloxanes in solvents is usually between 60 and 85%, preferably between 70 and 80% or between 60 and 75%. The skilled person is aware that the solids content may be modified by adding a suitable amount of solvent.

Pressure-sensitive adhesives based on polysiloxanes, which are, e.g., available from Dow Corning, may be obtained according to the following scheme:

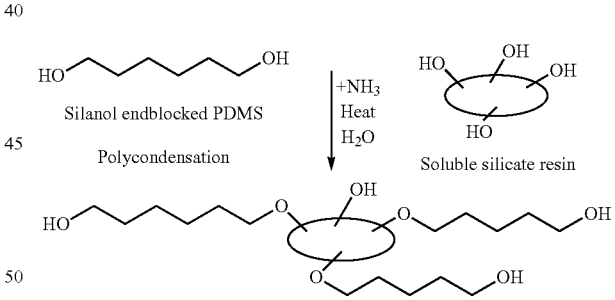

Such pressure-sensitive adhesives based on polysiloxanes are available from Dow Corning, e.g., under the tradenames BIO-PSA 7-4401, BIO-PSA-7-4501, or BIO-PSA 7-4601, which are provided in the solvent n-heptane (indicated by the code "01"), or under the tradenames BIO-PSA 7-4402, BIO-PSA 7-4502, and BIO 7-4602, which are provided in the solvent ethyl acetate (indicated by the code "02"). Typical solids contents in the solvent are in the range of from 60 to 75%. The code "44" indicates a resin-to-polymer ratio of 65:35 resulting in a low tackiness, the code "45" indicates a resin-to-polymer ratio of 60:40 resulting in medium tackiness, the code "46" indicates a resin-to-polymer ratio of 55:45 resulting in high tackiness.

Amine-compatible pressure-sensitive adhesives based on polysiloxanes, which are, e.g., available from Dow Corning may be obtained according to the following scheme:

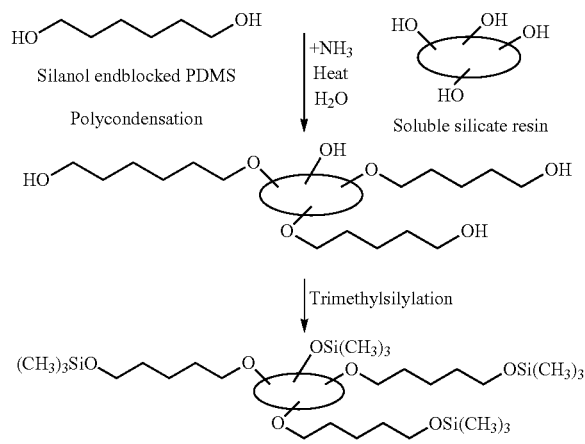

Such amine-compatible pressure-sensitive adhesives based on polysiloxanes are available from Dow Corning, e.g., under the tradenames BIO-PSA 7-4101, BIO-PSA-7-4201, or BIO-PSA 7-4301, which are provided in the solvent n-heptane (indicated by the code "01"), or under the tradenames BIO-PSA 7-4102, BIO-PSA 7-4202, and BIO 7-4302, which are provided in the solvent ethyl acetate (indicated by the code "02"). Typical solids contents in the solvent are in the range of from 60 to 75%. The code "41" indicates a resin-to-polymer ratio of 65:35 resulting in a low tackiness, the code "42" indicates a resin-to-polymer ratio of 60:40 resulting in medium tackiness, the code "43" indicates a resin-to-polymer ratio of 55:45 resulting in high tackiness.

The preferred pressure-sensitive adhesives based on polysiloxanes in accordance with the invention are characterized by a solution viscosity at 25° C. and 60% solids content in n-heptane of more than about 150 mPa s, or from about 200 mPa s to about 700 mPa s, preferably as measured using a Brookfield RVT viscometer equipped with a spindle number 5 at 50 rpm. Theses may also be characterized by a complex viscosity at 0.01 rad/s at 30° C. of less than about $1 \times 10^9$ Poise or from about $1 \times 10^5$ to about $9 \times 10^8$ Poise.

Suitable polyisobutylenes according to the invention are available under the tradename Oppanol®. Combinations of high-molecular weight polyisobutylenes (B100/B80) and low-molecular weight polyisobutylenes (B10, B11, B12, B13) may be used. Suitable ratios of low-molecular weight polyisobutylene to high-molecular weight polyisobutylene are in the range of from 100:1 to 1:100, preferably from 95:5 to 40:60, more preferably from 90:10 to 80:20. A preferred example for a polyisobutylene combination is B10/B100 in a ratio of 85/15. Oppanol® B100 has a viscosity average molecular weight $M_v$ of 1,110,000, and a weight average molecular weight $M_w$ of 1,550,000, and an average molecular weight distribution $M_w/M_n$ of 2.9. Oppanol® B10 has a viscosity average molecular weight $M_v$ of 40,000, and a weight average molecular weight $M_w$ of 53,000, and an average molecular weight distribution $M_w/M_n$ of 3.2. In certain embodiments, polybutene may be added to the polyisobutylenes. The solids content of polyisobutylenes in solvents is usually between 30 and 50%, preferably between 35 and 40%. The skilled person is aware that the solids content may be modified by adding a suitable amount of solvent.

In a preferred embodiment, the non-hybrid polymer is selected from acrylic polymers. Preferably, the acrylic polymers are pressure-sensitive adhesives based on acrylates and may also be referred to as acrylate-based pressure-sensitive adhesives, or acrylate pressure-sensitive adhesives. Pressure-sensitive adhesives based on acrylates may have a solids content preferably between 30% and 60%. Acrylic polymers, and in particular acrylate-based pressure-sensitive adhesives may or may not comprise functional groups such as hydroxy groups, carboxylic acid groups, neutralized carboxylic acid groups and mixtures thereof. Thus, the term "functional groups" in particular refers to hydroxy- and carboxylic acid groups, and deprotonated carboxylic acid groups. Preferably, the non-hybrid polymer is selected from acrylic polymers comprising hydroxyl groups and no carboxylic acid groups and more preferably is a copolymer based on vinyl acetate, 2-ethylhexyl-acrylate, 2-hydroxyethyl-acrylate and glycidyl-methacrylate.

The non-hybrid polymer may be cross-linked by a cross-linking agent and preferably may be cross-linked by a titanium cross-linking agent, or the non-hybrid polymer (non-hybrid pressure-sensitive adhesive) is not cross-linked by a cross-linking agent.

Corresponding commercial products are available e.g. from Henkel under the tradename Duro Tak®. Such acrylate-based pressure-sensitive adhesives are based on monomers selected from one or more of acrylic acid, butylacrylate, 2-ethylhexylacrylate, glycidylmethacrylate, 2-hydroxyethylacrylate, methylacrylate, methylmethacrylate, t-octylacrylamide and vinylacetate, and are provided in ethyl acetate, heptanes, n-heptane, hexane, methanol, ethanol, isopropanol, 2,4-pentanedione, toluene or xylene or mixtures thereof.

Specific acrylate-based pressure-sensitive adhesives are available as:
  Duro-Tak™ 387-2287 or Duro-Tak™ 87-2287 (a copolymer based on vinyl acetate, 2-ethylhexyl-acrylate, 2-hydroxyethyl-acrylate and glycidyl-methacrylate provided as a solution in ethyl acetate without cross-linking agent),
  Duro-Tak™ 387-2516 or Duro-Tak™ 87-2516 (a copolymer based on vinyl acetate, 2-ethylhexyl-acrylate, 2-hydroxyethyl-acrylate and glycidyl-methacrylate provided as a solution in ethyl acetate, ethanol, n-heptane and methanol with a titanium cross-linking agent),
  Duro-Tak™ 387-2051 or Duro-Tak™ 87-2051 (a copolymer based on acrylic acid, butylacrylate, 2-ethylhexylacrylate and vinyl acetate, provided as a solution in ethyl acetate and heptane),
  Duro-Tak™ 387-2353 or Duro-Tak™ 87-2353 (a copolymer based on acrylic acid, 2-ethylhexylacrylate, glycidylmethacrylate and methylacrylate, provided as a solution in ethyl acetate and hexane),
  Duro-Tak™ 87-4098 (a copolymer based on 2-ethylhexyl-acrylate and vinyl acetate, provided as a solution in ethyl acetate).

Additional polymers may also be added to enhance cohesion and/or adhesion.

Certain polymers in particular reduce the cold flow and are thus in particular suitable as additional polymer. A polymeric matrix may show a cold flow, since such polymer compositions often exhibit, despite a very high viscosity, the ability to flow very slowly. Thus, during storage, the matrix may flow to a certain extent over the edges of the backing layer. This is a problem with storage stability and can be prevented by the addition of certain polymers. A basic acrylate polymer (e.g. Eudragit® E100) may e.g. be used to reduce the cold flow. Thus, in certain embodiments, the asenapine-containing layer comprises additionally a basic polymer, in particular an amine-functional acrylate as e.g. Eudragit® E100. Eudragit® E100 is a cationic copolymer based on dimethylaminoethyl methacrylate, butyl methacrylate, and methyl methacrylate with a ratio of 2:1:1. The monomers are randomly distributed along the copolymer chain. Based on SEC method, the weight average molar mass (Mw) of Eudragit® E100 is approximately 47,000 g/mol.

Adhesion force tests were performed with the asenapine-containing adhesive matrix layer using a tensile strength testing machine. Prior testing the samples were equilibrated 24 hours under controlled conditions at approx. room temperature (23±2° C.) and approx. 50% rh (relative humidity). Further, the samples were cut into pieces with a fixed width of 25 mm and a suitable length. The first millimeters of the adhesively equipped foil was pulled off and a splicing tape is applied to the opened adhesive side. Then, the adhesively foil was totally removed and the sample was placed with the adhesive surface in longitudinal direction onto the center of the cleaned testing plate (aluminum or stainless steel). The testing plate was fixed to the lower clamp of the tensile strength machine. The machine was adjusted to zero, the splicing tape was gripped into the upper clamp of the machine. The pull angle was set to 90°. After measurement of the adhesion force of three samples, the mean value of the adhesion force was calculated. The measurement value is based on units "N/sample width" [N/25 mm].

Tack (the force which is required to separate an object from an adhesive surface after a short time of contact) tests were performed with the asenapine-containing adhesive matrix layer in accordance with the Standard Test Method for Pressure-Sensitive Tack of Adhesives Using an Inverted Probe Machine (ASTM D 2979-01; Reapproved 2009) using a probe tack tester PT-1000 (ChemInstruments). Prior to testing the samples were equilibrated 24 hours under controlled conditions at approx. room temperature (23±2° C.) and approx. 50% rh. For determining the tack, the tip of a cleaned probe with a diameter of 5 mm was brought into contact with the adhesive surface of the asenapine-containing adhesive matrix layer for 1 second, at a defined rate (10±0.1 mm/s), under defined pressure (9.79±0.10 kPa), at a given temperature (23±2° C.) and the bond formed between probe and the adhesive was subsequently broken at the same rate. Tack was measured as the maximum force required, to break the adhesion bond (see ASTM D2979-01; Reapproved 2009). After finalization the mean value from the individual results of three associated samples were calculated and the mean tack value reported in [N].

Further Additives

The TTS according to the invention, in particular the asenapine-containing layer may further comprise at least one excipient or additive. In particular, the asenapine-containing layer comprises further excipients or additives selected from the group consisting of crystallization inhibitors, cross-linking agents, solubilizers, fillers, tackifiers, film-forming agents, plasticizers, stabilizers, softeners, substances for skincare, permeation enhancers, pH regulators, and preservatives. Such additives may be present in the asenapine-containing layer in an amount of from 0.001 to 10% by weight.

It should be noted that in pharmaceutical formulations, the formulation components are categorized according to their physicochemical and physiological properties, and in accordance with their function. This means in particular that a substance or a compound falling into one category is not excluded from falling into another category of formulation component. E.g. a certain polymer can be a non-hybrid polymer but also a film-forming agent. Some substances may e.g. be a typical softener but at the same time act as a permeation enhancer. The skilled person is able to determine based on his general knowledge in which category or categories of formulation component a certain substance or compound belongs to. In the following, details on the excipients and additives are provided which are, however, not to be understood as being exclusive. Other substances not explicitly listed in the present description may be as well used in accordance with the present invention, and substances and/or compounds explicitly listed for one category of formulation component are not excluded from being used as another formulation component in the sense of the present invention.

The cross-linking agent in particular may be selected from the group consisting of aluminium and titanium cross-linking agents such as aluminium acetylacetonate, titanium acetylacetonate or polybutyltitanate, and preferably is a titanium cross-linking agent. The amount of cross-linking agent may range from 0.005 to 1%, and preferably from 0.01 to 0.1% of the asenapine-containing layer. The asenapine-containing layer may also comprise a polymer which is self-crosslinking, i.e. comprises a cross-linking functional group such as glycidyl groups, which reacts upon heating. According to a further specific embodiment, the asenapine-containing layer comprises a cross-linking agent as above and a self-crosslinking polymer.

In one embodiment, the asenapine-containing layer further comprises a crystallization inhibitor. Suitable examples of crystallization inhibitors include polyvinylpyrrolidone, vinyl acetate/vinylpyrrolidone copolymer and cellulose derivatives. The crystallization inhibitor is preferably polyvinylpyrrolidone, more preferably soluble polyvinylpyrrolidone. The crystallization inhibitor may increase the solubility of the active agent or inhibit the crystallization of the active agent.

The term "soluble polyvinylpyrrolidone" refers to polyvinylpyrrolidone which is soluble with more than 10% in at least ethanol, preferably also in water, diethylene glycol, methanol, n-propanol, 2-propanol, n-butanol, chloroform, methylene chloride, 2-pyrrolidone, macrogol 400, 1,2 propylene glycol, 1,4 butanediol, glycerol, triethanolamine, propionic acid and acetic acid. Examples of polyvinylpyrrolidones which are commercially available include Kollidon® 12 PF, Kollidon® 17 PF, Kollidon® 25, Kollidon® 30 and Kollidon® 90 F supplied by BASF, or povidone K90F.

In one embodiment, the asenapine-containing layer further comprises a stabilizer, wherein the stabilizer is preferably selected from tocopherol and ester derivatives thereof and ascorbic acid and ester derivatives thereof. Preferred stabilizers include tocopherol and ester derivatives thereof, ascorbic acid and ester derivatives thereof, butylated hydroxyanisol and butylated hydroxytoluene. Particularly preferred is tocopherol.

In one embodiment, the asenapine-containing layer further comprises a softener. Exemplary softeners include linear or branched, saturated or unsaturated alcohols having 6 to 20 carbon atoms.

In case the asenapine-containing layer is required to have self-adhesive properties and one or more polymers is/are selected which does/do not provide sufficient self-adhesive properties, a tackifier is added. The tackifier may be selected from polyvinyl alcohol, alginate, guar gum, triglycerides, dipropylene glycol, resins, resin esters, terpenes and derivatives thereof, ethylene vinyl acetate adhesives, dimethylpolysiloxanes and polybutenes.

In certain embodiments, the asenapine-containing layer comprises a film-forming agent selected from polyvinylpyrrolidone and in particular soluble polyvinylpyrrolidone, Soluplus® (Soluplus® is a polyethylene glycol, polyvinyl acetate and polyvinylcaprolactame-based graft copolymer, also abbreviated as PVAc-PVCap-PEG), polyethylene glycol, cellulose derivatives and other hydrophilic additives. Soluplus may be selected from polyethylene glycol, polyvinyl acetate and polyvinylcaprolactame-based graft copolymers (PVAc-PVCap-PEG).

In certain embodiments, the asenapine-containing layer comprises a permeation enhancer. Permeation enhancers are substances, which influence the barrier properties of the stratum corneum in the sense of increasing the active agent permeability. Some examples of permeation enhancers are polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin; polar solvents such as dimethyldecylphosphoxide, methylcetylsulfoxide, dimethylaurylamine, dodecyl pyrrolidone, isosorbitol, dimethylacetonide, dimethylsulfoxide, decylmethylsulfoxide, and dimethylformamide; salicylic acid; amino acids; benzyl nicotinate; and higher molecular weight aliphatic surfactants such as lauryl sulfate salts. Other agents include oleic and linoleic acids, ascorbic acid, panthenol, butylated hydroxytoluene, tocopherol, tocopheryl acetate, tocopheryl linoleate, propyl oleate, and isopropyl palmitate. Preferably, the permeation enhancer is selected from diethylene glycol monoethyl ether, diisopropyl adipate, isopropyl myristate, isopropyl palmitate, lauryl lactate, dimethylpropylene urea and a mixture of propylene glycol monoesters and diesters of fatty acids.

It has been found that the TTS provides sufficient permeability of the asenapine even if no permeation enhancer is present. Therefore, in certain embodiments of the invention, the asenapine-containing layer does not comprise a permeation enhancer.

The asenapine-containing layer according to the invention may comprise a solubilizer. The solubilizer is preferably selected from polyhydric alcohols such as 1,2-propanediol, various butanediols, glycerol, polyethylene glycol 400, tetrahydrofurfuryl alcohol and diethylene glycol monoethyl ether. Furthermore respective permeation enhancers may also act as a solubilizer.

Fillers such as silica gels, titanium dioxide and zinc oxide may be used in conjunction with the polymer in order to influence certain physical parameters, such as cohesion and bond strength, in the desired way.

The asenapine-containing layer according to the invention may comprise a plasticizer. Preferably, the plasticizer is selected from glycerol, glycerol esters, glycol derivatives, fatty acid ester, acid ester and sugar alcohols.

The asenapine-containing layer according to the invention may comprise a softener. Preferably, the softener is selected from linear or branched, saturated or unsaturated alcohols and triclycerides having 6 to 20 carbon atoms.

The asenapine-containing layer according to the invention may comprise a substance for skincare. Preferably, the substance for skincare is selected from dexpanthenol, lecithin, phosphatides, cholesterol, aloe.

The asenapine-containing layer according to the invention may comprise a pH regulator. Preferably, the pH regulator is selected from amine derivatives, inorganic alkali derivatives, polymers with basic and acidic functionality, respectively.

In general, it is preferred according to the invention that no further additives are required. Thus, the TTS has a structure of low complexity.

Release Characteristics

The TTS in accordance with the invention are designed for transdermally administering asenapine to the systemic circulation for a predefined extended period of time.

In one aspect, the TTS according to the invention provide a mean release rate of 0.5 to 20 mg/day, preferably of 1.0 to 15 mg/day, and more preferably of 2.0 to 10 mg/day over at least 24 hours of administration, preferably over at least 48 hours of administration, more preferably over at least 72 hours of administration.

According to certain embodiments, the TTS according to the invention provide a cumulative skin permeation rate of asenapine at hour 48 or at hour 72 as measured in a Franz diffusion cell with dermatomed human skin of 1 µg/cm²-hr to 20 µg/cm²-hr, preferably of 2 µg/cm²-hr to 17 µg/cm²-hr and more preferably of 4 µg/cm²-hr to 12 µg/cm²-hr.

In specific embodiments of the invention, the TTS according to the invention as described above provides a skin permeation rate of asenapine as measured in a Franz diffusion cell with dermatomed human skin of
0 µg/cm²-hr to 10 µg/cm²-hr in the first 8 hours,
2 µg/cm²-hr to 20 µg/cm²-hr from hour 8 to hour 24,
5 µg/cm²-hr to 25 µg/cm²-hr from hour 24 to hour 32,
3 µg/cm²-hr to 22 µg/cm²-hr from hour 32 to hour 48,
2 µg/cm²-hr to 20 µg/cm²-hr from hour 48 to hour 72.

In certain embodiments, the transdermal therapeutic system according to the invention provides a cumulative permeated amount of asenapine as measured in a Franz diffusion cell with dermatomed human skin of 0.05 mg/cm² to 1.0 mg/cm², preferably of 0.1 mg/cm² to 0.8 mg/cm² over a time period of 48 hours.

In certain embodiments, the transdermal therapeutic system according to the invention provides a cumulative permeated amount of asenapine as measured in a Franz diffusion cell with dermatomed human skin of 0.1 mg/cm² to 2.0 mg/cm², preferably 0.2 mg/cm² to 1.2 mg/cm² over a time period of 72 hours.

Further, in certain embodiments, the present invention is related to a transdermal therapeutic system by transdermal providing by transdermal delivery one or more pharmacokinetic parameter(s) selected from the group consisting of an $AUC_{0-48}$ from 20 to 300 (ng/mL) hr, preferably from 30 to 200 (ng/mL) hr, an $AUC_{0-72}$ from 30 to 400 (ng/mL) hr, preferably from 50 to 300 (ng/mL) hr, an $AUC_{0-84}$ from 35 to 450 (ng/mL) hr, preferably from 60 to 350 (ng/mL) hr, a $C_{max}$ to $C_{48}$ ratio of less than 2.0, preferably of less than 1.5 and more preferably of less than 1.3, a $C_{max}$ to $C_{72}$ ratio of less than 3.0, preferably of less than 2.5 and more preferably of less than 2.0, a $C_{max}$ to $C_{84}$ ratio of less than 3.5, preferably of less than 3.0, more preferably of less than 2.5 and most preferably of less than 2.0.

Method of Treatment/Medical Use

In accordance with a specific aspect of the present invention, the TTS according to the invention is for use in a method of treatment. In particular, the TTS according to the invention is for use in a method of treating a human patient.

In certain embodiments, the TTS according to the invention is for use in a method of treating schizophrenia and/or bipolar disorder. In particular, the TTS according to the invention is for use in a method of treating bipolar disorder, and in particular for use in a method of treating acute manic or mixed episodes of bipolar disorder.

The TTS may be further for use in a method of treatment with a dosing interval of at least 24 hours or 1 day, at least 48 hours or 2 days, or at least 72 hours or 3 days. Further, the TTS may be for use in a method of treatment with a dosing interval of up to 168 hours or 7 days, up to 120 hours or 5 days, or up to 96 hours or 4 days. The dosing interval may in particular be 24 hours or 1 day, 48 hours or 2 days, or 84 hours or 3.5 days.

Accordingly the invention is also related to TTS for use in a method of treatment, and in particular for use in a method of treating schizophrenia and/or bipolar disorder, and in particular acute manic or mixed episodes of bipolar disorder, in an around-the-clock treatment with a once-a-day TTS exchange mode (dosing interval of 24 hours or 1 day), a twice-a-week TTS exchange mode (dosing interval of 84 hours or 3.5 days) or a once-a-week TTS exchange mode (dosing interval of 168 hours or 7 days).

In accordance with another specific aspect, the present invention is also related to a method of treatment, and in particular a method of treating a human patient.

The invention is in particular related to a method of treatment, including applying a transdermal therapeutic system according to the invention to the skin of a patient.

The invention is in particular related to a method of treating schizophrenia and/or bipolar disorder, including applying a transdermal therapeutic system according to the invention to the skin of a patient.

The invention is in particular related to a method of treating bipolar disorder and in particular acute manic or mixed episodes of bipolar disorder including applying a transdermal therapeutic system according to the invention to the skin of a patient.

The method of treatment as outlined above may in particular include applying a transdermal therapeutic system according to the invention for at least 24 hours or 1 day, at least 48 hours or 2 days, or at least 72 hours or 3 days to the skin of a patient.

The method of treatment as outlined above may also include applying a transdermal therapeutic system according to the invention for up to 168 hours or 7 days, up to 120 hours or 5 days, or up to 96 hours or 4 days to the skin of a patient. Specifically, the method of treatment as outlined above may in particular include applying a transdermal therapeutic system according to the invention for 24 hours or 1 day, 48 hours or 2 days, or 84 hours or 3.5 days to the skin of a patient.

Accordingly, the invention is also related to a method of treatment in an around-the-clock treatment with a once-a-day TTS exchange mode (dosing interval of 24 hours or 1 day), a twice-a-week TTS exchange mode (dosing interval of 84 hours or 3.5 days) or a once-a-week TTS exchange mode (dosing interval of 168 hours or 7 days).

The inventors have surprisingly shown that a relatively constant asenapine blood plasma concentration can be maintained for an extended period of time by transdermal delivery of asenapine.

Process of Manufacture

The invention further relates to a process of manufacture of an asenapine-containing layer for use in a transdermal therapeutic system and a corresponding asenapine-containing layer structure and a corresponding TTS.

The process of manufacture of an asenapine-containing layer for use in a transdermal therapeutic system according to the invention comprises the steps of:

1) combining at least the components asenapine and a silicone acrylic hybrid polymer in a solvent to obtain a coating composition;
2) coating the coating composition onto the backing layer or release liner; and
3) drying the coated coating composition to form the asenapine-containing layer.

In this process of manufacture, the silicone acrylic hybrid polymer is preferably provided as a solution in ethyl acetate or in n-heptane, preferably in ethyl acetate.

In this process of manufacture, preferably in step 1) the asenapine is dissolved to obtain a coating composition.

In the above described process, preferably the solvent is selected from alcoholic solvents, in particular methanol, ethanol, isopropanol and mixtures thereof, and from non-alcoholic solvents, in particular ethyl acetate, hexane, n-heptane, petroleum ether, toluene, and mixtures thereof, and more preferably is selected from n-heptane and ethyl acetate.

In certain embodiments, the silicone acrylic hybrid polymer is provided as a solution in ethyl acetate, n-heptane, methanol or ethanol with a solids content of from 30 to 70% by weight. Preferably, silicone acrylic hybrid polymer is provided as a solution in ethyl acetate or n-heptane a solids content of from 40 to 60% by weight.

In step 3), drying is performed preferably at a temperature of from 40 to 90° C., more preferably from 50 to 80° C.

EXAMPLES

The present invention will now be more fully described with reference to the accompanying examples. It should be understood, however, that the following description is illustrative only and should not be taken in any way as a restriction of the invention. Numerical values provided in the examples regarding the amount of ingredients in the composition or the area weight may vary slightly due to manufacturing variability.

Examples 1a, 1b and Reference Example 1c

Coating Composition

The formulations of the asenapine-containing coating compositions of Examples 1a, 1b and Reference Example 1c are summarized in Table 1.1 below. The formulations are based on weight percent as also indicated in Table 1.1.

TABLE 1.1

| Ingredient (Trade Name) | Ex. 1a Amt [g] | Ex. 1a Solids [%] | Ex. 1b Amt [g] | Ex. 1b Solids [%] | Ref. Ex. 1c Amt [g] | Ref. Ex. 1c Solids [%] |
|---|---|---|---|---|---|---|
| Asenapine base | 0.34 | 6.70 | 0.34 | 6.81 | 0.33 | 6.61 |
| Silicone acrylic hybrid pressure-sensitive adhesive in n-Hexane. Solids content of about 50% by weight (Dow-Corning ® 7-6301) | 9.37 | 93.30 | — | — | — | — |

TABLE 1.1-continued

| Ingredient (Trade Name) | Ex. 1a Amt [g] | Ex. 1a Solids [%] | Ex. 1b Amt [g] | Ex. 1b Solids [%] | Ref. Ex. 1c Amt [g] | Ref. Ex. 1c Solids [%] |
|---|---|---|---|---|---|---|
| Silicone acrylic hybrid pressure-sensitive adhesive in ethyl acetate. Solids content of about 50% by weight (Dow-Corning ® 7-6302) | — | — | 9.31 | 93.19 | — | — |
| Acrylic adhesive in ethyl acetate. Solids content of 50.5% by weight (Duro-Tak ™ 387-2287) | — | — | — | — | 9.24 | 93.39 |
| Ethyl acetate | — | — | — | — | 2.06 | — |
| Total | 9.71 | 100.00 | 9.65 | 100.00 | 11.63 | 100.00 |
| Area Weight [g/m²] | 101.70 | | 109.85 | | 102.50 | |
| Asenapine content [mg/cm²] | 0.681 | | 0.737 | | 0.677 | |

Preparation of the Coating Composition

A beaker was loaded with the asenapine base and with the solvent (ethyl acetate), if applicable (Reference Example 1c). The acrylic pressure-sensitive adhesive Duro-Tak™ 387-2287 (Reference Example 1c) or the Silicone acrylic hybrid pressure-sensitive adhesive 7-6301 (Example 1a) or 7-6302 (Example 1b) was added and the mixture was then stirred at up to 500 rpm until a homogeneous mixture was obtained (stirring time is 60 min. or longer throughout the examples, if not indicated otherwise).

Coating of the Coating Composition

The resulting asenapine-containing coating composition was coated on a polyethylene terephthalate film (siliconised, 100 μm thickness (Reference Example 1c) or fluoropolymerised, 75 μm thickness (Examples 1a, 1b) which may function as release liner) and dried for approx. 10 min at room temperature and 20 min at 60° C. (Example 1b and Reference Example 1c) or 90° C. (Example 1a). The coating thickness gave an area weight of the asenapine-containing pressure-sensitive adhesive layer of 101.70 g/m² (Example 1a), 109.85 g/m² (Example 1 b), and 102.50 g/m² (Reference Example 1c), respectively. The dried film was laminated with a polyethylene terephthalate backing layer (23 μm thickness) to provide an asenapine-containing self-adhesive layer structure.

Preparation of the TTS (Concerning all Examples)

The individual systems (TTS) were then punched out from the asenapine-containing self-adhesive layer structure. In specific embodiments a TTS as described above can be provided with a further self-adhesive layer of larger surface area, preferably with rounded corners, comprising a pressure-sensitive adhesive matrix layer which is free of active agent. This is of advantage when the TTS, on the basis of its physical properties alone, does not adhere sufficiently to the skin and/or when the asenapine-containing matrix layer, for the purpose of avoiding waste, has pronounced corners (square or rectangular shapes). The TTS are then punched out and sealed into pouches of the primary packaging material.

Measurement of Skin Permeation Rate

Figure 1A:
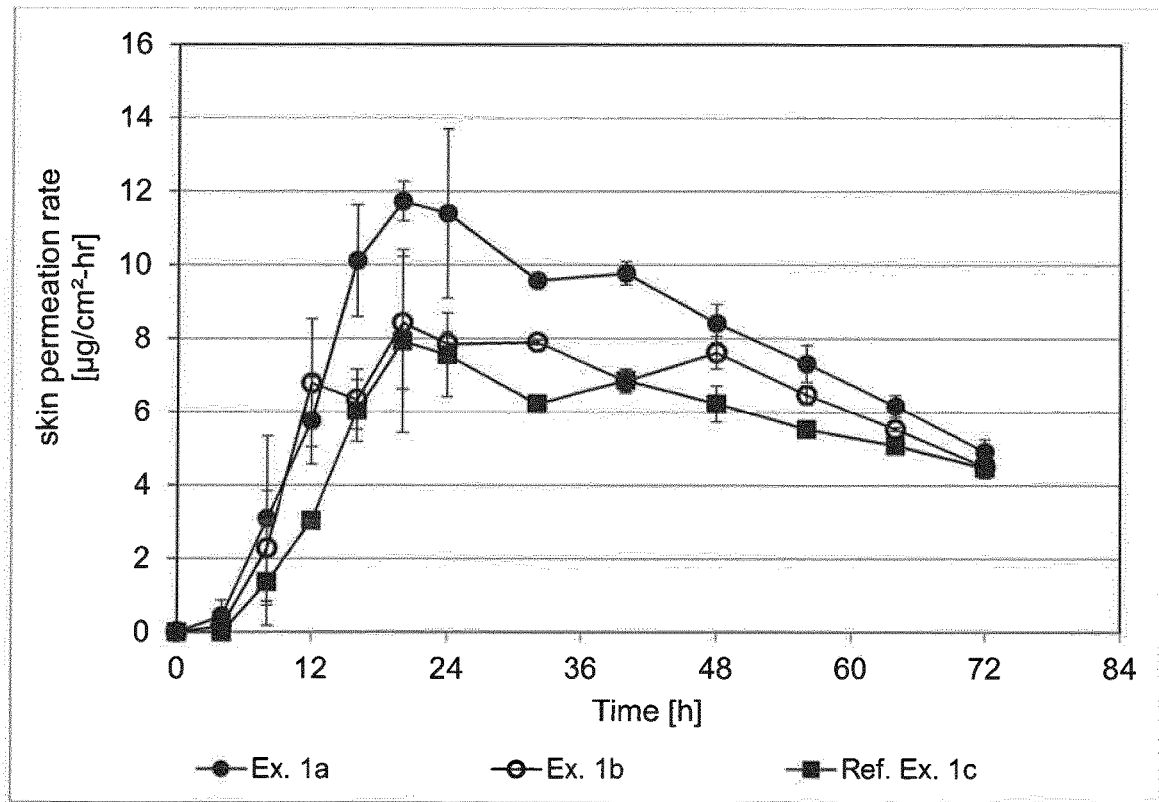
FIG. 1a depicts the asenapine skin permeation rate of TTS prepared according to Ex. 1a, Ex. 1b, and Ref. Ex. 1c for hours 0 to 72.

The permeated amount and the corresponding skin permeation rates of TTS prepared according to Examples 1a, 1b, and Reference Example 1c were determined by in vitro experiments in accordance with the OECD Guideline (adopted Apr. 13, 2004) carried out with a 7.0 ml Franz diffusion cell. Split thickness Goettingen minipig skin (female) was used. A dermatome was used to prepare skin to a thickness of 800 μm, with an intact epidermis for all TTS. Diecuts with an area of 1.145 cm² were punched from the TTS. The asenapine permeated amount in the receptor medium of the Franz cell (phosphate buffer solution pH 5.5 with 0.1% saline azide as antibacteriological agent,) at a temperature of 32±1° C. was measured and the corresponding skin permeation rate calculated. The results are shown in Table 1.2 and FIG. 1a.

TABLE 1.2

| | Skin permeation rate with SD [μg/cm²-hr] | | | | | |
|---|---|---|---|---|---|---|
| Elapsed time [h] | Ex. 1a (n = 3) | | Ex. 1b (n = 2) | | Ref. Ex. 1c (n = 2) | |
| | Rate | SD | Rate | SD | Rate | SD |
| 0 | 0 | 0 | 0 | 0 | 0 | 0 |
| 4 | 0.44 | 0.43 | 0.17 | 0.24 | 0 | 0 |
| 8 | 3.09 | 2.25 | 2.29 | 1.56 | 1.36 | 1.18 |
| 12 | 5.76 | 1.19 | 6.79 | 1.75 | 3.04 | 0.2 |
| 16 | 10.11 | 1.51 | 6.34 | 0.83 | 6.03 | 0.85 |
| 20 | 11.72 | 0.54 | 8.43 | 1.8 | 7.92 | 2.49 |
| 24 | 11.40 | 2.29 | 7.86 | 0.32 | 7.56 | 1.14 |
| 32 | 9.57 | 0.01 | 7.90 | 0.06 | 6.22 | 0.22 |
| 40 | 9.78 | 0.32 | 6.85 | 0.33 | 6.87 | 0.3 |
| 48 | 8.42 | 0.51 | 7.62 | 0.44 | 6.22 | 0.49 |
| 56 | 7.33 | 0.5 | 6.47 | 0.27 | 5.52 | 0.24 |
| 64 | 6.17 | 0.3 | 5.53 | 0.05 | 5.08 | 0.08 |
| 72 | 4.92 | 0.33 | 4.51 | 0.03 | 4.47 | 0.28 |

Utilization of Asenapine

Figure 1B:
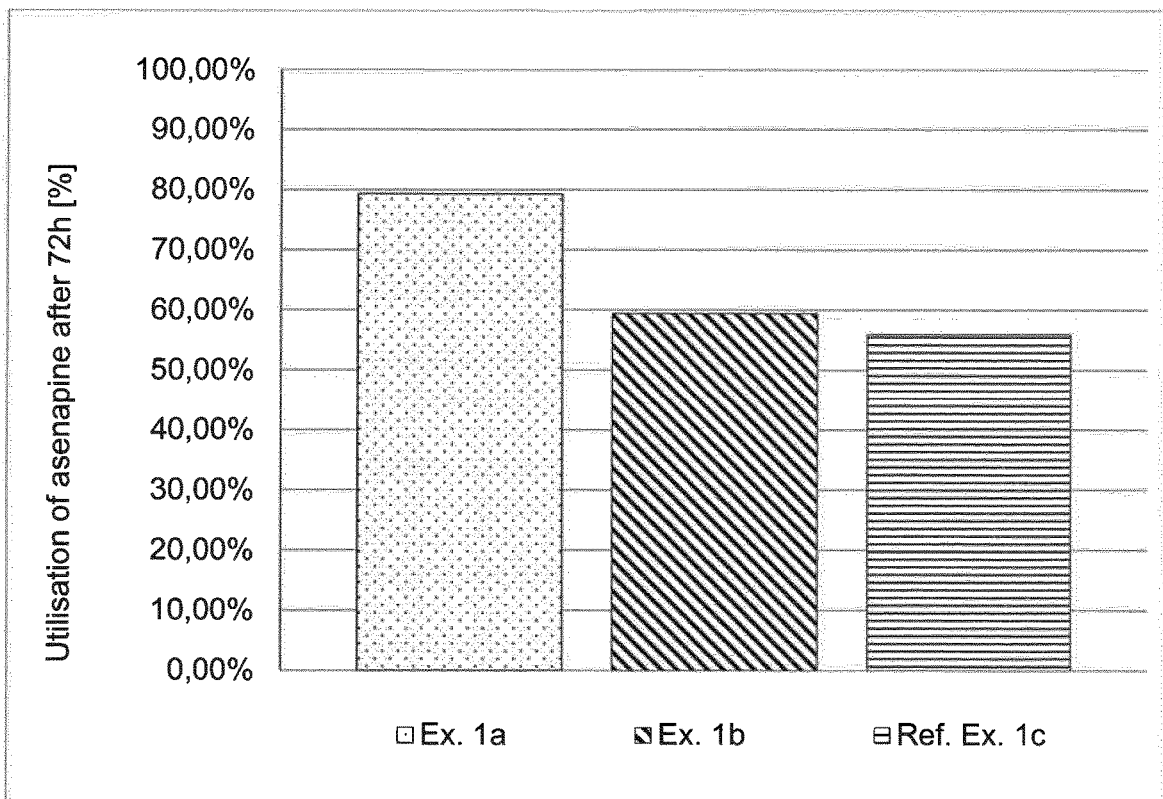
FIG. 1b depicts the utilisation of asenapine of TTS prepared according to Ex. 1a, Ex. 1b, and Ref. Ex. 1c after 72 h.

The utilization of asenapine at 72 hours was calculated based on the cumulative permeated amount at 72 hours and the initial asenapine content. The results are shown in Table 1.3 and in FIG. 1b.

TABLE 1.3

| Utilization of asenapine after 72 h [%] | | |
|---|---|---|
| Example 1a (n = 3) | Example 1b (n = 3) | Reference Example 1c (n = 3) |
| 79.36 | 59.46 | 55.92 |

Examples 2A and Reference Example 2B

Coating Composition

The formulations of the asenapine-containing coating compositions of Example 2a and Reference Example 2b are summarized in Table 2.1 below. The formulations are based on weight percent, as also indicated in Table 2.1.

TABLE 2.1

| Ingredient (Trade Name) | Ex. 2a Amt [g] | Ex. 2a Solids [%] | Ref. Ex. 2b Amt [g] | Ref. Ex. 2b Solids [%] |
|---|---|---|---|---|
| Asenapine base | 0.68 | 13.40 | 0.68 | 13.59 |
| Silicone acrylic hybrid pressure-sensitive adhesive in ethyl acetate. Solids content of about 50% by weight (Dow-Corning ® 7-6302) | 8.79 | 86.60 | — | — |

TABLE 2.1-continued

| Ingredient (Trade Name) | Ex. 2a Amt [g] | Ex. 2a Solids [%] | Ref. Ex. 2b Amt [g] | Ref. Ex. 2b Solids [%] |
|---|---|---|---|---|
| Acrylic adhesive in ethyl acetate. Solids content of 50.5% by weight (Duro-Tak ™ 387-2287) | — | — | 8.56 | 86.41 |
| Ethyl acetate | — | — | 2.37 | — |
| Total | 9.47 | 100.00 | 11.61 | 100.00 |
| Area Weight [g/m$^2$] | 117.50 | | 97.80 | |
| Asenapine content [mg/cm$^2$] | 1.570 | | 1.328 | |

Preparation of the Coating Composition

For Example 2a and Reference Example 2b, the coating compositions were prepared as described in Example 1b and Reference Example 1c.

Coating of the Coating Composition

The resulting asenapine-containing coating composition was coated on a polyethylene terephthalate film (siliconised, 100 μm thickness (Reference Example 2b) or fluoropolymerised, 75 μm thickness (Example 2a), which may function as release liner) and dried for approx. 10 min at room temperature and 20 min at 60° C. (Example 2a and Reference Example 2b). The coating thickness gave an area weight of the asenapine-containing pressure-sensitive adhesive layer of 117.50 g/m$^2$ (Example 2a) and 97.80 g/m$^2$ (Reference Example 2b), respectively. The dried film was laminated with a polyethylene terephthalate backing layer (23 μm thickness) to provide an asenapine-containing self-adhesive layer structure.

Preparation of the TTS

See Example 1.

Measurement of Skin Permeation Rate

The permeated amount and the corresponding skin permeation rates of TTS prepared according to Example 2a and Reference Example 2b were determined by in vitro experiments in accordance with the OECD Guideline (adopted Apr. 13, 2004) carried out with a 7.0 ml Franz diffusion cell. Split thickness Goettingen minipig skin (female) was used. A dermatome was used to prepare skin to a thickness of 800 with an intact epidermis for all TTS. Diecuts with an area of 1.145 cm$^2$ were punched from the TTS. The asenapine permeated amount in the receptor medium of the Franz cell (solution containing 60% phosphate buffer pH 5.5, 30% dipropylene glycol, 10% acetonitrile) at a temperature of 32±1° C. was measured and the corresponding skin permeation rate calculated. The results are shown in Table 2.2 and FIG. 2a.

TABLE 2.2

Skin permeation rate with SD [μg/cm$^2$-hr]

| Elapsed time [h] | Ex. 2a (n = 3) Rate | Ex. 2a (n = 3) SD | Ref. Ex. 2b (n = 2) Rate | Ref. Ex. 2b (n = 2) SD |
|---|---|---|---|---|
| 0 | 0 | 0 | 0 | 0 |
| 4 | 0.64 | 0.17 | 1.04 | 0.24 |
| 8 | 4.50 | 0.6 | 6.30 | 1.93 |
| 12 | 9.40 | 1.69 | 9.04 | 0.46 |
| 16 | 12.51 | 1.21 | 12.17 | 1.97 |
| 20 | 13.72 | 2.18 | 14.71 | 1.66 |
| 24 | 15.84 | 0.89 | 18.98 | 2.5 |
| 32 | 13.13 | 0.26 | 15.29 | 1.35 |
| 40 | 13.59 | 0.49 | 14.84 | 1.04 |
| 48 | 12.53 | 0.41 | 13.30 | 0.83 |
| 56 | 11.06 | 0.76 | 11.68 | 0.26 |
| 64 | 9.94 | 0.68 | 10.35 | 0.12 |
| 72 | 8.95 | 0.51 | 8.89 | 0.07 |

Utilization of Asenapine

The utilization of asenapine at 72 hours was calculated based on the cumulative permeated amount at 72 hours and the initial asenapine content. The results are shown in Table 2.3 and in FIG. 2b.

TABLE 2.3

Utilization of asenapine after 72 h %

| Example 2a (n = 3) | Reference Example 2b (n = 2) |
|---|---|
| 49.67 | 63.55 |

Examples 3A and Reference Example 3B

Coating Composition

The formulations of the asenapine-containing coating compositions of Example 3a and Reference Example 3b are summarized in Table 3.1 below. The formulations are based on weight percent, as also indicated in Table 3.1.

TABLE 3.1

| Ingredient (Trade Name) | Ex. 3a Amt [g] | Ex. 3a Solids [%] | Ref. Ex. 3b Amt [g] | Ref. Ex. 3b Solids [%] |
|---|---|---|---|---|
| Asenapine base | 3.60 | 17.73 | 3.61 | 18.00 |
| Silicone acrylic hybrid pressure-sensitive adhesive in ethyl acetate. Solids content of about 50% by weight (Dow-Corning ® 7-6302) | 33.42 | 82.27 | — | — |
| Acrylic adhesive in ethyl acetate. Solids content of 50.5% by weight (Duro-Tak ™ 387-2287) | — | — | 32.57 | 82.00 |
| Ethyl acetate | 2.47 | — | 10.44 | — |
| Total | 39.49 | 100.00 | 46.62 | 100.00 |
| Area Weight [g/m$^2$] | 174.50 | | 148.60 | |
| Asenapine content [mg/cm$^2$] | 3.090 | | 2.672 | |

Preparation of the Coating Composition

The coating composition of Example 3a and Reference Example 3b was prepared as described in Reference Example 1c, but stirred at up to 1000 rpm for Example 3a.

Coating of the Coating Composition

The resulting asenapine-containing coating composition was coated on a polyethylene terephthalate film (siliconised, 100 μm thickness (Reference Example 3b) or fluoropolymerised, 75 μm thickness (Example 3a) which may function as release liner) and dried for approx. 15 min at room temperature and 25 min at 60° C.). The coating thickness gave an area weight of the asenapine-containing pressure-sensitive adhesive layer of 174.50 g/m$^2$ (Example 3a) and 148.60 g/m$^2$ (Reference Example 3b), respectively. The dried film was laminated with a polyethylene terephthalate backing layer (23 µm thickness) to provide an asenapine-containing self-adhesive layer structure.

Preparation of the TTS

See Example 1.

Measurement of Skin Permeation Rate

The permeated amount and the corresponding skin permeation rates of TTS prepared according to Example 3a and Reference Examples 3b were determined by in vitro experiments in accordance with the OECD Guideline (adopted Apr. 13, 2004) carried out with a 7.0 ml Franz diffusion cell. Split thickness Goettingen minipig skin was used. A dermatome was used to prepare skin to a thickness of 800 µm, with an intact epidermis for all TTS. Diecuts with an area of 1.156 cm$^2$ were punched from the TTS. The asenapine permeated amount in the receptor medium of the Franz cell (phosphate buffer solution pH 5.5 with 0.1% saline azide as antibacteriological agent) at a temperature of 32±1° C. was measured and the corresponding skin permeation rate calculated. The results are shown in Table 3.2 and FIGS. 3a and 3b.

TABLE 3.2

Skin permeation rate with SD [µg/cm$^2$-hr]

| Elapsed time [h] | Ex. 3a (n = 3) Rate | SD | Ref. Ex. 3b (n = 3) Rate | SD |
|---|---|---|---|---|
| 0 | 0 | 0 | 0 | 0 |
| 4 | 2.05 | 1.09 | 1.71 | 0.31 |
| 8 | 7.51 | 2.61 | 6.95 | 0.54 |
| 12 | 12.04 | 3.07 | 10.46 | 1.73 |
| 16 | 14.56 | 3.03 | 12.35 | 6.12 |
| 20 | 15.88 | 2.28 | 13.90 | 3.42 |
| 24 | 16.86 | 2.43 | 16.44 | 4.83 |
| 32 | 15.83 | 1.99 | 14.24 | 2.55 |
| 40 | 16.27 | 1.82 | 14.73 | 2.81 |
| 48 | 15.59 | 1.76 | 15.06 | 2.79 |
| 56 | 15.16 | 1.04 | 14.13 | 1.94 |
| 64 | 14.55 | 0.11 | 13.79 | 1.25 |
| 72 | 14.50 | 0.61 | 13.66 | 1.01 |
| 96 | 10.83 | 1.32 | 10.19 | 0.94 |
| 120 | 9.80 | 1.05 | 9.66 | 0.65 |
| 144 | 8.40 | 0.1 | 7.96 | 0.3 |
| 168 | 7.82 | 1.16 | 6.99 | 0.33 |

Utilization of Asenapine

The utilization of asenapine at 72 hours and 168 hours was calculated based on the cumulative permeated amount at 72 hours and 168 hours and the initial asenapine content. The results are shown in Table 3.3 and in FIG. 3c.

TABLE 3.3

Utilization of asenapine after 72 h and after 168 h [%]

| Example 3a- 72 h (n = 3) | Example 3a- 168 h (n = 3) | Ref. Ex. 3b- 72 h (n = 3) | Ref. Ex. 3b- 168 h (n = 3) |
|---|---|---|---|
| 32.71 | 61.34 | 30.16 | 66.16 |

Examples 4A and Reference Example 4B

Coating Composition

The formulations of the asenapine-containing coating compositions of Example 4a and Reference Example 4b are summarized in Table 4.1 below. The formulations are based on weight percent, as also indicated in Table 4.1.

TABLE 4.1

| Ingredient (Trade Name) | Ex. 4a Amt [g] | Ex. 4a Solids [%] | Ref. Ex. 4b Amt [g] | Ref. Ex. 4b Solids [%] |
|---|---|---|---|---|
| Asenapine base | 4.01 | 16.38 | 4.00 | 16.48 |
| Silicone acrylic hybrid pressure-sensitive adhesive in ethyl acetate. Solids content of about 50% by weight (Dow-Corning ® 7-6302) | 40.23 | 83.62 | — | — |
| Acrylic adhesive in ethyl acetate. Solids content of 50.5% by weight (Duro-Tak ™ 387-2287) | — | — | 40.16 | 83.52 |
| Ethyl acetate | 4.52 | — | 12.32 | — |
| Total | 48.76 | 100.00 | 56.48 | 100.00 |
| Area Weight [g/m$^2$] | 138.20 | | 135.70 | |
| Asenapine content [mg/cm$^2$] | 2.263 | | 2.237 | |

Preparation of the Coating Composition

For Example 4a and Reference Example 4b, a beaker was loaded with the asenapine base and with the solvent (ethyl acetate). The respective pressure-sensitive adhesive was added and the mixture was then stirred at approx. 500 rpm until a homogeneous mixture was obtained.

Coating of the Coating Composition

See resulting asenapine-containing coating composition was coated on a polyethylene terephthalate film (siliconised, 100 µm thickness (Reference Example 4b) or fluoropolymerised, 75 µm thickness (Example 4a)), which may function as release liner) and dried for approx. 15 min at room temperature and 25 min at 60° C. The coating thickness gave an area weight of the asenapine-containing pressure-sensitive adhesive layer of 138.20 g/m$^2$ (Example 4a) and 135.7 g/m$^2$ (Reference Example 4b). The dried film was laminated with a polyethylene terephthalate backing layer (23 µM thickness) to provide an asenapine-containing self-adhesive layer structure.

Preparation of the TTS

See Example 1.

Measurement of Skin Permeation Rate

The permeated amount and the corresponding skin permeation rates of TTS prepared according to Example 4a and Reference Example 4b were determined by in vitro experiments in accordance with the OECD Guideline (adopted Apr. 13, 2004) carried out with a 7.0 ml Franz diffusion cell. Split thickness Goettingen minipig skin (female) was used. A deimatome was used to prepare skin to a thickness of 800 µm, with an intact epidermis for all TTS. Diecuts with an area of 1.156 cm$^2$ were punched from the TTS. The asenapine permeated amount in the receptor medium of the Franz cell (phosphate buffer solution pH 5.5 with 0.1% saline azide as antibacteriological agent) at a temperature of 32±1° C. was measured and the corresponding skin permeation rate calculated. The results are shown in Table 4.2 and FIGS. 4a and 4b.

TABLE 4.2

Skin permeation rate with SD [µg/cm$^2$-hr]

| Elapsed time [h] | Ex. 4a (n = 3) Rate | SD | Ref. Ex. 4b (n = 3) Rate | SD |
|---|---|---|---|---|
| 0 | 0 | 0 | 0 | 0 |
| 4 | 0.77 | 0.43 | 0.45 | 0.09 |
| 8 | 7.01 | 3.13 | 3.96 | 0.79 |

TABLE 4.2-continued

Skin permeation rate with SD [µg/cm²-hr]

| Elapsed time [h] | Ex. 4a (n = 3) | | Ref. Ex. 4b (n = 3) | |
|---|---|---|---|---|
| | Rate | SD | Rate | SD |
| 12 | 12.05 | 1.78 | 8.65 | 1 |
| 16 | 17.39 | 4.51 | 11.62 | 0.59 |
| 20 | 18.21 | 3.99 | 13.53 | 0.83 |
| 24 | 20.14 | 3.11 | 15.27 | 0.75 |
| 32 | 18.22 | 2.43 | 13.36 | 0.52 |
| 40 | 18.69 | 2 | 14.68 | 0.49 |
| 48 | 17.57 | 1.44 | 14.89 | 0.37 |
| 56 | 16.87 | 1.02 | 14.60 | 0.6 |
| 64 | 15.72 | 1.27 | 14.67 | 0.47 |
| 72 | 14.63 | 1.44 | 13.54 | 0.14 |
| 96 | 10.56 | 0.18 | 9.95 | 0.12 |
| 120 | 8.12 | 0.71 | 9.36 | 0.13 |
| 144 | 5.75 | 1.1 | 7.73 | 0.18 |
| 168 | 4.13 | 0.86 | 6.20 | 0.18 |

Utilization of Asenapine

The utilization of asenapine at 72 h and 168 h was calculated based on the cumulative permeated amount at 72 h and the initial asenapine content. The results are shown in Table 4.3 and in FIG. 4c.

TABLE 4.3

Utilization of asenapine after 72 hours and after 168 hours [%]

| Example 4a-72 h (n = 3) | Example 4a-168 h (n = 3) | Ref. Ex. 4b-72 h (n = 3) | Ref. Ex. 4b-168 h (n = 3) |
|---|---|---|---|
| 49.26 | 79.57 | 40.24 | 75.92 |

In Vivo Study Using Goettingen Minipigs

The in vivo releases and the corresponding skin permeation rates of TTS prepared according to Example 4a and Reference Example 4b were determined by in vivo experiments using Goettingen minipigs (female, about 6 months, randomized by simple random sample method). Diecuts with an area of 10 cm² were punched from the TTS and one Goettingen minipig was used for one TTS formulation. Three drug containing and one placebo TTS (each 10 cm²) were used per minipig. The total wear time of all 4 patches per minipig (3 active and 1 placebo patch) was 84 hours.

During the study, the minipigs were kept at 22±3° C., at a relative humidity of 40±15%, lighted from 6 am to 6 µm with calorie reduced breeding food, ssniff, twice daily of about 140-200 g per animal, and with water ad libitum.

Following the above single dose application of the TTS (3*verum and 1 placebo, each 10 cm²), 3 ml blood samples were taken at 0 hour, 4 hours, 8 hours, 12 hours, 24 hours, 32 hours, 48 hours, 56 hours, 72 hours, 84 hours and 96 hours, and the blood samples were centrifuged 10 minutes at 2000×g in order to obtain blood plasma. The asenapine blood plasma concentration was deter mined by an LC method with MS/MS detection. AUC values were calculated from the blood plasma concentration. The residual amount of asenapine was determined in the removed TTS by quantitative HPLC (see above) and the dermally delivered amount of asenapine calculated as the difference to the initial amount of asenapine included in the TTS. The results are shown in Table 4.4 and FIG. 4d.

TABLE 4.4

| | Asenapine Blood plasma concentration [ng/ml] | |
|---|---|---|
| Time | Ex. 4a | Ref. Ex. 4b |
| 0 | 0 | 0 |
| 4 | 0.6168 | 0.3042 |
| 8 | 3.1725 | 1.8003 |
| 12 | 6.7140 | 3.3173 |
| 24 | 5.3344 | 4.4292 |
| 32 | 5.4509 | 4.0957 |
| 48 | 5.7822 | 3.6241 |
| 56 | 3.4738 | 2.8258 |
| 72 | 4.7807 | 3.0152 |
| 84 | 4.1305 | 2.5156 |
| 96 | 1.2651 | 0.8502 |
| $AUC_{(0-24)}$ [(ng/ml) hr] | 100.9 | 61.5 |
| $AUC_{(0-48)}$ [(ng/ml) hr] | 233.9 | 157.4 |
| $AUC_{(0-72)}$ [(ng/ml) hr] | 336.9 | 229.9 |
| $AUC_{(0-84)}$ [(ng/ml) hr] | 390.4 | 263.1 |
| $AUC_{(0-96)}$ [(ng/ml) hr] | 422.8 | 283.3 |
| $c_{max}$ [ng/ml] | 6.7 | 4.4 |

The Invention Relates in Particular to the Following Further Items

1. Transdermal therapeutic system for the transdermal administration of asenapine comprising an asenapine-containing layer structure, said asenapine-containing layer structure comprising:
    A) a backing layer; and
    B) an asenapine-containing layer wherein the transdermal therapeutic system comprises a silicone acrylic hybrid polymer.
2. Transdermal therapeutic system according to item 1, wherein the asenapine-containing layer comprises
    1. asenapine; and
    2. the silicone acrylic hybrid polymer.
3. Transdermal therapeutic system according to item 1 or 2, wherein the asenapine-containing layer is a matrix layer, and preferably is a pressure-sensitive adhesive layer.
4. Transdermal therapeutically system according to any one of items 1 to 3,
wherein the asenapine-containing layer structure is an asenapine-containing self-adhesive layer structure.
5. Transdermal therapeutic system according to any one of items 1 to 4,
wherein the asenapine-containing layer structure contains a therapeutically effective amount of asenapine.
6. Transdermal therapeutic system according to any one of items 1 to 5,
wherein the asenapine-containing layer contains at least 0.10 mg/cm², preferably at least 0.30 mg/cm², more preferably at least 0.50 mg/cm² and most preferably at least 0.60 mg/cm² asenapine.
7. Transdermal therapeutic system according to any one of items 1 to 6,
wherein the asenapine-containing layer contains less than 4.0 mg/cm², less than 3.2 mg/cm², less than 2.4 mg/cm² or less than 1.7 mg/cm² asenapine.
8. Transdermal therapeutic system according to any one of items 1 to 7,
wherein the area weight of the asenapine-containing layer ranges from 50 to 230 g/m², preferably from 70 to 190 g/m², and more preferably from 90 to 150 g/m².
9. Transdermal therapeutic system according to any one of items 1 to 8, wherein the amount of asenapine in the asenapine-containing layer ranges from 2 to 25%, preferably from 3 to 20% and more preferably from 4 to 15% of the asenapine-containing layer.

10. Transdermal therapeutic system according to any one of items 1 to 9,
wherein the amount of asenapine contained in the transdermal therapeutic system ranges from 3 to 100 mg, preferably from 3 to 21 mg or from 10 to 80 mg, and most preferably from 3.5 to 14 mg or from 15 to 60 mg.

11. Transdermal therapeutic system according to any one of items 1 to 10,
wherein the asenapine has a purity of at least 95%, preferably of at least 98% and more preferably of at least 99% as determined by quantitative HPLC.

12. Transdermal therapeutic system according to any one of items 1 to 11,
wherein the asenapine in the asenapine-containing layer is included in the form of the free base.

13. Transdermal therapeutic system according to any one of items 1 to 12,
wherein the asenapine-containing layer is obtainable by incorporating the asenapine in the form of the free base.

14. Transdermal therapeutic system according to any one of items 1 to 13,
wherein at least 90 mol %, preferably at least 95 mol %, more preferably at least 98 mol % and most preferably at least 99 mol % of the asenapine in the asenapine-containing layer is present in the form of the free base.

15. Transdermal therapeutic system according to any one of items 1 to 14,
wherein the asenapine in the asenapine-containing layer is completely dissolved, or
wherein the asenapine-containing layer contains asenapine particles, preferably constituted of asenapine free base.

16. Transdermal therapeutic system according to any one of items 1 to 15,
wherein the amount of the silicone acrylic hybrid polymer ranges from 55 to 98%, preferably from 70 to 98% or from 80 to 98% by weight based on the total weight of the asenapine-containing layer.

17. Transdermal therapeutic system according to any one of items 1 to 16,
wherein the silicone acrylic hybrid polymer is a silicone acrylic hybrid pressure-sensitive adhesive.

18. Transdermal therapeutic system according to any one of items 1 to 17,
wherein the silicone acrylic hybrid polymer is a silicone acrylic hybrid pressure-sensitive adhesive obtainable from
  (a) a silicon-containing pressure-sensitive adhesive composition comprising acrylate or methacrylate functionality.

19. Transdermal therapeutic system according to any one of items 1 to 18,
wherein the silicone acrylic hybrid polymer is a silicone acrylic hybrid pressure-sensitive adhesive comprising the reaction product of
  (a) a silicon-containing pressure-sensitive adhesive composition comprising acrylate or methacrylate functionality;
  (b) an ethylenically unsaturated monomer; and
  (c) an initiator.

20. Transdermal therapeutic system according to item 18 or 19,
wherein the silicon-containing pressure-sensitive adhesive composition comprising acrylate or methacrylate functionality comprises the condensation reaction product of
  (a1) a silicone resin, and
  (a2) a silicone polymer, and
  (a3) a silicon-containing capping agent comprising acrylate or methacrylate functionality.

21. Transdermal therapeutic system according to any one of items 18 to 20,
wherein the silicon-containing pressure-sensitive adhesive composition comprising acrylate or methacrylate functionality comprises the condensation reaction product of
  (a1) a silicone resin, and
  (a2) a silicone polymer, and
  (a3) a silicon-containing capping agent comprising acrylate or methacrylate functionality, wherein said silicon-containing capping agent is of the general formula $XYR'_bSiZ_{3-b}$, wherein X is a monovalent radical of the general formula AE, where E is —O— or —NH— and A is an acryl group or methacryl group, Y is a divalent alkylene radical having from 1 to 6 carbon atoms, R' is a methyl or a phenyl radical, Z is a monovalent hydrolysable organic radical or halogen, and b is 0 or 1;
  wherein the silicone resin and silicone polymer are reacted to form a pressure-sensitive adhesive, wherein the silicon-containing capping agent is introduced prior to, during, or after the silicone resin and silicone polymer are reacted,
  and wherein the silicon-containing capping agent reacts with the pressure-sensitive adhesive after the silicone resin and silicone polymer have been condensation reacted to form the pressure-sensitive adhesive, or the silicon-containing capping agent reacts in situ with the silicone resin and silicone polymer.

22. Transdermal therapeutic system according to any one of items 19 to 21,
wherein the ethylenically unsaturated monomer is selected from the group consisting of aliphatic acrylates, aliphatic methacrylates, cycloaliphatic acrylates, cycloaliphatic methacrylates, and combinations thereof, each of said compounds having up to 20 carbon atoms in the alkyl radical.

23. Transdermal therapeutic system according to any one of items 19 to 22,
wherein the reaction product of
  (a) the silicon-containing pressure-sensitive adhesive composition comprising acrylate or methacrylate functionality;
  (b) the ethylenically unsaturated monomer; and
  (c) the initiator
contains a continuous, silicone external phase and a discontinuous, acrylic internal phase.

24. Transdermal therapeutic system according to any one of items 19 to 22,
wherein the reaction product of
  (a) the silicon-containing pressure-sensitive adhesive composition comprising acrylate or methacrylate functionality;
  (b) the ethylenically unsaturated monomer; and
  (c) the initiator contains a continuous, acrylic external phase and a discontinuous, silicone internal phase.

25. Transdermal therapeutic system according to any one of items 1 to 17,
wherein the silicone acrylic hybrid polymer comprises a reaction product of a silicone polymer, a silicone resin and an acrylic polymer, wherein the acrylic polymer is covalently self-crosslinked and covalently bound to the silicone polymer and/or the silicone resin.

26. Transdermal therapeutic system according to any one of items 1 to 25,
wherein the silicone acrylic hybrid polymer in the asenapine-containing layer contains a continuous, silicone external phase and a discontinuous, acrylic internal phase.

27. Transdermal therapeutic system according to any one of items 1 to 25,
wherein the silicone acrylic hybrid polymer in the asenapine-containing layer contains a continuous, acrylic external phase and a discontinuous, silicone internal phase.

28. Transdermal therapeutic system according to any one of items 1 to 27,
wherein the asenapine-containing layer comprises a non-hybrid polymer,
wherein the non-hybrid polymer preferably is a non-hybrid pressure-sensitive adhesive,
wherein the non-hybrid polymer is preferably selected from polysiloxanes, polyisobutylenes, styrene-isoprene-styrene block copolymers and acrylic polymers.

29. Transdermal therapeutic system according to item 28, wherein the non-hybrid polymer is selected from acrylic polymers.

30. Transdermal therapeutic system according to item 29, wherein the non-hybrid polymer is selected from acrylic polymers comprising functional groups,
wherein the non-hybrid polymer is preferably selected from acrylic polymers comprising hydroxyl groups and no carboxylic acid groups and more preferably is a copolymer based on vinyl acetate, 2-ethylhexyl-acrylate, 2-hydroxyethyl-acrylate and glycidyl-methacrylate.

31. Transdermal therapeutic system according to item 30, wherein the non-hybrid polymer is cross-linked by a cross-linking agent and preferably is cross-linked by a titanium cross-linking agent, or wherein the non-hybrid polymer is not cross-linked by a cross-linking agent.

32. Transdermal therapeutic system according to item 29, wherein the non-hybrid polymer is selected from acrylic polymers comprising no functional groups and preferably is a copolymer based on 2-ethylhexyl-acrylate and vinyl acetate.

33. Transdermal therapeutic system according to any one of items 1 to 32,
wherein the total polymer content in the asenapine-containing layer ranges from 70 to 98%, preferably from 80 to 98% and more preferably from 85 to 98% of the asenapine-containing layer.

34. Transdermal therapeutic system according to any one of items 1 to 33,
wherein the area of release ranges from 5 to 100 cm$^2$, preferably from 10 to 80 cm$^2$, and more preferably from 10 to 60 cm$^2$.

35. Transdermal therapeutic system according to any one of items 1 to 34,
wherein the asenapine-containing layer comprises further excipients or additives selected from the group consisting of crystallization inhibitors, cross-linking agents, solubilizers, fillers, tackifiers, film-forming agents, plasticizers, stabilizers, softeners, substances for skincare, permeation enhancers, pH regulators, and preservatives.

36. Transdermal therapeutic system according to item 35, wherein the tackifier is selected from polyvinyl alcohol, alginate, guar gum, triglycerides, dipropylene glycol, resins, resin esters, terpenes and derivatives thereof, ethylene vinyl acetate adhesives, dimethylpolysiloxanes and polybutenes.

37. Transdermal therapeutic system according to item 35, wherein the film-forming agent is selected from polyvinylpyrrolidone and in particular soluble polyvinylpyrrolidone; a polyethylene glycol, polyvinyl acetate and polyvinylcaprolactame-based graft copolymer; cellulose derivatives and other hydrophilic additives.

38. Transdermal therapeutic system according to item 35, wherein the stabilizer is selected from tocopherol and ester derivatives thereof, ascorbic acid and ester derivatives thereof, butylated hydroxyanisol and butylated hydroxytoluene.

39. Transdermal therapeutic system according to item 35, wherein the permeation enhancer is selected from diethylene glycol monoethyl ether, diisopropyl adipate, isopropyl myristate, isopropyl palmitate, lauryl lactate, dimethylpropylene urea and a mixture of propylene glycol monoesters and diesters of fatty acids.

40. Transdermal therapeutic system according to any one of items 1 to 38,
wherein the asenapine-containing layer does not comprise a permeation enhancer.

41. Transdermal therapeutic system according to any one of items 1 to 40,
wherein the asenapine-containing layer further comprises a copolymer based on dimethylaminoethyl methacrylate, butyl methacrylate and methyl methacrylate.

42. Transdermal therapeutic system according to any one of items 1 to 41,
wherein the transdermal therapeutic system provides a mean release rate of 0.5 to 20 mg/day, preferably of 1.0 to 15 mg/day, and more preferably of 2.0 to 10 mg/day over at least 24 hours of administration, preferably over at least 48 hours of administration, more preferably over at least 72 hours of administration.

43. Transdermal therapeutic system according to any one of items 1 to 42,
wherein the transdermal therapeutic system provides by transdermal delivery one or more pharmacokinetic parameter(s) selected from the group consisting of
an $AUC_{0-48}$ from 20 to 300 (ng/mL) hr, preferably from 30 to 200 (ng/mL) hr,
an $AUC_{0-72}$ from 30 to 400 (ng/mL) hr, preferably from 50 to 300 (ng/mL) hr,
an $AUC_{0-84}$ from 35 to 450 (ng/mL) hr, preferably from 60 to 350 (ng/mL) hr,
a $C_{max}$ to $C_{48}$ ratio of less than 2.0, preferably of less than 1.5 and more preferably of less than 1.3,
a $C_{max}$ to $C_{72}$ ratio of less than 3.0, preferably of less than 2.5 and more preferably of less than 2.0, and
a $C_{max}$ to $C_{84}$ ratio of less than 3.5, preferably of less than 3.0, more preferably of less than 2.5 and most preferably of less than 2.0.

44. Transdermal therapeutic system according to any one of items 1 to 43,
providing a cumulative skin permeation rate of asenapine at hour 48 or at hour 72 as measured in a Franz diffusion cell with dermatomed human skin of 1 μg/cm$^2$-hr to 20 μg/cm$^2$-hr, preferably of 2 μg/cm$^2$-hr to 17 μg/cm$^2$-hr and more preferably of 4 μg/cm$^2$-hr to 12 μg/cm$^2$-hr.

45. Transdermal therapeutic system according to any one of items 1 to 44,
providing a skin permeation rate of asenapine as measured in a Franz diffusion cell with dermatomed human skin of
0 μg/cm$^2$-hr to 10 μg/cm$^2$-hr in the first 8 hours,
2 μg/cm$^2$-hr to 20 μg/cm$^2$-hr from hour 8 to hour 24,
5 μg/cm$^2$-hr to 25 μg/cm$^2$-hr from hour 24 to hour 32,
3 μg/cm$^2$-hr to 22 μg/cm$^2$-hr from hour 32 to hour 48,
2 μg/cm$^2$-hr to 20 μg/cm$^2$-hr from hour 48 to hour 72.

46. Transdermal therapeutic system according to any one of items 1 to 45,
providing a cumulative permeated amount of asenapine as measured in a Franz diffusion cell with dermatomed human skin
of 0.05 mg/cm$^2$ to 1.0 mg/cm$^2$, preferably of 0.1 mg/cm$^2$ to 0.8 mg/cm$^2$ over a time period of 48 hours, or
of 0.1 mg/cm$^2$ to 2.0 mg/cm$^2$, preferably 0.2 mg/cm$^2$ to 1.2 mg/cm$^2$ over a time period of 72 hours.

47. Transdermal therapeutic system according to any one of items 1 to 46, further comprising a release liner and/or an adhesive overlay.

48. Transdermal therapeutic system according to any one of items 1 to 47,
wherein the backing layer is substantially asenapine-impermeable.

49. Transdermal therapeutic system according to any one of items 1 to 48,
wherein the asenapine-containing layer structure comprises or does not comprise an additional skin contact layer.

50. Transdermal therapeutic system according to any one of items 1 to 49,
wherein the transdermal therapeutic system is a matrix-type TTS.

51. Transdermal therapeutic system according to any one of items 1 to 50
for use in a method of treatment.

52. Transdermal therapeutic system according to item 51
for use in a method of treating schizophrenia and/or bipolar disorder.

53. Transdermal therapeutic system according to item 51
for use in a method of treating bipolar disorder, in particular acute manic or mixed episodes of bipolar disorder.

54. Transdermal therapeutic system according to any one of items 51 to 53
for use in a method of treatment with a dosing interval of at least 24 hours or 1 day, at least 48 hours or 2 days, or at least 72 hours or 3 days.

55. Transdermal therapeutic system according to any one of items 51 to 54
for use in a method of treatment with a dosing interval of up to 168 hours or 7 days, up to 120 hours or 5 days, or up to 96 hours or 4 days.

56. Transdermal therapeutic system according to item 54
for use in a method of treatment with a dosing interval of 24 hours or 1 day, of 48 hours or 2 days, or of 84 hours or 3.5 days.

57. A method of treatment
including applying a transdermal therapeutic system according to any one of items 1 to 50 to the skin of a patient.

58. A method of treating schizophrenia and/or bipolar disorder
including applying a transdermal therapeutic system according to any one of items 1 to 50 to the skin of a patient.

59. A method of treating bipolar disorder and in particular acute manic or mixed episodes of bipolar disorder
including applying a transdermal therapeutic system according to any one of items 1 to 50 to the skin of a patient.

60. A method of treatment according to any one of items 57 to 59
including applying a transdermal therapeutic system according to any one of items 1 to 50 for at least 24 hours or 1 day, at least 48 hours or 2 days, or at least 72 hours or 3 days to the skin of a patient.

61. A method of treatment according to any one of items 57 to 60
including applying a transdermal therapeutic system according to any one of items 1 to 50 for up to 168 hours or 7 days, up to 120 hours or 5 days, or up to 96 hours or 4 days to the skin of a patient.

62. A method of treatment according to any one of items 57 to 61
including applying a transdermal therapeutic system according to any one of items 1 to 50 for 24 hours or 1 day, for 48 hours or 2 days, or for 84 hours or 3.5 days to the skin of a patient.

63. A process for manufacturing an asenapine-containing layer for use in a transdermal therapeutic system according to any one of items 2 to 50 comprising the steps of:
  1) combining at least the components asenapine and a silicone acrylic hybrid polymer in a solvent to obtain a coating composition;
  2) coating the coating composition onto the backing layer or release liner; and
  3) drying the coated coating composition to form the asenapine-containing layer.

64. Process for manufacturing an asenapine-containing layer according to item 63, wherein the silicone acrylic hybrid polymer is provided as a solution in ethyl acetate or in n-heptane, preferably in ethyl acetate.

65. The process according to item 63 or 64,
wherein the solvent is selected from alcoholic solvents, in particular methanol, ethanol, isopropanol and mixtures thereof, and from non-alcoholic solvents, in particular ethyl acetate, hexane, n-heptane, petroleum ether, toluene, and mixtures thereof, and more preferably is selected from n-heptane and ethyl acetate.

66. Transdermal therapeutic system for the transdermal administration of asenapine comprising an asenapine-containing self-adhesive layer structure comprising:
  A) a backing layer; and
  B) an asenapine-containing pressure-sensitive adhesive layer comprising:
  1. asenapine included in the form of the free base in an amount of from 4% to 10% of the asenapine-containing pressure-sensitive adhesive layer; and
  2. a silicone acrylic hybrid pressure-sensitive adhesive in an amount of from 90 to 96% of the asenapine-containing pressure-sensitive adhesive layer;
  wherein the area weight of the asenapine-containing pressure-sensitive adhesive layer ranges from 90 to 160 g/m$^2$.

67. Transdermal therapeutic system for the transdermal administration of asenapine comprising an asenapine-containing self-adhesive layer structure comprising:
  A) a backing layer; and
  B) an asenapine-containing pressure-sensitive adhesive layer comprising:
  1. asenapine included in the form of the free base in an amount of from 10% to 17% of the asenapine-containing pressure-sensitive adhesive layer; and
  2. a silicone acrylic hybrid pressure-sensitive adhesive in an amount of from 83 to 90% of the asenapine-containing pressure-sensitive adhesive layer;
  wherein the area weight of the asenapine-containing pressure-sensitive adhesive layer ranges from 90 to 160 g/m$^2$.

The invention claimed is:

1. A transdermal therapeutic system for the transdermal administration of asenapine comprising an asenapine-containing layer structure, said asenapine-containing layer structure comprising:
A) a backing layer; and
B) an asenapine-containing layer;
wherein the transdermal therapeutic system comprises a silicone acrylic hybrid polymer.

2. The transdermal therapeutic system according to claim 1,
wherein the asenapine-containing layer is a matrix layer.

3. The transdermal therapeutically system according to claim 1,
wherein the asenapine-containing layer structure is an asenapine-containing self-adhesive layer structure.

4. The transdermal therapeutic system according to claim 1,
wherein the asenapine-containing layer contains at least 0.10 mg/cm$^2$ asenapine.

5. The transdermal therapeutic system according to claim 1,
wherein the asenapine-containing layer has an area weight ranging from 50 to 230 g/m$^2$.

6. The transdermal therapeutic system according to claim 1,
wherein the asenapine-containing layer contains from 2 to 25% asenapine.

7. The transdermal therapeutic system according to claim 1,
wherein the silicone acrylic hybrid polymer comprises from 55 to 98% by weight of the asenapine-containing layer.

8. The transdermal therapeutic system according to claim 1,
wherein the asenapine in the asenapine-containing layer comprises asenapine free base.

9. The transdermal therapeutic system according to claim 1,
wherein the silicone acrylic hybrid polymer is a silicone acrylic hybrid pressure-sensitive adhesive obtainable from
a silicon-containing pressure-sensitive adhesive composition comprising acrylate or methacrylate functionality.

10. The transdermal therapeutic system according to claim 9,
wherein the silicone acrylic hybrid polymer is a silicone acrylic hybrid pressure-sensitive adhesive comprising the reaction product of
(a) a silicon-containing pressure-sensitive adhesive composition comprising acrylate or methacrylate functionality;
(b) an ethylenically unsaturated monomer; and
(c) an initiator.

11. The transdermal therapeutic system according to claim 9,
wherein the silicon-containing pressure-sensitive adhesive composition comprising acrylate or methacrylate functionality comprises the condensation reaction product of
(a1) a silicone resin, and
(a2) a silicone polymer, and
(a3) a silicon-containing capping agent comprising acrylate or methacrylate functionality.

12. The transdermal therapeutic system according to claim 1,
wherein the silicone acrylic hybrid polymer comprises a reaction product of a silicone polymer, a silicone resin and an acrylic polymer, wherein the acrylic polymer is covalently self-crosslinked and covalently bound to at least one selected from the group consisting of the silicone polymer and the silicone resin.

13. The transdermal therapeutic system according to claim 1,
wherein the silicone acrylic hybrid polymer in the asenapine-containing layer is selected from the group consisting of a silicone acrylic hybrid polymer containing a continuous, silicone external phase and a discontinuous, acrylic internal phase, and a
silicone acrylic hybrid polymer containing a continuous, acrylic external phase and a discontinuous, silicone internal phase.

14. The transdermal therapeutic system according to claim 1,
wherein the asenapine-containing layer comprises a non-hybrid polymer selected from the group consisting of polysiloxanes, polyisobutylenes, styrene-isoprene-styrene block copolymers and acrylic polymers.

15. The transdermal therapeutic system according to claim 1,
wherein the total polymer content in the asenapine-containing layer ranges from 70 to 98%.

16. The transdermal therapeutic system according to claim 1 for use in a method of treating at least one selected from the group consisting of schizophrenia and bipolar disorder.

17. A method of treating at least one condition selected from the group consisting of schizophrenia and bipolar disorder, the method comprising applying the transdermal therapeutic system according to claim 1 to the skin of a patient.

18. The transdermal therapeutic system according to claim 1,
wherein the asenapine-containing layer comprises
asenapine and
the silicone acrylic hybrid polymer.

19. A process for manufacturing an asenapine-containing layer for use in the transdermal therapeutic system according to claim 18, the process comprising:
1) combining at least the components asenapine and a silicone acrylic hybrid polymer in a solvent to obtain a coating composition;
2) coating the coating composition onto the backing layer or release liner; and
3) drying the coated coating composition to form the asenapine-containing layer.

* * * * *